US012730376B2

(12) United States Patent
Urakawa et al.

(10) Patent No.: US 12,730,376 B2
(45) Date of Patent: Sep. 8, 2026

(54) PHOTOSENSITIVE COMPOSITION

(71) Applicant: TOKYO OHKA KOGYO CO., LTD., Kanagawa (JP)

(72) Inventors: Kazuki Urakawa, Kanagawa (JP); Takuro Asaba, Kanagawa (JP); Hideki Saijyo, Kanagawa (JP); Hiroki Chisaka, Kanagawa (JP)

(73) Assignee: TOKYO OHKA KOGYO CO., LTD., Kanagawa (JP)

(*) Notice: Subject to any disclaimer, the term of this patent is extended or adjusted under 35 U.S.C. 154(b) by 482 days.

(21) Appl. No.: 18/488,127

(22) Filed: Oct. 17, 2023

(65) Prior Publication Data

US 2024/0192593 A1 Jun. 13, 2024

(30) Foreign Application Priority Data

Oct. 19, 2022 (JP) ................................ 2022-167708

(51) Int. Cl.

*G03F 7/027* (2006.01)
*C07C 69/54* (2006.01)
*G03F 7/004* (2006.01)

(52) U.S. Cl.

CPC .............. *G03F 7/027* (2013.01); *C07C 69/54* (2013.01); *G03F 7/0044* (2013.01)

(58) Field of Classification Search

CPC .... G03F 7/027; C08F 2/44; C08F 2/48; C08F 220/30

See application file for complete search history.

(56) References Cited

U.S. PATENT DOCUMENTS

| | | | | |
|---|---|---|---|---|
| 3,214,492 | A * | 10/1965 | Tucker | C08L 23/06 522/120 |
| 8,492,452 | B2 * | 7/2013 | Loccufier | C07C 235/08 522/182 |
| 2023/0129152 | A1 * | 4/2023 | Klun | C07C 271/20 427/508 |
| 2024/0191003 | A1 * | 6/2024 | Sugawara | C08K 3/08 |
| 2025/0333548 | A1 * | 10/2025 | Urakawa | C08F 2/44 |

FOREIGN PATENT DOCUMENTS

| | | | | |
|---|---|---|---|---|
| CN | 102304333 | A | 1/2012 | |
| EP | 2065362 | A1 * | 6/2009 | C07C 69/63 |
| JP | 08151404 | A * | 6/1996 | |
| JP | 2008-019422 | A | 1/2008 | |
| JP | 2008-248169 | A | 10/2008 | |
| JP | 2017-214465 | A | 12/2017 | |

OTHER PUBLICATIONS

Machine translation of JP 08-151404 (no date) (Year: 0000).*

* cited by examiner

*Primary Examiner* — Amanda C. Walke
(74) *Attorney, Agent, or Firm* — Rankin, Hill & Clark LLP

(57) ABSTRACT

Provided are a highly-curable photosensitive composition capable of forming cured products that are less likely to undergo excessive mass loss even when heated; and a product of curing of such a photosensitive composition. The photosensitive composition includes photopolymerizable compounds (A) and an initiating agent (C), in which the photopolymerizable compounds (A) include a combination of a compound of a specific structure having a radically polymerizable group-containing group or a cationically polymerizable group-containing group and a polyfunctional compound different from the compound of a specific structure.

9 Claims, No Drawings

PHOTOSENSITIVE COMPOSITION

This application is based on and claims the benefit of priority from Japanese Patent Application No. 2022-167708, filed on 19 Oct. 2022, the content of which is incorporated herein by reference.

BACKGROUND OF THE INVENTION

Field of the Invention

The present invention relates to a photosensitive composition and a product of curing of the photosensitive composition.

Related Art

Traditionally, various photosensitive compositions containing a photopolymerizable compound and an initiating agent for curing the photopolymerizable compound are used to form cured products with various functional properties. Such photosensitive compositions often contain various additives depending on the properties of the cured products to be obtained. For example, high refractive index materials are used to form optical elements. Such high refractive index materials are produced from, for example, a composition including an organic component and particles of metal oxide, such as titanium oxide or zirconium oxide, dispersed in the organic component. Such high refractive index materials are proposed to be produced from an energy ray-curable composition including metal oxide particles (A) with a specific particle size, a (meth)acrylate (B), and a photopolymerization initiating agent (C) (see Patent Document 1).

Patent Document 1: Japanese Unexamined Patent Application, Publication No. 2017-214465

SUMMARY OF THE INVENTION

As mentioned above, the composition disclosed in Patent Document 1 can be used to form high-refractive-index cured materials. Unfortunately, cured materials produced from the composition known in the art, such as that disclosed in Patent Document 1, tend to undergo excessive mass loss during post-exposure baking in the process of forming functional materials, such as high refractive index materials. In some cases, the composition known in the art, such as that disclosed in Patent Document 1, is not easy to cure depending on the type of its components.

It is an object of the present invention, which has been made in view of the problem described above, to provide a highly-curable photosensitive composition capable of forming cured products that are less likely to undergo excessive mass loss even when heated and to provide a product of curing of such a photosensitive composition.

The inventors have created a photosensitive composition including photopolymerizable compounds (A) and an initiating agent (C), in which the photopolymerizable compounds (A) include a combination of a compound of a specific structure having a radically polymerizable group-containing group or a cationically polymerizable group-containing group and a polyfunctional compound different from the compound of a specific structure, and completed the present invention based on findings that such a photosensitive composition provides a solution to the problem described above. Specifically, the present invention provides the following aspects.

(1) A photosensitive composition including: photopolymerizable compounds (A); and an initiating agent (C), the photopolymerizable compounds (A) including: a compound (A1) of Formula (A1):

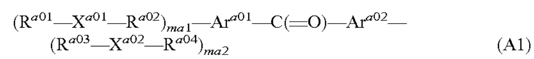

$$(R^{a01}—X^{a01}—R^{a02})_{ma1}—Ar^{a01}—C(=O)—Ar^{a02}—(R^{a03}—X^{a02}—R^{a04})_{ma2} \quad (A1)$$

wherein $Ar^{a01}$ is an aromatic group having 6 or more and 12 or less carbon atoms, having a valence of ma1+1, and optionally substituted with one or more selected from the group consisting of an alkyl group having 1 or more and 5 or less carbon atoms, a cyano group, and a halogen atom, $Ar^{a02}$ is an aromatic group having 6 or more and 12 or less carbon atoms, having a valence of ma2+1, and optionally substituted with one or more selected from the group consisting of an alkyl group having 1 or more and 5 or less carbon atoms, a cyano group, and a halogen atom, $R^{a01}$ and $R^{a04}$ are each independently a radically polymerizable group-containing group or a cationically polymerizable group-containing group, $X^{a01}$ and $X^{a02}$ are each independently O or S, $R^{a02}$ and $R^{a03}$ are each independently an alkylene group, ma1 is an integer of 1 or more and 3 or less, and ma2 is an integer of 0 or more and 3 or less; and at least one additional photopolymerizable compound (A2) different from the compound (A1), the at least one additional photopolymerizable compound (A2) including a polyfunctional compound (A2-1) having two or more polymerizable groups, the initiating agent (C) being different from the compound (A1).

(2) The photosensitive composition according to aspect (1), further including inorganic fine particles (B).

(3) The photosensitive composition according to aspect (2), wherein the inorganic fine particles (B) include metal oxide fine particles (B1), and wherein the metal oxide fine particles (B1) include at least one type of particles selected from the group consisting of titanium oxide fine particles, zirconium oxide fine particles, and niobium oxide fine particles.

(4) The photosensitive composition according to any one of aspects (1) to (3), wherein the polyfunctional compound (A2-1) has four or more polymerizable groups.

(5) The photosensitive composition according to any one of aspects (1) to (4), wherein the ratio of the mass of the compound (A1) to the mass of the photopolymerizable compounds (A) is 40 mass % or more and 60 mass % or less.

(6) The photosensitive composition according to any one of aspects (1) to (5), wherein the radically polymerizable group-containing group is a (meth)acryloyl group-containing group, and the cationically polymerizable group-containing group is an epoxy group-containing group.

(7) The photosensitive composition according to any one of aspects (1) to (6), wherein $Ar^{a01}$ is a group derived from benzene or naphthalene by removal of ma1+1 hydrogen atoms, and $Ar^{a02}$ is a group derived from benzene or naphthalene by removal of ma2+1 hydrogen atoms.

(8) The photosensitive composition according to any one of aspects (1) to (7), wherein $R^{a02}$ and $R^{a03}$ are each independently an alkylene group having 1 or more and 5 or less carbon atoms.

(9) A cured product including a product of curing of the photosensitive composition according to any one of aspects (1) to (8).

The present invention provides a highly-curable photosensitive composition capable of forming cured products that are less likely to undergo excessive mass loss even when heated and provides a product of curing of such a photosensitive composition.

DETAILED DESCRIPTION OF THE INVENTION

Photosensitive Composition

The photosensitive composition includes photopolymerizable compounds (A) and an initiating agent (C). The photopolymerizable compounds (A) include: a compound (A1) of Formula (A1):

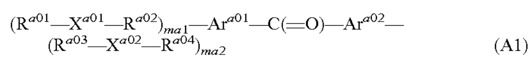

$$(R^{a01}—X^{a01}—R^{a02})_{ma1}—Ar^{a01}—C(=O)—Ar^{a02}—(R^{a03}—X^{a02}—R^{a04})_{ma2} \quad (A1)$$

wherein $Ar^{a01}$ is an aromatic group having 6 or more and 12 or less carbon atoms, having a valence of ma1+1, and optionally substituted with one or more selected from the group consisting of an alkyl group having 1 or more and 5 or less carbon atoms, a cyano group, and a halogen atom, $Ar^{a02}$ is an aromatic group having 6 or more and 12 or less carbon atoms, having a valence of ma2+1, and optionally substituted with one or more selected from the group consisting of an alkyl group having 1 or more and 5 or less carbon atoms, a cyano group, and a halogen atom, $R^{a01}$ and $R^{a04}$ are each independently a radically polymerizable group-containing group or a cationically polymerizable group-containing group, $X^{a01}$ and $X^{a02}$ are each independently O or S, $R^{a02}$ and $R^{a03}$ are each independently an alkylene group, ma1 is an integer of 1 or more and 3 or less, and ma2 is an integer of 0 or more and 3 or less; and at least one additional photopolymerizable compound (A2) different from the compound (A1). The at least one additional photopolymerizable compound (A2) includes a polyfunctional compound (A2-1) having two or more polymerizable groups. The photosensitive composition containing the compound (A1) of Formula (A1) and the polyfunctional compound (A2-1) is highly curable and can form cured products that are less likely to undergo excessive mass loss even when heated. Hereinafter, essential and optional components of the photosensitive composition will be described.

Photopolymerizable Compound (A)

The photosensitive composition contains photopolymerizable compounds (A). The photopolymerizable compounds (A) have a radically polymerizable group-containing group or a cationically polymerizable group-containing group.

The radically polymerizable group-containing group is typically an ethylenically unsaturated double bond-containing group. The ethylenically unsaturated double bond-containing group is preferably an alkenyl group-containing group, which contains an alkenyl group such as vinyl or allyl, and more preferably a (meth)acryloyl group-containing group. The cationically polymerizable group-containing group is typically an epoxy group-containing group, an oxetanyl group-containing group, a vinyloxy group-containing group, or a vinylthio group-containing group. Among them, an epoxy group-containing group and a vinyloxy group-containing group are preferred. The epoxy group-containing group is preferably an alicyclic epoxy group-containing group or a glycidyl group. In this regard, the alicyclic epoxy group is an aliphatic cyclic group having two adjacent carbon atoms as ring members bonded together with an oxygen atom between them. In other words, the alicyclic epoxy group has an aliphatic ring and an epoxy group that is a three-membered ring composed of one oxygen atom and two carbon atoms on the aliphatic ring.

In the description and claims of the present application, the term "(meth)acrylic" means both "acrylic" and "methacrylic", the term "(meth)acryloyl" means both "acryloyl" and "methacryloyl", and the term "(meth)acrylate" means both "acrylate" and "methacrylate".

Compound (A1) As stated above, the photopolymerizable compounds (A) include a compound (A1) of Formula (A1) below.

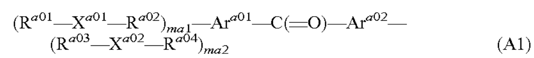

$$(R^{a01}—X^{a01}—R^{a02})_{ma1}—Ar^{a01}—C(=O)—Ar^{a02}—(R^{a03}—X^{a02}—R^{a04})_{ma2} \quad (A1)$$

In Formula (A1), $Ar^{a01}$ is an aromatic group having 6 or more and 12 or less carbon atoms, having a valence of ma1+1, and optionally substituted with one or more selected from the group consisting of an alkyl group having 1 or more and 5 or less carbon atoms, a cyano group, and a halogen atom, $Ar^{a02}$ is an aromatic group having 6 or more and 12 or less carbon atoms, having a valence of ma2+1, and optionally substituted with one or more selected from the group consisting of an alkyl group having 1 or more and 5 or less carbon atoms, a cyano group, and a halogen atom, $R^{a01}$ and $R^{a04}$ are each independently a radically polymerizable group-containing group or a cationically polymerizable group-containing group, $X^{a01}$ and $X^{a02}$ are each independently O or S, $R^{a02}$ and $R^{a03}$ are each independently an alkylene group, ma1 is an integer of 1 or more and 3 or less, and ma2 is an integer of 0 or more and 3 or less.

In Formula (A1), $Ar^{a01}$ is an aromatic group having 6 or more and 12 or less carbon atoms, having a valence of ma1+1, and optionally substituted with one or more selected from the group consisting of an alkyl group having 1 or more and 5 or less carbon atoms, a cyano group, and a halogen atom. $Ar^{a02}$ is an aromatic group having 6 or more and 12 or less carbon atoms, having a valence of ma2+1, and optionally substituted with one or more selected from the group consisting of an alkyl group having 1 or more and 5 or less carbon atoms, a cyano group, and a halogen atom. The aromatic group may be an aromatic hydrocarbon group or an aromatic heterocyclic group. The aromatic group may be a group derived from an aromatic hydrocarbon, such as benzene, naphthalene, or biphenyl, by removal of ma1+1 or ma2+1 hydrogen atoms or may be a group derived from an aromatic heterocyclic compound, such as quinoline, isoquinoline, quinoxaline, cinnoline, quinazoline, phthalazine, naphthyridine, benzoxazole, benzothiazole, benzimidazole, indole, benzofuran, benzothiophene, isoindole, or isobenzofuran, by removal of ma1+1 or ma2+1 hydrogen atoms.

The aromatic group of $Ar^{a01}$ or $Ar^{a02}$ may be substituted with one or more selected from the group consisting of an alkyl group having 1 or more and 5 or less carbon atoms, a cyano group, and a halogen atom. The aromatic group of $Ar^{a01}$ or $Ar^{a02}$ may be substituted with any number of substituents. The alkyl group having 1 or more and 5 or less carbon atoms may be methyl, ethyl, n-propyl, isopropyl, n-butyl, isobutyl, sec-butyl, tert-butyl, n-pentyl, isopentyl, neopentyl, sec-pentyl, or tert-pentyl. In particular, the alkyl group having 1 or more and 5 or less carbon atoms is preferably methyl or ethyl. The halogen atom may be fluorine, chlorine, bromine, or iodine. The aromatic group of $Ar^{a01}$ or $Ar^{a02}$ described above is preferably a group derived from benzene or naphthalene by removal of ma1+1 or ma2+1 hydrogen atoms, and more preferably a group derived from benzene by removal of ma1+1 or ma2+1 hydrogen atoms.

$R^{a01}$ and $R^{a04}$ are each independently a radically polymerizable group-containing group or a cationically polymerizable group-containing group. The radically polymerizable group and the cationically polymerizable group are as described above. The radically polymerizable group-containing group of $R^{a01}$ or $R^{a04}$ is preferably a (meth)acryloyl group-containing group, more preferably a (meth)acryloyl group. The cationically polymerizable group-containing group of $R^{a01}$ or $R^{a4}$ is preferably a vinyl group, a vinyloxy group-containing group, or an epoxy group-containing group, more preferably a vinyl group or an epoxy group-containing group, even more preferably an alicyclic epoxy group-containing group or a glycidyl group. In general, the vinyl group is a radically polymerizable group. In Formula (A1), however, the vinyl group of $R^{a01}$ or $R^{a04}$ and 0 or S represented by $X^{a01}$ or $X^{a02}$ form a vinyloxy or vinylthio group, which is a cationically polymerizable group. In Formula (A1), therefore, the vinyl group of $R^{a01}$ or $R^{a04}$ should be considered not as a radically polymerizable group but as a cationically polymerizable group. The alicyclic epoxy group-containing group is preferably a group of Formula (a1-IIIa) or (a1-IIIb) shown later.

$R^{a02}$ and $R^{a03}$ are each independently an alkylene group. The alkylene group may be linear or branched. The alkylene group preferably has 1 or more and 20 or less carbon atoms, more preferably 1 or more and 10 or less carbon atoms, even more preferably 1 or more and 5 or less carbon atoms. Preferred examples of the alkylene group include methylene, ethane-1,2-diyl, ethane-1,1-diyl, propane-1,3-diyl, propane-1,2-diyl, propane-1,1-diyl, propane-2,2-diyl, n-butane-1,4-diyl, n-pentane-1,5-diyl, n-hexane-1,6-diyl, n-heptane-1,7-diyl, n-octane-1,8-diyl, n-nonane-1,9-diyl, and n-decane-1,10-diyl. In particular, the alkylene group is preferably methylene, ethane-1,2-diyl, or propane-1,3-diyl.

In Formula (A1), $X^{a01}$ and $X^{a02}$ are each independently O or S.

In Formula (A1), ma1 is an integer of 1 or more and 3 or less, and ma2 is an integer of 0 or more and 3 or less. For ease of obtaining the desired effect by using the compound (A1), ma1 is preferably 1 or 2, and ma2 is preferably 0 or 1.

Preferred examples of the compound (A1) include the compounds shown below.

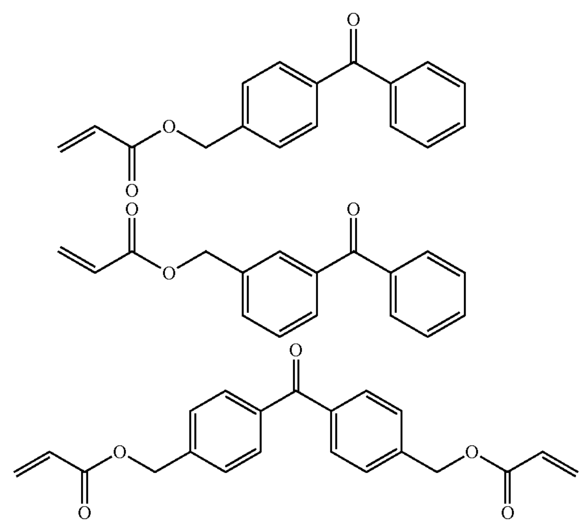

-continued

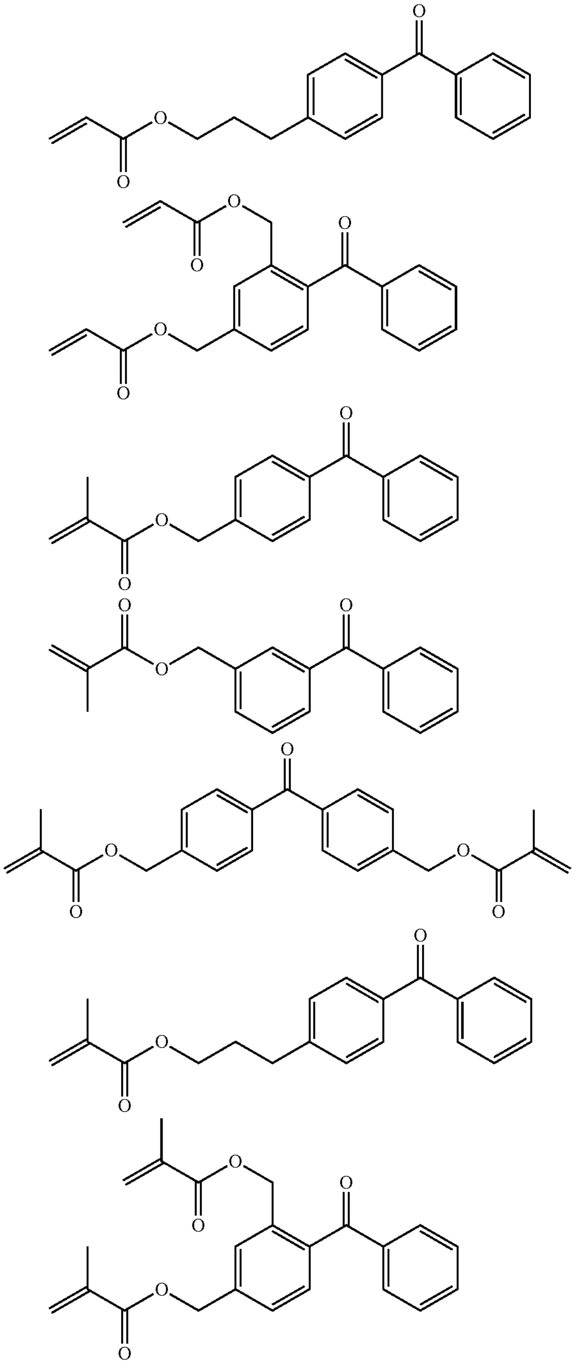

In addition to the compound (A1) described above, the photopolymerizable compounds (A) also include at least one additional photopolymerizable compound (A2), which is different from the compound (A1). In the photosensitive composition, the ratio of the mass of the compound (A1) to the mass of the photopolymerizable compounds (A) is preferably 10 mass % or more and 90 mass % or less, more preferably 20 mass % or more and 80 mass % or less, even more preferably 30 mass % or more and 70 mass % or less, furthermore preferably 40 mass % or more and 60 mass % or less.

Additional Photopolymerizable Compound (A2)

As mentioned above, the photosensitive composition contains the compound (A1) and at least one additional photopolymerizable compound (A2). When the compound (A1) has a radically polymerizable group-containing group, the additional photopolymerizable compound (A2) should also have a radically polymerizable group-containing group. When the compound (A1) has a cationically polymerizable group-containing group, the additional photopolymerizable compound (A2) should also have a cationically polymerizable group-containing group.

The at least one additional photopolymerizable compound (A2) includes a polyfunctional compound (A2-1) having two or more polymerizable groups. The at least one additional photopolymerizable compound (A2) may further include a monofunctional compound having a single polymerizable group.

The polyfunctional compound (A2-1) preferably has three or more polymerizable groups, more preferably four or more polymerizable groups, even more preferably five or more polymerizable groups because its ability to be cured tends to increase as the number of polymerizable groups per molecule increases. There should be no upper limit on the number of polymerizable groups in one molecule of the polyfunctional compound (A2-1). For example, one molecule of the polyfunctional compound (A2-1) preferably has 15 or less polymerizable groups, more preferably 10 or less polymerizable groups.

The polyfunctional compound (A2-1) having radically polymerizable group-containing groups is preferably a compound having two or more (meth)acryloyl groups, such as a (meth)acrylate compound or a (meth)acrylamide compound, more preferably a (meth)acrylate compound having two or more (meth)acryloyl groups.

Examples of the polyfunctional compound (A2-1) having radically polymerizable group-containing groups include a (meth)acrylate having a pentaerythritol skeleton, ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth) acrylate, 1,6-hexane glycol di(meth)acrylate, dimethyloltricyclodecane di(meth)acrylate, trimethylolpropane tri(meth) acrylate, glycerol di(meth)acrylate, 2,2-bis(4-(meth) acryloxydiethoxyphenyl)propane, 2,2-bis(4-(meth) acryloxypolyethoxyphenyl)propane, 2-hydroxy-3-(meth) acryloyloxypropyl (meth)acrylate, ethylene glycol diglycidyl ether di(meth)acrylate, diethylene glycol diglycidyl ether di(meth)acrylate, phthalic acid diglycidyl ester di(meth)acrylate, glycerol triacrylate, glycerol polyglycidyl ether poly(meth)acrylate, urethane (meth)acrylate (i.e., tolylene diisocyanate), reaction products of trimethylhexamethylene diisocyanate, hexamethylene diisocyanate, and 2-hydroxyethyl (meth)acrylate, methylenebis(meth)acrylamide, (meth)acrylamide methylene ether, condensation products of polyhydric alcohol and N-methylol(meth)acrylamide, and other polyfunctional compounds, and triacrylformal. For a higher ability to be cured, the polyfunctional compound is preferably a (meth)acrylate having a pentaerythritol skeleton. These polyfunctional compounds may be used alone, or two or more of these polyfunctional compounds may be used in combination.

Examples of the (meth)acrylate having a pentaerythritol skeleton include:

- difunctional (meth)acrylates having a pentaerythritol skeleton, such as pentaerythritol di(meth)acrylate, dipentaerythritol di(meth)acrylate, tripentaerythritol di(meth)acrylate, pentaerythritol EO adduct di(meth) acrylate, dipentaerythritol EO adduct di(meth)acrylate, and tripentaerythritol EO adduct di(meth)acrylate;
- trifunctional (meth)acrylates having a pentaerythritol skeleton, such as pentaerythritol tri(meth)acrylate, dipentaerythritol tri(meth)acrylate, tripentaerythritol tri (meth)acrylate, pentaerythritol EO adduct tri(meth) acrylate, dipentaerythritol EO adduct tri(meth)acrylate, and tripentaerythritol EO adduct tri(meth)acrylate;
- tetrafunctional (meth)acrylates having a pentaerythritol skeleton, such as pentaerythritol tetra(meth)acrylate, dipentaerythritol tetra(meth)acrylate, tripentaerythritol tetra(meth)acrylate, pentaerythritol EO adduct tetra(meth)acrylate, dipentaerythritol EO adduct tetra(meth) acrylate, and tripentaerythritol EO adduct tetra(meth) acrylate;
- pentafunctional (meth)acrylates having a pentaerythritol skeleton, such as dipentaerythritol penta(meth)acrylate, tripentaerythritol penta(meth)acrylate, dipentaerythritol EO adduct penta(meth)acrylate, and tripentaerythritol EO adduct penta(meth)acrylate;
- hexafunctional (meth)acrylates having a pentaerythritol skeleton, such as dipentaerythritol hexa(meth)acrylate, tripentaerythritol hexa(meth)acrylate, dipentaerythritol EO adduct hexa(meth)acrylate, and tripentaerythritol EO adduct hexa(meth)acrylate;
- heptafunctional (meth)acrylates having a pentaerythritol skeleton, such as tripentaerythritol hepta(meth)acrylate and tripentaerythritol EO adduct hepta(meth)acrylate; and octafunctional (meth)acrylates having a pentaerythritol skeleton, such as tripentaerythritol octa (meth)acrylate and tripentaerythritol EO adduct octa (meth)acrylate.

In the photosensitive composition, the ratio of the mass of the polyfunctional compound (A2-1) to the mass of the photopolymerizable compounds (A) is preferably 10 mass % or more and 90 mass % or less, more preferably 20 mass % or more and 80 mass % or less, even more preferably 30 mass % or more and 70 mass % or less, furthermore preferably 40 mass % or more and 60 mass % or less.

The monofunctional compound having a radically polymerizable group-containing group is preferably a compound having a (meth)acryloyl group, such as a (meth)acrylate compound or a (meth)acrylamide compound, more preferably a (meth)acrylate compound.

Examples of the monofunctional compound having a radically polymerizable group-containing group include (meth)acrylamide, methylol(meth)acrylamide, methoxymethyl(meth)acrylamide, ethoxymethyl(meth)acrylamide, propoxymethyl(meth)acrylamide, butoxymethoxymethyl (meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamido-2-methylpropanesulfonic acid, tert-butyl acrylamide sulfonic acid, methyl (meth)acrylate, ethyl (meth)acrylate, butyl (meth)acrylate, 2-ethylhexyl (meth) acrylate, cyclohexyl (meth)acrylate, 2-hydroxyethyl (meth) acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerol mono(meth)acrylate, tetrahydrofurfuryl (meth)acrylate, dimethylamino(meth)acrylate, glycidyl (meth)acrylate, 2,2,2-trifluoroethyl (meth)acrylate, 2,2,3,3-tetrafluoropropyl (meth)acrylate, and phthalic acid derivative half (meth) acrylate. These monofunctional compounds may be used alone, or two or more of these monofunctional compounds may be used in combination.

The photosensitive composition may contain inorganic fine particles (B), which will be described later. A photosensitive composition containing inorganic fine particles (B) might form a film having an inorganic fine particle (B)-rich layer and an inorganic fine particle (B)-poor layer, which means localization of the inorganic fine particles (B), depending on the components of the photosensitive composition. For prevention of such localization, for prevention of excessive loss of the mass of components being cured during heating, and for higher cross-linking and curing properties, the photosensitive composition preferably contains a compound of Formula (A-2a) or (A-2b) below as the additional photopolymerizable compound (A2) having a radically polymerizable group-containing group(s).

(A-2a)

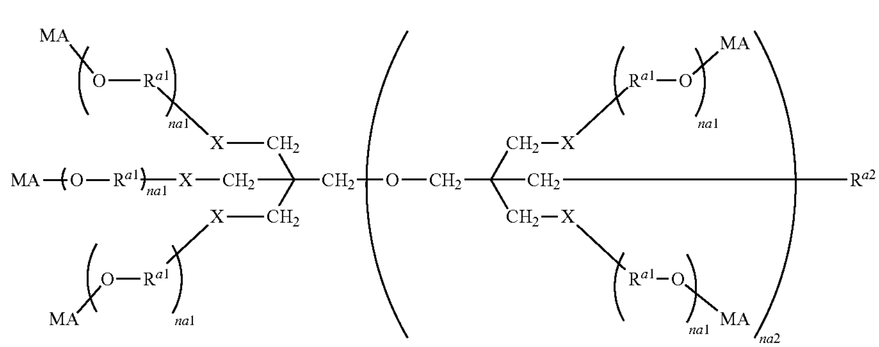

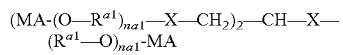

(MA-(O—$R^{a1}$)$_{na1}$—X—$CH_2$)$_2$—CH—X—($R^{a1}$—O)$_{na1}$-MA (A-2b)

In Formulae (A-2a) and (A-2b), MAs are each independently a (meth)acryloyl group, Xs are each independently an oxygen atom, —NH—, or —N($CH_3$)—, $R^{a1}$s are each independently an ethane-1,2-diyl group, a propane-1,2-diyl group, or a propane-1,3-diyl group, $R^{a2}$ is a hydroxyl group, an alkyl group having 1 or more and 4 or less carbon atoms, or a group represented by —X—($R^{a1}$—O)$_{na1}$-MA, wherein X has the same meaning as defined above, and na1 and na2 are each independently 0 or 1.

In Formula (A-2a), the alkyl group of $R^{a2}$ having 1 or more and 4 or less carbon atoms may be methyl, ethyl, n-propyl, isopropyl, n-butyl, isobutyl, sec-butyl, or tert-butyl. In particular, the alkyl group is preferably methyl or ethyl.

Preferred examples of the compounds of Formulae (A-2a) and (A-2b) include pentaerythritol tetra(meth)acrylate, dipentaerythritol hexa(meth)acrylate, trimethylolpropane tri(meth)acrylate, glycerol tri(meth)acrylate, and Compounds (1) to (32) shown below. In Compounds (1) to (32) below, MA is a (meth)acryloyl group.

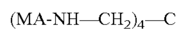

(MA-NH—$CH_2$)$_4$—C (1)

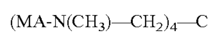

(MA-N($CH_3$)—$CH_2$)$_4$—C (2)

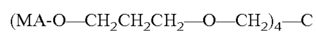

(MA-O—$CH_2CH_2CH_2$—O—$CH_2$)$_4$—C (3)

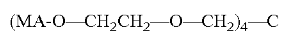

(MA-O—$CH_2CH_2$—O—$CH_2$)$_4$—C (4)

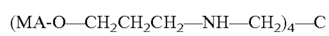

(MA-O—$CH_2CH_2CH_2$—NH—$CH_2$)$_4$—C (5)

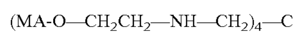

(MA-O—$CH_2CH_2$—NH—$CH_2$)$_4$—C (6)

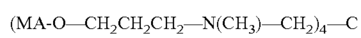

(MA-O—$CH_2CH_2CH_2$—N($CH_3$)—$CH_2$)$_4$—C (7)

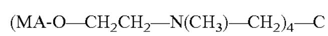

(MA-O—$CH_2CH_2$—N($CH_3$)—$CH_2$)$_4$—C (8)

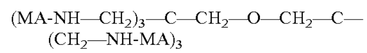

(MA-NH—$CH_2$)$_3$—C—$CH_2$—O—$CH_2$—C—($CH_2$—NH-MA)$_3$ (9)

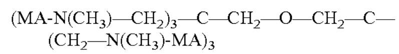

(MA-N($CH_3$)—$CH_2$)$_3$—C—$CH_2$—O—$CH_2$—C—($CH_2$—N($CH_3$)-MA)$_3$ (10)

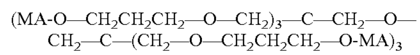

(MA-O—$CH_2CH_2CH_2$—O—$CH_2$)$_3$—C—$CH_2$—O—$CH_2$—C—($CH_2$—O—$CH_2CH_2CH_2$—O-MA)$_3$ (11)

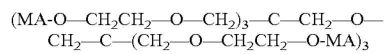

(MA-O—$CH_2CH_2$—O—$CH_2$)$_3$—C—$CH_2$—O—$CH_2$—C—($CH_2$—O—$CH_2CH_2$—O-MA)$_3$ (12)

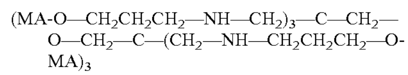

(MA-O—$CH_2CH_2CH_2$—NH—$CH_2$)$_3$—C—$CH_2$—O—$CH_2$—C—($CH_2$—NH—$CH_2CH_2CH_2$—O-MA)$_3$ (13)

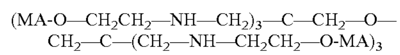

(MA-O—$CH_2CH_2$—NH—$CH_2$)$_3$—C—$CH_2$—O—$CH_2$—C—($CH_2$—NH—$CH_2CH_2$—O-MA)$_3$ (14)

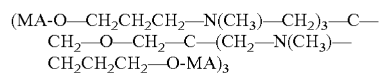

(MA-O—$CH_2CH_2CH_2$—N($CH_3$)—$CH_2$)$_3$—C—$CH_2$—O—$CH_2$—C—($CH_2$—N($CH_3$)—$CH_2CH_2CH_2$—O-MA)$_3$ (15)

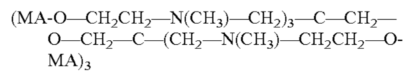

(MA-O—$CH_2CH_2$—N($CH_3$)—$CH_2$)$_3$—C—$CH_2$—O—$CH_2$—C—($CH_2$—N($CH_3$)—$CH_2CH_2$—O-MA)$_3$ (16)

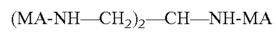

(MA-NH—$CH_2$)$_2$—CH—NH-MA (17)

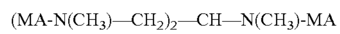

(MA-N($CH_3$)—$CH_2$)$_2$—CH—N($CH_3$)-MA (18)

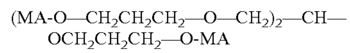

(MA-O—$CH_2CH_2CH_2$—O—$CH_2$)$_2$—CH—$OCH_2CH_2CH_2$—O-MA (19)

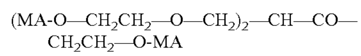

(MA-O—$CH_2CH_2$—O—$CH_2$)$_2$—CH—CO—$CH_2CH_2$—O-MA (20)

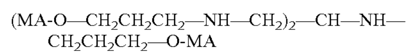

(MA-O—$CH_2CH_2CH_2$—NH—$CH_2$)$_2$—CH—NH—$CH_2CH_2CH_2$—O-MA (21)

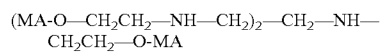

(MA-O—$CH_2CH_2$—NH—$CH_2$)$_2$—$CH_2$—NH—$CH_2CH_2$—O-MA (22)

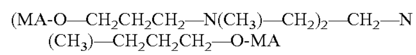

(MA-O—$CH_2CH_2CH_2$—N($CH_3$)—$CH_2$)$_2$—$CH_2$—N($CH_3$)—$CH_2CH_2CH_2$—O-MA (23)

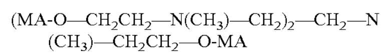

(MA-O—$CH_2CH_2$—N($CH_3$)—$CH_2$)$_2$—$CH_2$—N($CH_3$)—$CH_2CH_2$—O-MA (24)

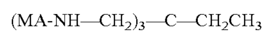

(MA-NH—$CH_2$)$_3$—C—$CH_2CH_3$ (25)

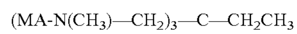

(MA-N($CH_3$)—$CH_2$)$_3$—C—$CH_2CH_3$ (26)

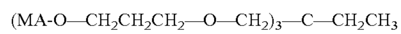

(MA-O—$CH_2CH_2CH_2$—O—$CH_2$)$_3$—C—$CH_2CH_3$ (27)

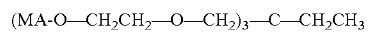

(MA-O—$CH_2CH_2$—O—$CH_2$)$_3$—C—$CH_2CH_3$ (28)

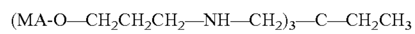

(MA-O—$CH_2CH_2CH_2$—NH—$CH_2$)$_3$—C—$CH_2CH_3$ (29)

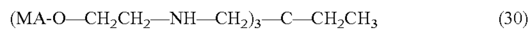

$(MA\text{-}O—CH_2CH_2—NH—CH_2)_3—C—CH_2CH_3$ (30)

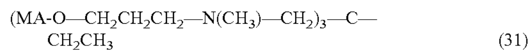

$(MA\text{-}O—CH_2CH_2CH_2—N(CH_3)—CH_2)_3—C—CH_2CH_3$ (31)

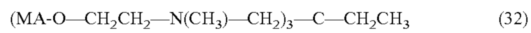

$(MA\text{-}O—CH_2CH_2—N(CH_3)—CH_2)_3—C—CH_2CH_3$ (32)

For production of materials with less localized inorganic fine particles (B) from the photosensitive composition, the ratio of the total mass of the compounds of Formulae (A-2a) and (A-2b) to the mass of the photopolymerizable compounds (A) in the composition is preferably 20 mass % or more and 50 mass % or less, more preferably 30 mass % or more and 50 mass % or less, even more preferably 40 mass % or more and 50 mass % or less.

For ease of producing high refractive index materials from the photosensitive composition, the photosensitive composition preferably contains a compound of Formula (A-2c) below as the additional photopolymerizable compound (A2) having a radically polymerizable group-containing group(s).

(A-2c)

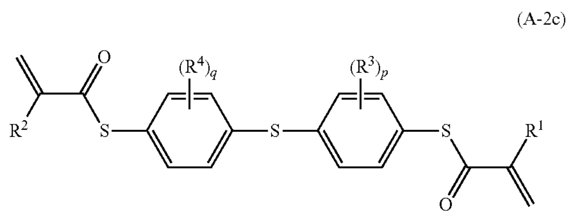

In Formula (A-2c), $R^1$ and $R^2$ are each independently a hydrogen atom or a methyl group, $R^3$ and $R^4$ are each independently an alkyl group having 1 or more and 5 or less carbon atoms, and p and q are each independently 0 or 1.

$R^1$ and $R^2$ are each independently a hydrogen atom or a methyl group. $R^1$ and $R^2$ may be different from each other or may be the same. $R^1$ and $R^2$ are preferably the same so that the compound of Formula (A-2c) can be easily synthesized or obtained commercially.

$R^3$ and $R^4$ are each independently an alkyl group having 1 or more and 5 or less carbon atoms. $R^3$ and $R^4$ may be different from each other or may be the same. $R^3$ and $R^4$ are preferably the same so that the compound of Formula (A-2c) can be easily synthesized or obtained commercially.

The alkyl group of $R^3$ or $R^4$ having 1 or more and 5 or less carbon atoms may be linear or branched. The alkyl group of $R^3$ or $R^4$ having 1 or more and 5 or less carbon atoms may be, for example, methyl, ethyl, n-propyl, isopropyl, n-butyl, isobutyl, sec-butyl, tert-butyl, n-pentyl, isopentyl, or tert-isopentyl.

Preferred examples of the compound of Formula (A-2c) include the compounds below.

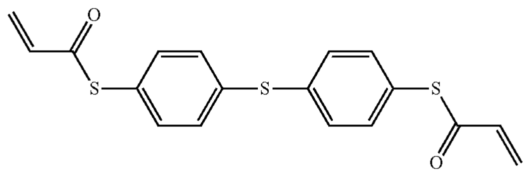

-continued

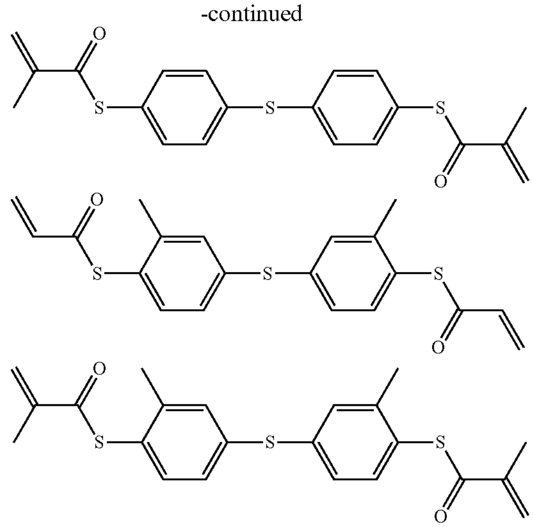

In the photosensitive composition containing the compound of Formula (A-2c) as the additional photopolymerizable compound (A2) having a radically polymerizable group-containing group(s), the ratio of the mass of the compound of Formulae (A-2c) to the mass of the photopolymerizable compounds (A) is preferably 10 mass % or more and 50 mass % or less, more preferably 30 mass % or more and 50 mass % or less.

For ease of producing materials with less localized inorganic fine particles (B) from the photosensitive composition, the photosensitive composition preferably contains a compound of Formula (A-2d) below as the additional photopolymerizable compound (A2) having a radically polymerizable group-containing group(s).

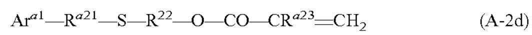

$Ar^{a1}—R^{a21}—S—R^{22}—O—CO—CR^{a23}{=}CH_2$ (A-2d)

In Formula (A-2d), $Ar^{a1}$ is a phenyl group optionally substituted with a halogen atom, $R^{a21}$ is a single bond or an alkylene group having 1 or more and 6 or less carbon atoms, $R^{a22}$ is an alkylene group having 1 or more and 6 or less carbon atoms, and $R^{a23}$ is a hydrogen atom or a methyl group.

$Ar^{a1}$ is a phenyl group optionally substituted with a halogen atom. The phenyl group may be substituted with any number of halogen atoms. The phenyl group is preferably substituted with one or two halogen atoms, more preferably with one halogen atom. The phenyl group may be substituted with two or more halogen atoms the same as or different from one another. The halogen atom, with which the phenyl group may be substituted, may be fluorine, chlorine, bromine, or iodine, and is preferably fluorine, chlorine, or bromine. $Ar^{a1}$ is preferably an unsubstituted phenyl group.

$R^{a21}$ is a single bond or an alkylene group having 1 or more and 6 or less carbon atoms. The alkylene group having 1 or more and 6 or less carbon atoms may be methylene, ethane-1,2-diyl, propane-1,2-diyl, propane-1,3-diyl, butane-1,4-diyl, pentane-1,5-diyl, or hexane-1,6-diyl. $R^{a21}$ is preferably a single bond or a methylene group, and more preferably a single bond.

$R^{a22}$ is an alkylene group having 1 or more and 6 or less carbon atoms. The alkylene group having 1 or more and 6 or less carbon atoms may be methylene, ethane-1,2-diyl, propane-1,2-diyl, propane-1,3-diyl, butane-1,4-diyl, pentane-1,5-diyl, or hexane-1,6-diyl. $R^{a22}$ is preferably methylene, ethane-1,2-diyl, or propane-1,3-diyl, and more preferably ethane-1,2-diyl or propane-1,3-diyl.

In particular, $Ar^{a1}$ and $R^{a21}$ in Formula (A-2d) are preferably a phenyl group and a single bond, respectively, for ease of obtaining the sulfur-containing (meth)acrylate or for production of materials with less localized inorganic fine particles (B) from the photosensitive composition.

Preferred examples of the sulfur-containing (meth)acrylate of Formula (A-2d) include 2-phenylthioethyl (meth) acrylate, 3-phenylthiopropyl (meth)acrylate, 2-benzylthioethyl (meth)acrylate, 3-benzylthiopropyl (meth)acrylate, 2-(2-chlorophenyl)ethyl (meth)acrylate, 2-(3-chlorophenyl) ethyl (meth)acrylate, 2-(4-chlorophenyl)ethyl (meth)acrylate, 3-(2-chlorophenyl)propyl (meth)acrylate, 3-(3-chlorophenyl)propyl (meth)acrylate, 3-(4-chlorophenyl)propyl (meth)acrylate, 2-(2-fluorophenyl)ethyl (meth)acrylate, 2-(3-fluorophenyl)ethyl (meth)acrylate, 2-(4-fluorophenyl) ethyl (meth)acrylate, 3-(2-fluorophenyl)propyl (meth)acrylate, 3-(3-fluorophenyl)propyl (meth)acrylate, 3-(4-fluorophenyl)propyl (meth)acrylate, 2-(2-bromophenyl)ethyl (meth)acrylate, 2-(3-bromophenyl)ethyl (meth)acrylate, 2-(4-bromophenyl)ethyl (meth)acrylate, 3-(2-bromophenyl) propyl (meth)acrylate, 3-(3-bromophenyl)propyl (meth) acrylate, and 3-(4-bromophenyl)propyl (meth)acrylate.

In the photosensitive composition containing the sulfur-containing (meth)acrylate of Formula (A-2d) as the additional photopolymerizable compound (A2) having a radically polymerizable group-containing group(s), the ratio of the mass of the sulfur-containing (meth)acrylate of Formula (A-2d) to the mass of the photopolymerizable compounds (A) is preferably 40 mass % or more and 50 mass % or less.

When the compound (A1) has a cationically polymerizable group-containing group, the additional photopolymerizable compound (A2) may be a monofunctional compound having one cationically polymerizable group or a polyfunctional compound having two or more cationically polymerizable groups, among which a polyfunctional compound is preferred.

The compound (A1) may have a vinyloxy group-containing group as the cationically polymerizable group-containing group. In such a case, the photosensitive composition may contain a vinyl ether compound as the additional photopolymerizable compound (A2). Such a vinyl ether compound may be a monofunctional compound or a polyfunctional compound.

Preferred examples of the vinyl ether compound include vinyl phenyl ether, 4-vinyloxytoluene, 3-vinyloxytoluene, 2-vinyloxytoluene, 1-vinyloxy-4-chlorobenzene, 1-vinyloxy-3-chlorobenzene, 1-vinyloxy-2-chlorobenzene, 1-vinyloxy-2,3-dimethylbenzene, 1-vinyloxy-2,4-dimethylbenzene, 1-vinyloxy-2,5-dimethylbenzene, 1-vinyloxy-2,6-dimethylbenzene, 1-vinyloxy-3,4-dimethylbenzene, 1-vinyloxy-3,5-dimethylbenzene, 1-vinyloxynaphthalene, 2-vinyloxynaphthalene, 2-vinyloxyfluorene, 3-vinyloxyfluorene, 4-vinyloxy-1,1'-biphenyl, 3-vinyloxy-1,1'-biphenyl, 2-vinyloxy-1,1'-biphenyl, 6-vinyloxytetralin, 5-vinyloxytetralin, and other aromatic monoviyl ether compounds; and 1,4-divinyloxybenzene, 1,3-divinyloxybenzene, 1,2-divinyloxybenzene, 1,4-divinyloxynaphthalene, 1,3-divinyloxynaphthalene, 1,2-divinyloxynaphthalene, 1,5-divinyloxynaphthalene, 1,6-divinyloxynaphthalene, 1,7-divinyloxynaphthalene, 1,8-divinyloxynaphthalene, 2,3-divinyloxynaphthalene, 2,6-divinyloxynaphthalene, 2,7-divinyloxynaphthalene, 1,2-divinyloxyfluorene, 3,4-divinyloxyfluorene, 2,7-divinyloxyfluorene, 4,4'-divinyloxybiphenyl, 3,3'-divinyloxybiphenyl, 2,2'-divinyloxybiphenyl, 3,4'-divinyloxybiphenyl, 2,3'-divinyloxybiphenyl, 2,4'-divinyloxybiphenyl, bisphenol A divinyl ether, and other aromatic divinyl ether compounds. Two or more of these vinyl ether compounds may be used in combination.

The compound (A1) may have an epoxy group-containing group as the cationically polymerizable group-containing group. In this case, the photosensitive composition may contain any of various epoxy compounds as the additional photopolymerizable compound (A2). Examples of the epoxy compound include difunctional epoxy resins, such as bisphenol A epoxy resin, bisphenol F epoxy resin, bisphenol S epoxy resin, bisphenol AD epoxy resin, naphthalene epoxy resin, and biphenyl epoxy resin; novolac epoxy resins, such as phenol novolac epoxy resin, brominated phenol novolac epoxy resin, orthocresol novolac epoxy resin, bisphenol A novolac epoxy resin, and bisphenol AD novolac epoxy resin; alicyclic epoxy resins, such as epoxidized dicyclopentadiene phenolic resin; aromatic epoxy resins, such as epoxidized naphthalene phenolic resin; glycidyl ester epoxy resins, such as dimer acid glycidyl esters and triglycidyl esters; glycidyl amine epoxy resins, such as tetraglycidyl aminodiphenylmethane, triglycidyl-p-aminophenol, tetraglycidyl meta-xylylene diamine, and tetraglycidyl bisaminomethylcyclohexane; heterocyclic epoxy resins, such as triglycidyl isocyanurate; trifunctional epoxy resins, such as phloroglucinol triglycidyl ether, trihydroxybiphenyl triglycidyl ether, trihydroxyphenylmethane triglycidyl ether, glycerol triglycidyl ether, 2-[4-(2,3-epoxypropoxy)phenyl]-2-[4-[1,1-bis[4-(2,3-epoxypropoxy)phenyl]ethyl]pheny]propane, and 1,3-bis[4-[1-[4-(2,3-epoxypropoxy)phenyl]-1-[4-[1-[4-(2,3-epoxypropoxy)phenyl]-1-methylethyl]phenyl]ethyl]phenoxy]-2-propanol; tetrafunctional epoxy resins, such as tetrahydroxyphenylethane tetraglycidyl ether, tetraglycidyl benzophenone, bisresorcinol tetraglycidyl ether, and tetraglycidoxybiphenyl; and a 1,2-epoxy-4-(2-oxiranyl)cyclohexane adduct of 2,2-bis(hydroxymethyl)-1-butanol. The 1,2-epoxy-4-(2-oxiranyl)cyclohexane adduct of 2,2-bis(hydroxymethyl)-1-butanol is commercially available under the name EHPE-3150 (manufactured by Daicel Corporation).

The epoxy compound is also preferably an oligomeric or polymeric polyfunctional epoxy compound. Typical examples of the oligomeric or polymeric polyfunctional epoxy compound include phenol novolac epoxy compounds, brominated phenol novolac epoxy compounds, orthocresol novolac epoxy compounds, xylenol novolac epoxy compounds, naphthol novolac epoxy compounds, bisphenol A novolac epoxy compounds, bisphenol AD novolac epoxy compounds, epoxidized dicyclopentadiene phenolic resins, and epoxidized naphthalene phenolic resins.

Other preferred examples of the epoxy compound include polyfunctional alicyclic epoxy compounds having an alicyclic epoxy group.

Examples of the alicyclic epoxy compound include 2-(3,4-epoxycyclohexyl-5,5-spiro-3,4-epoxy)cyclohexane-meta-dioxane, bis(3,4-epoxycyclohexylmethyl) adipate, bis(3,4-epoxy-6-methylcyclohexylmethyl) adipate, 3,4-epoxy-6-methylcyclohexyl-3',4'-epoxy-6'-methyl cyclohexanecarboxylate, ε-caprolactone-modified 3,4-epoxycyclohexylmethyl-3',4'-epoxycyclohexanecarboxylate, trimethylcaprolactone-modified 3,4-epoxycyclohexylmethyl-3',4'-epoxycyclohexanecarboxylate, β-methyl-5-valerolactone-modified 3,4-epoxycyclohexylmethyl-3',4'-epoxycyclohexanecarboxylate, methylenebis(3,4-epoxycyclohexane), ethylene glycol di(3,4-epoxycyclohexylmethyl) ether, ethylenebis(3,4-epoxycyclohexanecarboxylate), dioctyl epoxycyclohexahydrophthalate, di-2-ethylhexyl epoxycyclohexahydrophthalate, epoxy resins having a tricyclodecene oxide group, and compounds of Formulae (a01-1) to (a01-5) below.

Among these examples of the alicyclic epoxy compound, alicyclic epoxy compounds of Formulae (a01-1) to (a01-5) below are preferred because the photosensitive composition containing at least one of them can form materials with high hardness.

(a01-1)

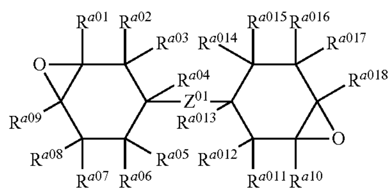

In Formula (a01-1), $Z^{01}$ is a single bond or a linking group (a divalent group having one or more atoms), and $R^{a01}$ to $R^{a018}$ are each independently one selected from the group consisting of a hydrogen atom, a halogen atom, and an organic group.

The linking group $Z^{01}$ may be, for example, a divalent group selected from the group consisting of a divalent hydrocarbon group, —O—, —O—CO—, —S—, —SO—, —$SO_2$—, —$CBr_2$—, —$C(CBr_3)_2$—, —$C(CF_3)_2$—, and —$R^{a019}$—O—CO—, or a group including two or more selected from the above group and bonded together.

The divalent hydrocarbon group for serving as the linking group $Z^{01}$ may be, for example, a linear or branched alkylene group having 1 or more and 18 or less carbon atoms or a divalent alicyclic hydrocarbon group. The linear or branched alkylene group having 1 or more and 18 or less carbon atoms may be, for example, methylene, methylmethylene, dimethylmethylene, dimethylene, or trimethylene. The divalent alicyclic hydrocarbon group may be, for example, 1,2-cyclopentylene, 1,3-cyclopentylene, cyclopentylidene, 1,2-cyclohexylene, 1,3-cyclohexylene, 1,4-cyclohexylene, cyclohexylidene, or any other cycloalkylene group (including any other cycloalkylidene group).

$R^{a019}$ is an alkylene group having 1 or more and 8 or less carbon atoms, and preferably methylene or ethylene.

(a01-2)

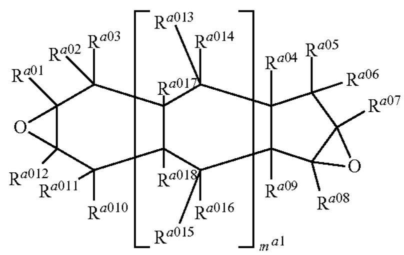

In Formula (a01-2), $R^{a01}$ to $R^{a018}$ are each one selected from the group consisting of a hydrogen atom, a halogen atom, and an organic group, $R^{a02}$ and $R^{a010}$ may be bonded to each other, $R^{a013}$ and $R^{a016}$ may be bonded to each other to form a ring, and $m^{a1}$ is 0 or 1.

The alicyclic epoxy compound of Formula (a01-2) above is preferably a compound of Formula (a01-2-1) below, which corresponds to the compound of Formula (a01-2) in which $m^{a1}$ is 0.

(a01-2-1)

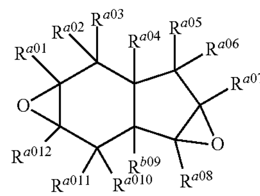

In Formula (a01-2-1), $R^{a01}$ to $R^{a012}$ are each one selected from the group consisting of a hydrogen atom, a halogen atom, and an organic group, and $R^{a02}$ and $R^{a010}$ may be bonded to each other to form a ring.

(a01-3)

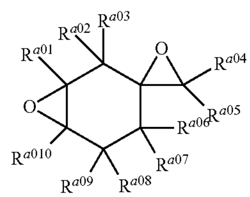

In Formula (a01-3), $R^{a01}$ to $R^{a010}$ are each one selected from the group consisting of a hydrogen atom, a halogen atom, and an organic group, and $R^{a02}$ and $R^{a08}$ may be bonded to each other.

(a01-4)

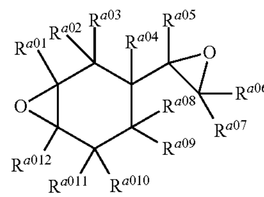

In Formula (a01-4), $R^{a01}$ to $R^{a012}$ are each one selected from the group consisting of a hydrogen atom, a halogen atom, and an organic group, and $R^{a02}$ and $R^{a010}$ may be bonded to each other.

(a01-5)

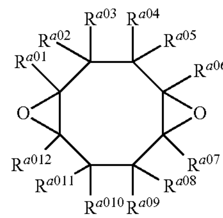

In Formula (a01-5), $R^{a01}$ to $R^{a012}$ are each one selected from the group consisting of a hydrogen atom, a halogen atom, and an organic group.

In Formulae (a01-1) to (a01-5), $R^{a01}$ to $R^{a018}$ may each be any organic group that does not compromise the object of the present invention, such as a hydrocarbon group, a group including carbon and halogen atoms, or a group including carbon and hydrogen atoms and a heteroatom, such as halogen, oxygen, sulfur, nitrogen, or silicon. Examples of the halogen atom include chlorine, bromine, iodine, and fluorine.

The organic group is preferably a hydrocarbon group, a group including carbon, hydrogen, and oxygen atoms, a halogenated hydrocarbon group, a group including carbon, oxygen, and halogen atoms, or a group including carbon, hydrogen, oxygen, and halogen atoms. When the organic group is a hydrocarbon group, the hydrocarbon group may be an aromatic hydrocarbon group, an aliphatic hydrocarbon group, or a group having an aromatic skeleton and an aliphatic skeleton. The number of carbon atoms in the organic group is preferably 1 or more and 20 or less, more preferably 1 or more and 10 or less, even more preferably 1 or more and 5 or less.

Examples of the hydrocarbon group include chain alkyl groups, such as methyl, ethyl, n-propyl, isopropyl, n-butyl, isobutyl, sec-butyl, tert-butyl, n-pentyl, n-hexyl, n-heptyl, n-octyl, 2-ethylhexyl, n-nonyl, n-decyl, n-undecyl, n-tridecyl, n-tetradecyl, n-pentadecyl, n-hexadecyl, n-heptadecyl, n-octadecyl, n-nonadecyl, and n-icosyl; chain alkenyl groups, such as vinyl, 1-propenyl, 2-n-propenyl (allyl), 1-n-butenyl, 2-n-butenyl, and 3-n-butenyl; cycloalkyl groups, such as cyclopropyl, cyclobutyl, cyclopentyl, cyclohexyl, and cycloheptyl; aryl groups, such as phenyl, o-tolyl, m-tolyl, p-tolyl, α-naphthyl, β-naphthyl, biphenyl-4-yl, biphenyl-3-yl, biphenyl-2-yl, anthryl, and phenanthryl; and aralkyl groups, such as benzyl, phenethyl, α-naphthylmethyl, β-naphthylmethyl, α-naphthylethyl, and β-naphthylethyl.

Examples of the halogenated hydrocarbon group include halogenated chain alkyl groups, such as chloromethyl, dichloromethyl, trichloromethyl, bromomethyl, dibromomethyl, tribromomethyl, fluoromethyl, difluoromethyl, trifluoromethyl, 2,2,2-trifluoroethyl, pentafluoroethyl, heptafluoropropyl, perfluorobutyl, perfluoropentyl, perfluorohexyl, perfluoroheptyl, perfluorooctyl, perfluorononyl, and perfluorodecyl; halogenated cycloalkyl groups, such as 2-chlorocyclohexyl, 3-chlorocyclohexyl, 4-chlorocyclohexyl, 2,4-dichlorocyclohexyl, 2-bromocyclohexyl, 3-bromocyclohexyl, and 4-bromocyclohexyl; halogenated aryl groups, such as 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-bromophenyl, 3-bromophenyl, 4-bromophenyl, 2-fluorophenyl, 3-fluorophenyl, and 4-fluorophenyl; and halogenated aralkyl groups, such as 2-chlorophenylmethyl, 3-chlorophenylmethyl, 4-chlorophenylmethyl, 2-bromophenylmethyl, 3-bromophenylmethyl, 4-bromophenylmethyl, 2-fluorophenylmethyl, 3-fluorophenylmethyl, and 4-fluorophenylmethyl.

Examples of the group including carbon, hydrogen, and oxygen atoms include chain hydroxyalkyl groups, such as hydroxymethyl, 2-hydroxyethyl, 3-hydroxy-n-propyl, and 4-hydroxy-n-butyl; hydroxycycloalkyl groups, such as 2-hydroxycyclohexyl, 3-hydroxycyclohexyl, and 4-hydroxycyclohexyl; hydroxyaryl groups, such as 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, and 3,5-dihydroxyphenyl; hydroxyaralkyl groups, such as 2-hydroxyphenylmethyl, 3-hydroxyphenylmethyl, and 4-hydroxyphenylmethyl; chain alkoxy groups, such as methoxy, ethoxy, n-propoxy, isopropoxy, n-butyloxy, isobutyloxy, sec-butyloxy, tert-butyloxy, n-pentyloxy, n-hexyloxy, n-heptyloxy, n-octyloxy, 2-ethylhexyloxy, n-nonyloxy, n-decyloxy, n-undecyloxy, n-tridecyloxy, n-tetradecyloxy, n-pentadecyloxy, n-hexadecyloxy, n-heptadecyloxy, n-octadecyloxy, n-nonadecyloxy, and n-icosyloxy; chain alkenyloxy groups, such as vinyloxy, 1-propenyloxy, 2-n-propenyloxy (allyloxy), 1-n-butenyloxy, 2-n-butenyloxy, and 3-n-butenyloxy; aryloxy groups, such as phenoxy, o-tolyloxy, m-tolyloxy, p-tolyloxy, α-naphthyloxy, β-naphthyloxy, biphenyl-4-yloxy, biphenyl-3-yloxy, biphenyl-2-yloxy, anthryloxy, and phenanthryloxy; aralkyloxy groups, such as benzyloxy, phenethyloxy, α-naphthylmethyloxy, β-naphthylmethyloxy, α-naphthylethyloxy, and -naphthylethyloxy; alkoxyalkyl groups, such as methoxymethyl, ethoxymethyl, n-propoxymethyl, 2-methoxyethyl, 2-ethoxyethyl, 2-n-propoxyethyl, 3-methoxy-n-propyl, 3-ethoxy-n-propyl, 3-n-propoxy-n-propyl, 4-methoxy-n-butyl, 4-ethoxy-n-butyl, and 4-n-propoxy-n-butyl; alkoxyalkoxy groups, such as methoxymethoxy, ethoxymethoxy, n-propoxymethoxy, 2-methoxyethoxy, 2-ethoxyethoxy, 2-n-propoxyethoxy, 3-methoxy-n-propoxy, 3-ethoxy-n-propoxy, 3-n-propoxy-n-propoxy, 4-methoxy-n-butyloxy, 4-ethoxy-n-butyloxy, and 4-n-propoxy-n-butyloxy; alkoxyaryl groups, such as 2-methoxyphenyl, 3-methoxyphenyl, and 4-methoxyphenyl; alkoxyaryloxy groups, such as 2-methoxyphenoxy, 3-methoxyphenoxy, and 4-methoxyphenoxy; aliphatic acyl groups, such as formyl, acetyl, propionyl, butanoyl, pentanoyl, hexanoyl, heptanoyl, octanoyl, nonanoyl, and decanoyl; aromatic acyl groups, such as benzoyl, α-naphthoyl, and β-naphthoyl; chain alkyloxycarbonyl groups, such as methoxycarbonyl, ethoxycarbonyl, n-propoxycarbonyl, n-butyloxycarbonyl, n-pentyloxycarbonyl, n-hexyloxycarbonyl, n-heptyloxycarbonyl, n-octyloxycarbonyl, n-nonyloxycarbonyl, and n-decyloxycarbonyl; aryloxycarbonyl groups, such as phenoxycarbonyl, α-naphthoxycarbonyl, and β-naphthoxycarbonyl; aliphatic acyloxy groups, such as formyloxy, acetyloxy, propionyloxy, butanoyloxy, pentanoyloxy, hexanoyloxy, heptanoyloxy, octanoyloxy, nonanoyloxy, and decanoyloxy; and aromatic acyloxy groups, such as benzoyloxy, α-naphthoyloxy, and β-naphthoyloxy.

$R^{a01}$ to $R^{a018}$ are preferably each independently one selected from the group consisting of a hydrogen atom, a halogen atom, an alkyl group having 1 or more and 5 or less carbon atoms, and an alkoxy group having 1 or more and 5 or less carbon atoms. In particular, for ease of producing materials with excellent mechanical properties from the photosensitive composition, $R^{a01}$ to $R^{a018}$ are preferably all hydrogen atoms.

In Formulae (a01-2) to (a01-5), $R^{a01}$ to $R^{a018}$ each have the same meaning as defined for $R^{a01}$ to $R^{a018}$ in Formula (a01-1). $R^{a02}$ and $R^{a010}$ in Formulae (a01-2) and (a01-4), $R^{a013}$ and $R^{a016}$ in Formula (a01-2), or $R^{a02}$ and $R^{a08}$ in Formula (a01-3) may be bonded to each other to form a divalent group, such as $—CH_2—$ or $—C(CH_3)_2—$.

Preferred examples of the alicyclic epoxy compound of Formula (a01-1) include alicyclic epoxy compounds of Formulae (a01-1a), (a01-1b), and (a01-1c) below and 2,2-bis(3,4-epoxycyclohexan-1-yl)propane (corresponding to 2,2-bis(3,4-epoxycyclohexyl)propane).

(a01-1a)

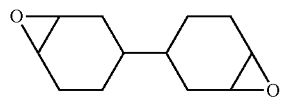

-continued (a01-1b)

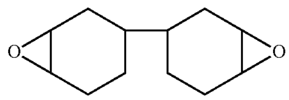

(a01-1c)

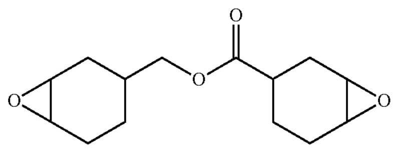

Preferred examples of the alicyclic epoxy compound of Formula (a01-2) include alicyclic epoxy compounds of Formulae (a01-2a) and (a01-2b) below.

(a01-2a)

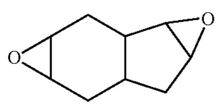

(a01-2b)

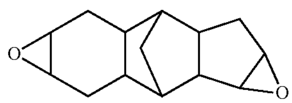

Preferred examples of the alicyclic epoxy compound of Formula (a01-3) include S-spiro[3-oxatricyclo[3.2.1.0$^{2,4}$]octane-6,2'-oxirane].

Preferred examples of the alicyclic epoxy compound of Formula (a01-4) include 4-vinylcyclohexene dioxide, dipentene dioxide, limonene dioxide, 1-methyl-4-(3-methyloxiran-2-yl)-7-oxabicyclo[4.1.0]heptane.

Preferred examples of the alicyclic epoxy compound of Formula (a01-5) include 1,2,5,6-diepoxycyclooctane.

Moreover, the epoxy compound is preferably a compound of Formula (a1-I) below.

(a1-I)

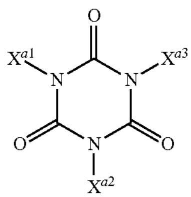

In Formula (a1-I), $X^{a1}$, $X^{a2}$, and $X^{a3}$ are each independently a hydrogen atom or an organic group optionally having an epoxy group, and the total number of epoxy groups in $X^{a1}$, $X^{a2}$, and $X^{a3}$ is 2 or more.

The compound of Formula (a1-I) is preferably a compound of Formula (a1-II) below.

(a1-II)

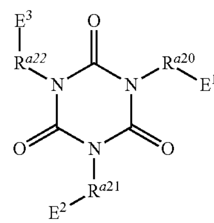

In Formula (a1-II), $R^{a20}$ to $R^{a22}$ are each a linear, branched, or cyclic alkylene group, an arylene group, —O—, —C(═O)—, —NH—, or any combination of these groups and may be the same or different, and $E^1$ to $E^3$ are each a hydrogen atom or at least one substituent selected from the group consisting of an epoxy group, an oxetanyl group, an ethylenically unsaturated group, an alkoxysilyl group, an isocyanate group, a blocked isocyanate group, a thiol group, a carboxy group, a hydroxyl group, and a succinic anhydride group, provided that the total number of epoxy groups in $E^1$, $E^2$, and $E^3$ is 2 or more.

In Formula (a1-II), for example, at least two of the $R^{a20}$-$E^1$ group, the $R^{a21}$-$E^2$ group, and the $R^{a22}$-$E^3$ group are preferably groups of Formula (a1-IIa) below, and more preferably, all of the $R^{a20}$-$E^1$ group, the $R^{a21}$-E2 group, and the $R^{a22}$-$E^3$ group are groups of Formula (a1-IIa) below. In a single compound, two or more groups of Formula (a1-IIa) are preferably the same.

$$\text{-L-}C^a \quad \text{(a1-IIa)}$$

In Formula (a1-IIa), L is a linear, branched, or cyclic alkylene group, an arylene group, —O—, —C(═O)—, —NH—, or any combination of these groups, and $C^a$ is an oxiranyl group (epoxy group). In Formula (a1-IIa), L and $C^a$ may be bonded to form a ring structure.

In Formula (a1-IIa), the linear, branched, or cyclic alkylene group represented by L is preferably an alkylene group having 1 or more and 10 or less carbon atoms, and the arylene group represented by L is preferably an arylene group having 5 or more and 10 or less carbon atoms. In Formula (a1-IIa), L is preferably a linear alkylene group having 1 or more and 3 or less carbon atoms, a phenylene group, —O—, —C(═O)—, —NH—, or any combination of these groups, preferably at least one of a phenylene group or a linear alkylene group having 1 or more and 3 or less carbon atoms, such as methylene, or preferably a group including a combination of any of these groups and at least one of —O—, —C(═O)—, or —NH—.

In Formula (a1-IIa), L and $C^a$ may be bonded to form a ring structure. In this case, for example, a branched alkylene group and an epoxy group may be bonded to form a ring structure (a structure having an alicyclic epoxy group), examples of which include organic groups of Formulae (a1-IIb) to (a1-IId) below.

(a1-IIb)

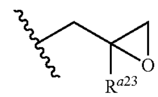

-continued
(a1-IIc)
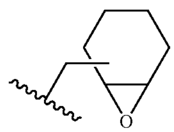
(a1-IId)
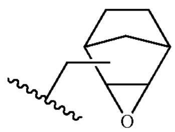
In Formula (a1-IIb), $R^{a23}$ is a hydrogen atom or a methyl group.
Examples of the compound of Formula (a1-II) include, but are not limited to, oxiranyl group- or alicyclic epoxy group-containing epoxy compounds shown below.
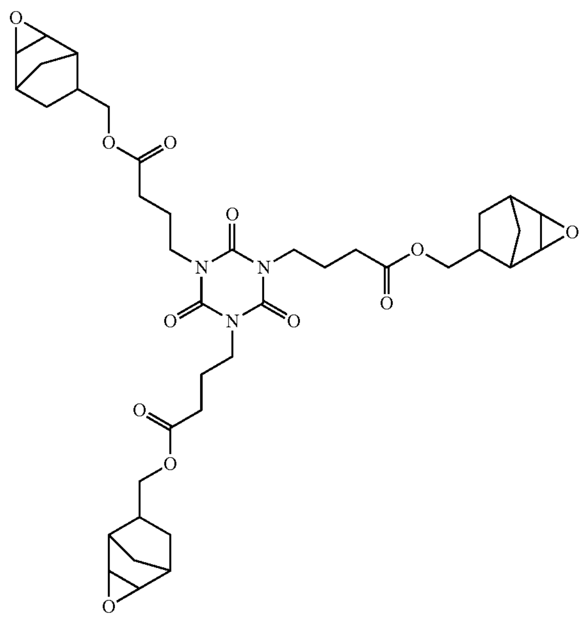
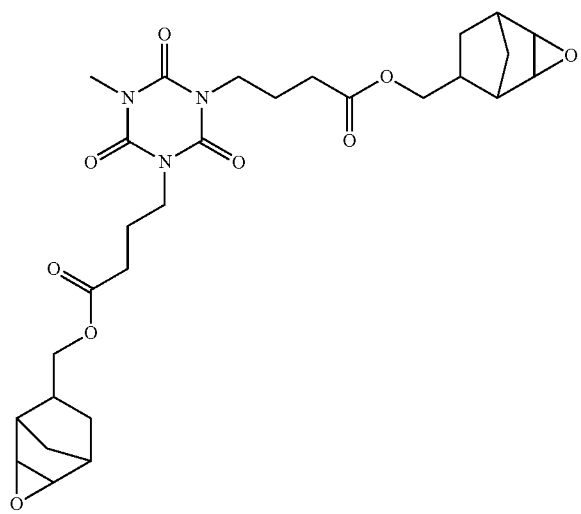
-continued
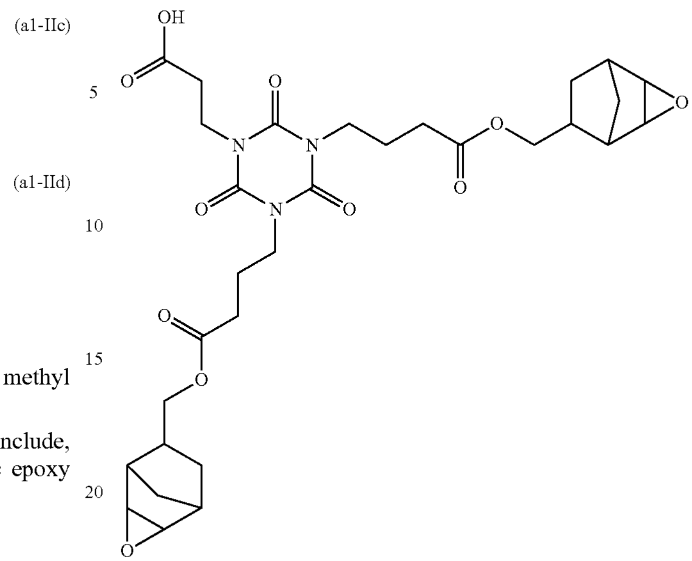
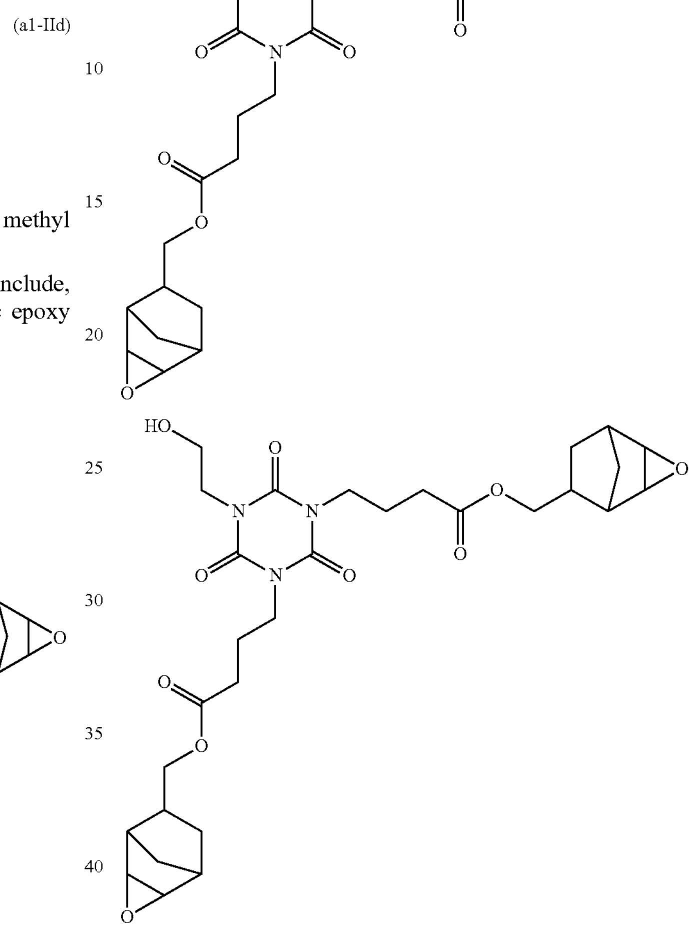
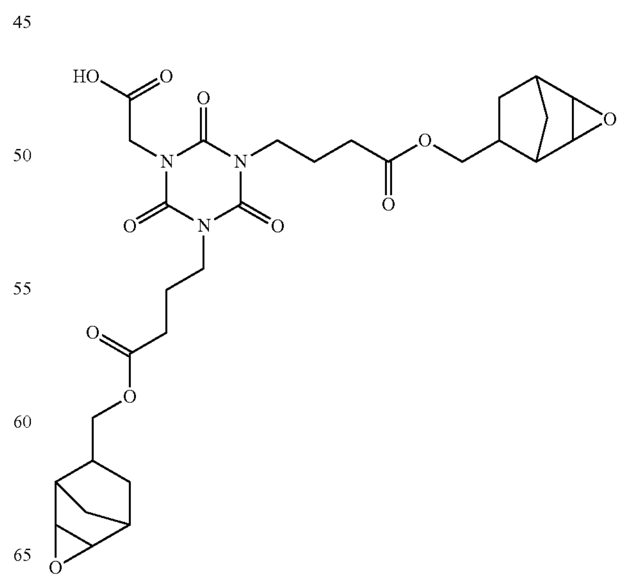

-continued
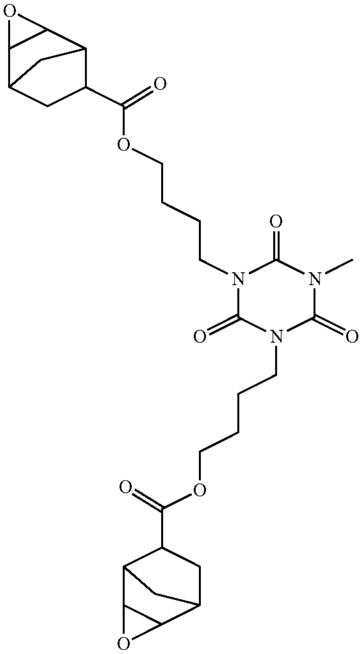
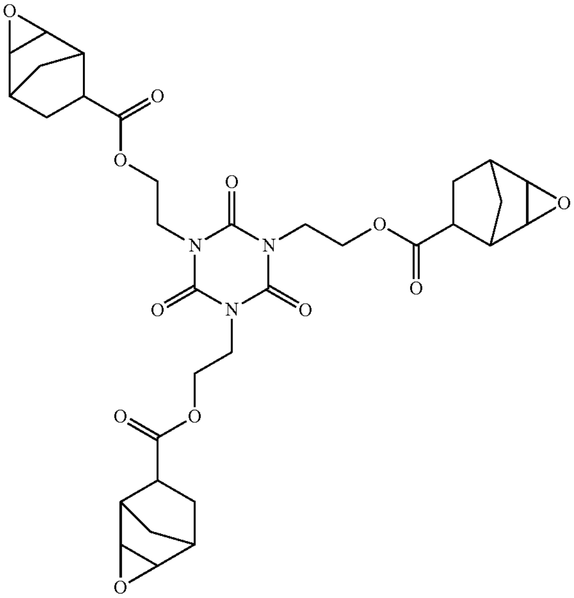
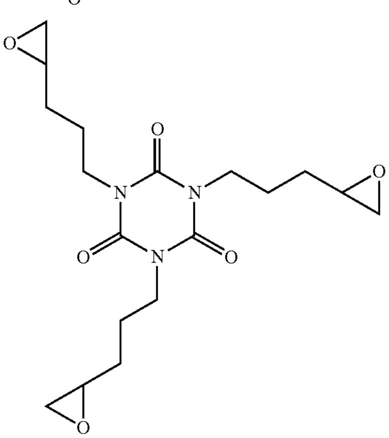
-continued
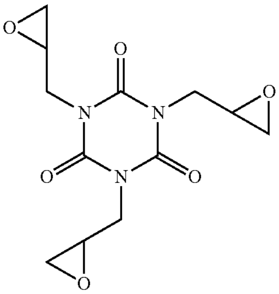
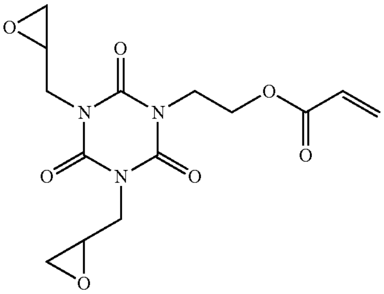
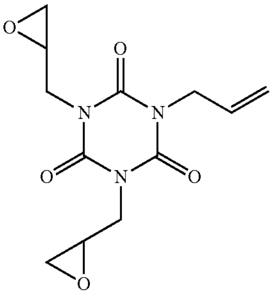
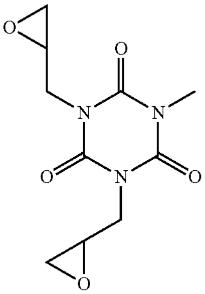
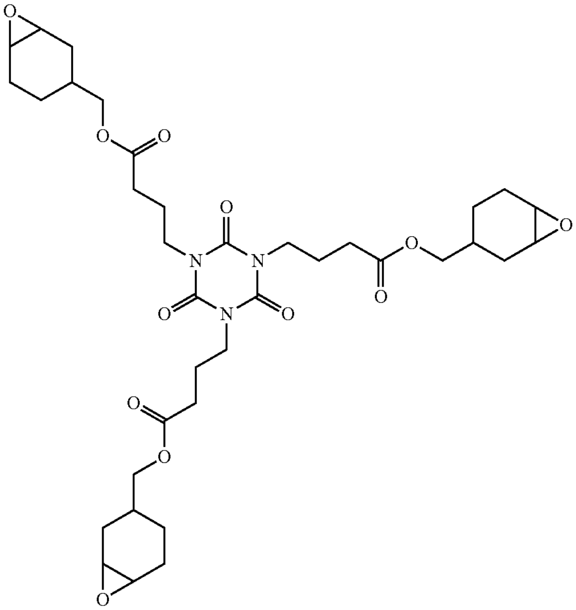

-continued
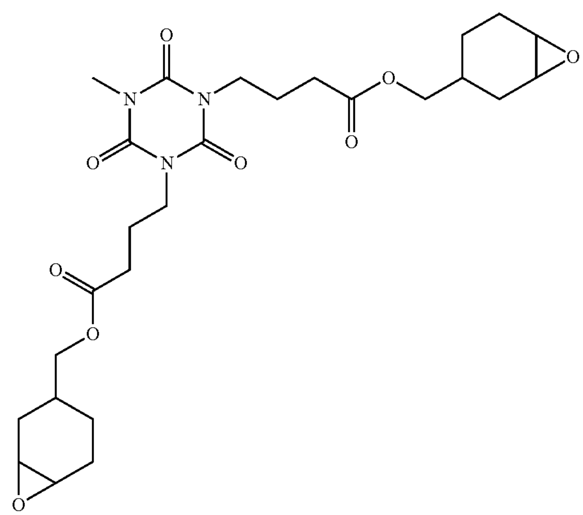
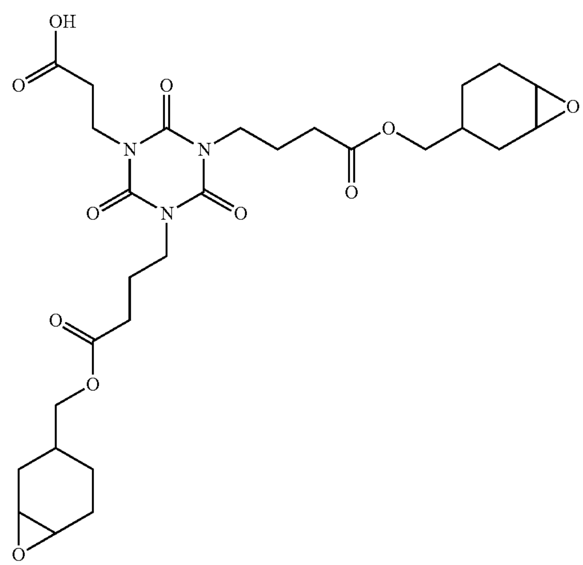
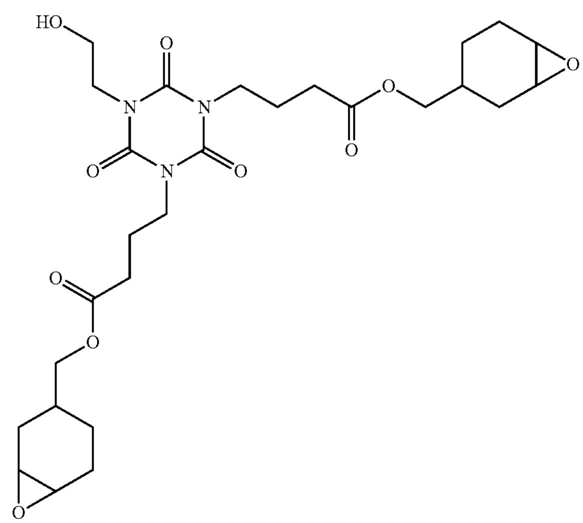
-continued
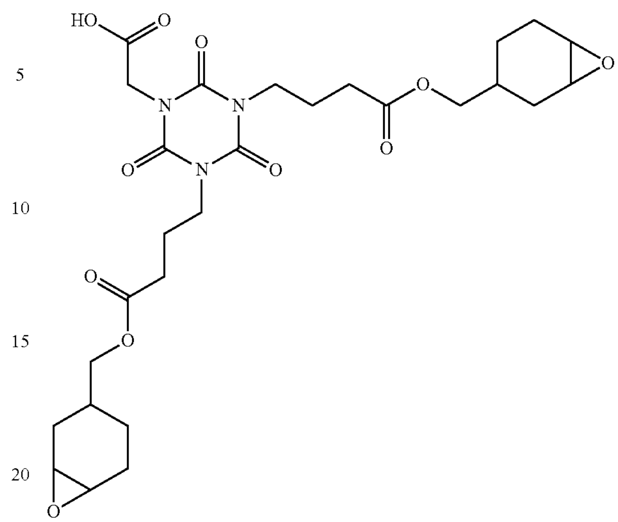
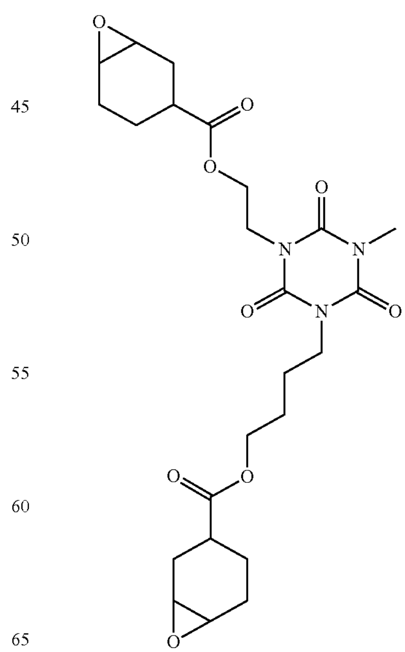

-continued

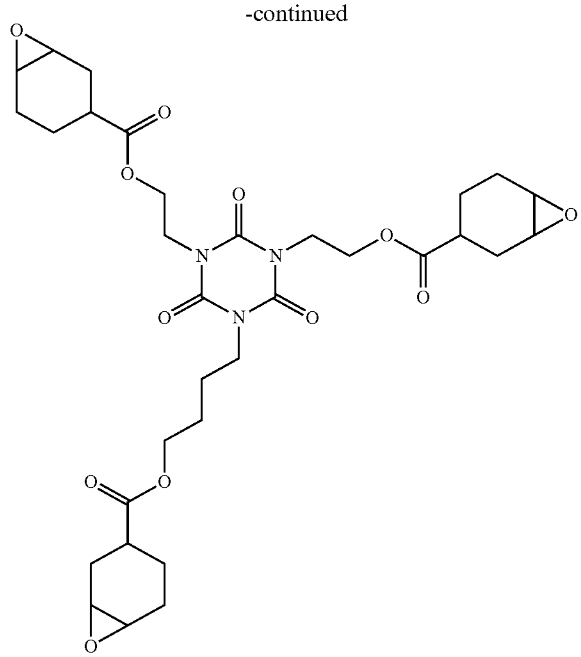

The epoxy compound is also preferably a siloxane compound having two or more glycidyl or alicyclic epoxy groups in the molecule (hereinafter also simply referred to as "siloxane compound").

The siloxane compound has a siloxane skeleton including a siloxane bond (Si—O—Si) and has two or more glycidyl groups or two or more alicyclic epoxy groups in the molecule.

In the siloxane compound, the siloxane skeleton may be, for example, a cyclic siloxane skeleton or a cage or ladder polysilsesquioxane skeleton.

In particular, the siloxane compound is preferably a compound having a cyclic siloxane skeleton of Formula (a1-III) below (hereinafter also referred to as "cyclic siloxane").

(a1-III)

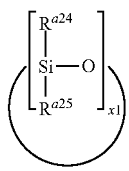

In Formula (a1-III), $R^{a24}$ and $R^{a25}$ are each an epoxy group-containing monovalent group or an alkyl group, provided that at least two of x1 $R^{a24}$s and x1 $R^{a25}$s in the compound of Formula (a1-III) are epoxy group-containing monovalent groups. In Formula (a1-III), x1 is an integer of 3 or more. In the compound of Formula (a1-III), $R^{a24}$ and $R^{a25}$ may be the same or different. Two or more $R^{a24}$s may be the same or different. Two or more $R^{a25}$s may also be the same or different. The alkyl group may be, for example, a linear or branched alkyl group having 1 or more and 18 or less carbon atoms (preferably 1 or more and 6 or less carbon atoms, more preferably 1 or more and 3 or less carbon atoms), such as methyl, ethyl, propyl, or isopropyl.

In Formula (a1-III), x1 is an integer of 3 or more. In particular, for high cross-linking reactivity for production of functional materials from the photosensitive composition, x1 is preferably an integer of 3 or more and 6 or less. The siloxane compound has two or more epoxy groups in the molecule. For high cross-linking reactivity for production of functional materials from the photosensitive composition, the siloxane compound preferably has 2 or more and 6 or less epoxy groups, more preferably 2 or more and 4 or less epoxy groups.

The epoxy group-containing monovalent group is preferably an alicyclic epoxy group or a glycidyl ether group represented by $-D^{A}-O-R^{a26}$, wherein $D^{A}$ is an alkylene group, and $R^{a26}$ is a glycidyl group, more preferably an alicyclic epoxy group, and even more preferably an alicyclic epoxy group of Formula (a1-IIIa) or (a1-IIIb) below. The $D^{A}$ (alkylene) group may be, for example, a linear or branched alkylene group having 1 or more and 18 or less carbon atoms, such as methylene, methylmethylene, dimethylmethylene, dimethylene, or trimethylene.

(a1-IIIa)

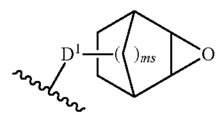

(a1-IIIb)

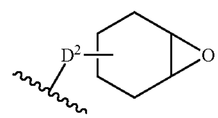

In Formulae (a1-IIIa) and (a1-IIIb), $D^1$ and $D^2$ are each independently an alkylene group, and ms is an integer of 0 or more and 2 or less.

In addition to the siloxane compound of Formula (a1-III), the photosensitive composition may contain, as the epoxy compound, an alicyclic epoxy group-containing cyclic siloxane, an alicyclic epoxy group-containing silicone resin disclosed in Japanese Unexamined Patent Application, Publication No. 2008-248169, or a siloxane skeleton-containing compound, such as an organopolysilsesquioxane resin disclosed in Japanese Unexamined Patent Application, Publication No. 2008-19422, which has at least two epoxy functional groups per molecule.

More specifically, the siloxane compound may be any one of the cyclic siloxanes of the formulae shown below, which have two or more glycidyl groups in the molecule. The siloxane compound may also be a commercially available product, such as X-40-2670, X-40-2701, X-40-2728, X-40-2738, or X-40-2740 (all trade names, manufactured by Shin-Etsu Chemical Co., Ltd.).

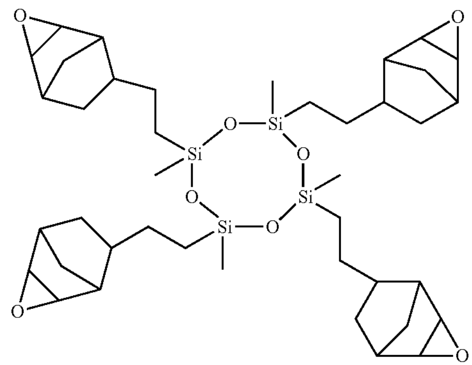

-continued
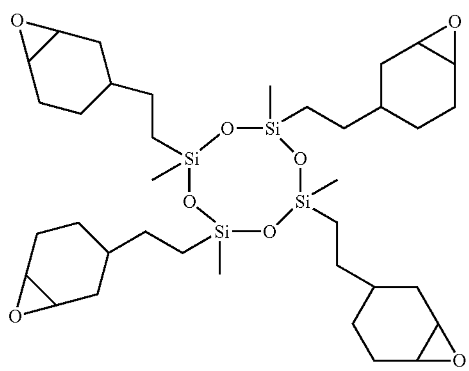
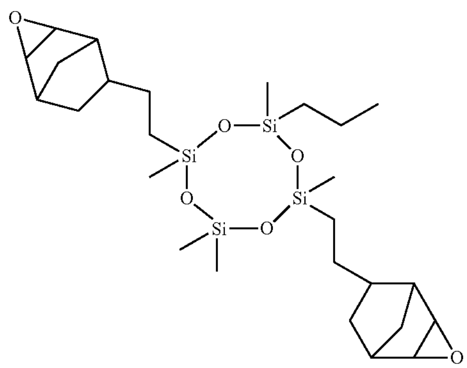
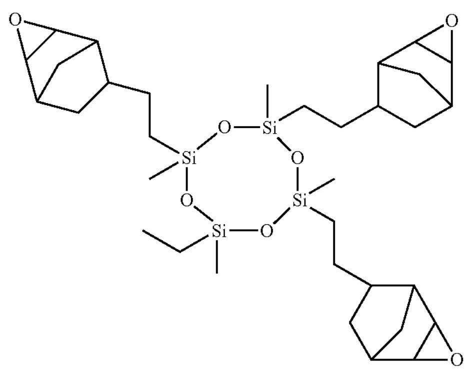
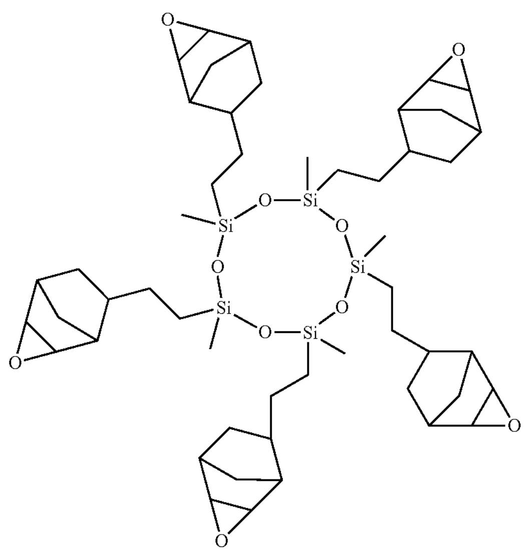
-continued
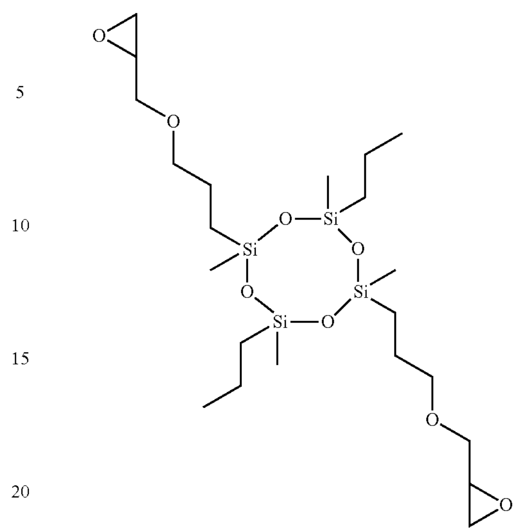
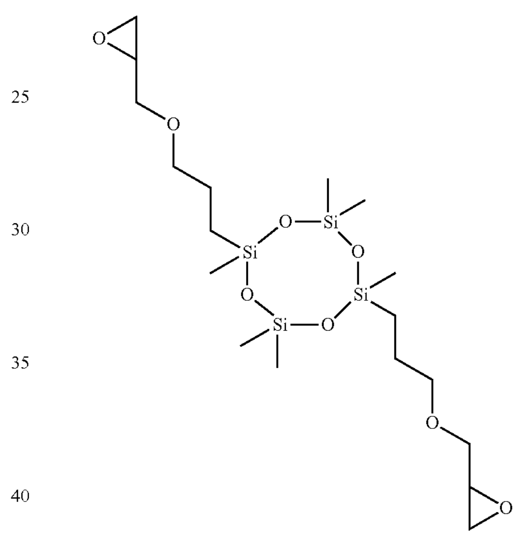
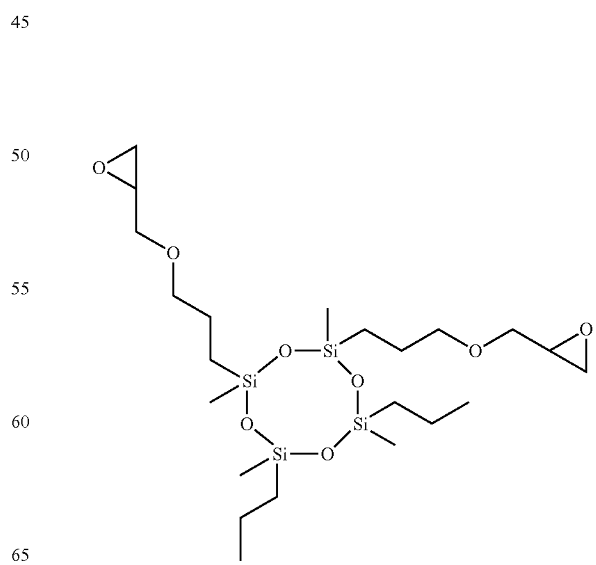

-continued
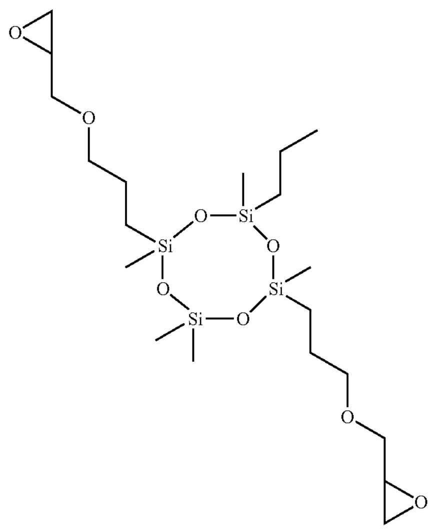
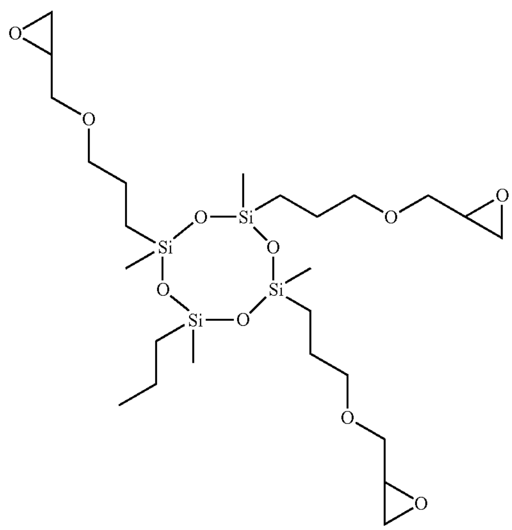
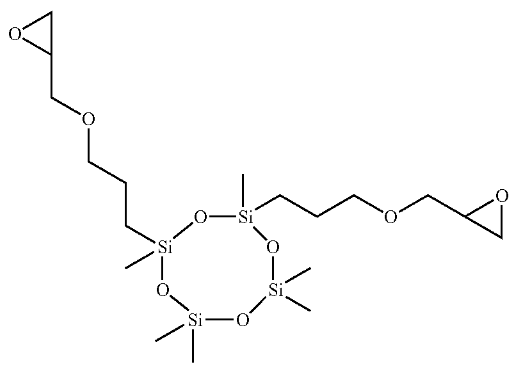
-continued
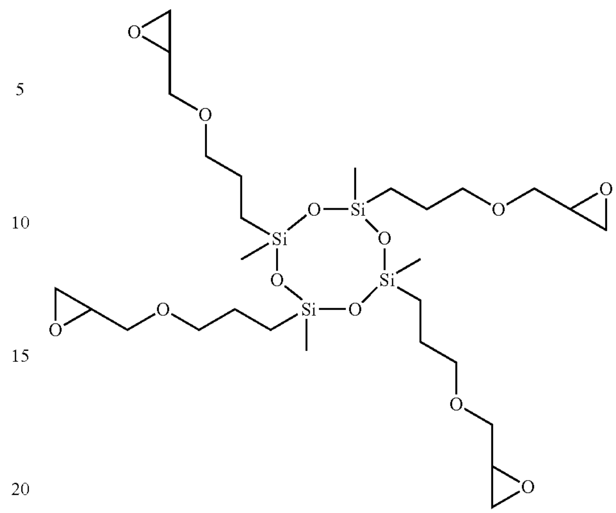
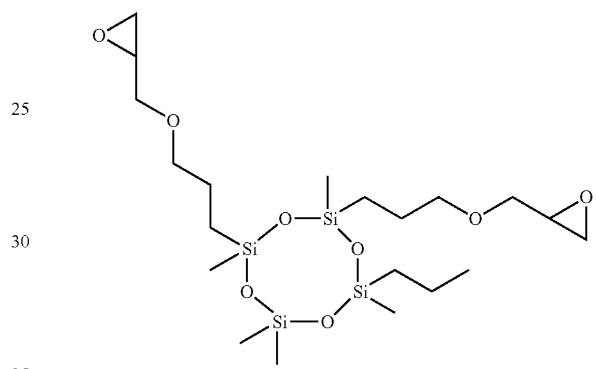
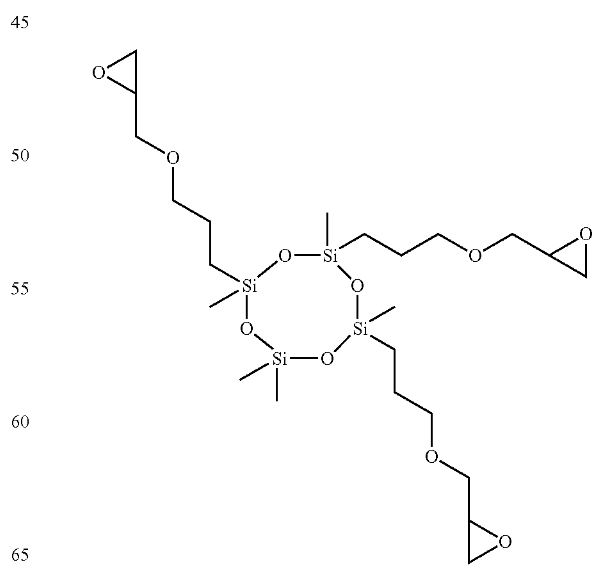

-continued

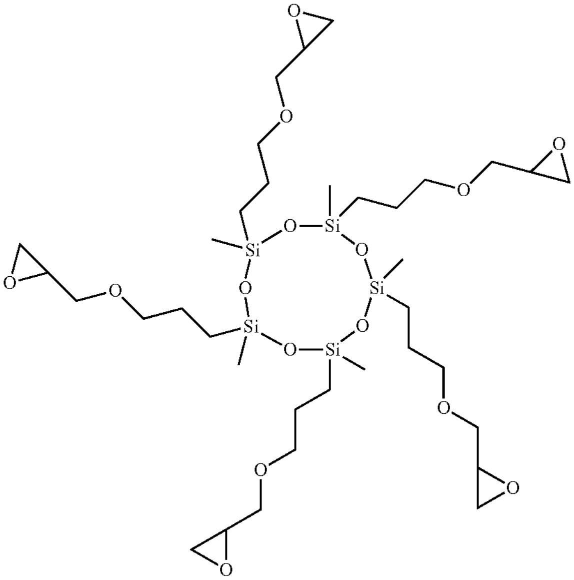

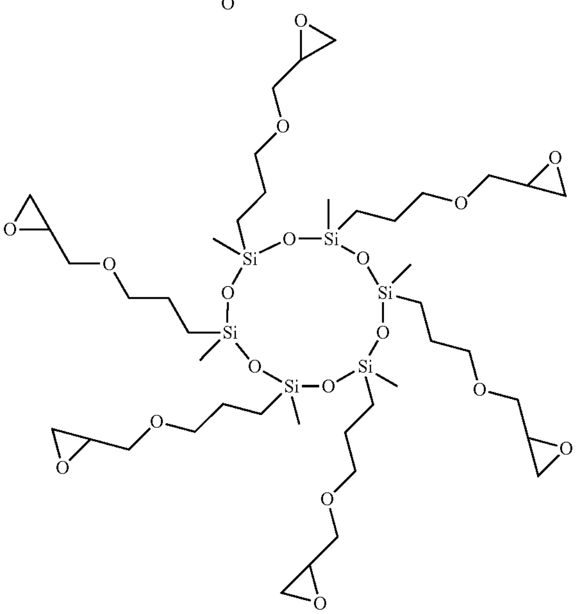

For ease of producing high refractive index materials from the photosensitive composition, the photosensitive composition preferably contains a compound of Formula (A-2e) below as the additional photopolymerizable compound (A2).

(A-2e)

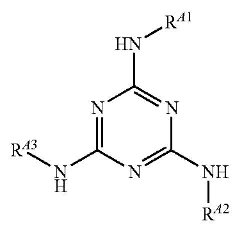

In Formula (A-2e), $R^{A1}$, $R^{A2}$, and $R^{A3}$ are each independently an organic group, and at least two selected from the group consisting of an organic group of $R^{A1}$, an organic group of $R^{A2}$, and an organic group of $R^{A3}$ each have a radically polymerizable group-containing group or a cationically polymerizable group-containing group.

Preferred examples of the compound of Formula (A-2e) include a compound of Formula (A-2e-a) below.

(A-2e-a)

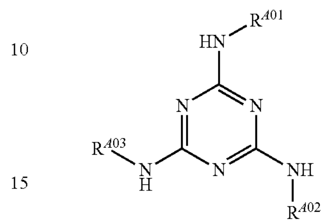

In Formula (A-2e-a), $R^{A01}$ is an optionally substituted quinolinyl group, an optionally substituted isoquinolinyl group, or an optionally substituted 2-substituted benzothiazolyl group, the 2-substituted benzothiazolyl group has, at position 2, a group represented by —S—$R^{A0}$, $R^{A0}$ is a hydrogen atom, a radically polymerizable group-containing group, or a cationically polymerizable group-containing group, $R^{A02}$ and $R^{A03}$ are both aromatic ring-containing groups having a radically polymerizable group-containing group or both aromatic ring-containing groups having a cationically polymerizable group-containing group, and the —NH— groups bonded to the triazine ring are bonded to the aromatic rings in $R^{A02}$ and $R^{A03}$, respectively.

The optionally substituted quinolinyl group, the optionally substituted isoquinolinyl group, and the optionally substituted 2-substituted benzothiazolyl group all have a relatively high polarizability and all have a functional group with a relatively small volume. Therefore, the optionally substituted, quinolinyl, isoquinolinyl, or 2-substituted benzothiazolyl group of $R^{A01}$ will contribute to the ability of the photosensitive composition to form a material with a high refractive index.

The quinolinyl group of $R^{A01}$ may be quinolin-2-yl, quinolin-3-yl, quinolin-4-yl, quinolin-5-yl, quinolin-6-yl, quinolin-7-yl, or quinolin-8-yl. In particular, the quinolinyl group of $R^{A01}$ is preferably quinolin-3-yl or quinolin-4-yl for ease of obtaining a raw material compound for the compound of Formula (A2e-a) or for ease of synthesizing the compound of Formula (A2e-a).

The isoquinolinyl group of $R^{A01}$ may be isoquinolin-1-yl, isoquinolin-3-yl, isoquinolin-4-yl, isoquinolin-5-yl, isoquinolin-6-yl, isoquinolin-7-yl, or isoquinolin-8-yl.

The quinolinyl group of $R^{A01}$ and the isoquinolinyl group of $R^{A01}$ may each have any substituent that does not compromise the desired effect. Examples of such a substituent include a halogen atom, a hydroxyl group, a mercapto group, a cyano group, a nitro group, and a monovalent organic group. Examples of the substituent halogen atom include fluorine, chlorine, bromine, and iodine. Examples of the monovalent organic group include alkyl, alkoxy, alkoxyalkyl, aliphatic acyl, aliphatic acyloxy, alkoxycarbonyl, alkylthio, and aliphatic acylthio. The monovalent organic group is also preferably a radically polymerizable group-containing group or a cationically polymerizable group-containing group, which will be described later.

The substituent monovalent organic group may have any number of carbon atoms as long as the desired effect will not be impaired. For example, the substituent monovalent organic group preferably has 1 or more and 20 or less carbon atoms, more preferably 1 or more and 12 or less carbon atoms, even more preferably 1 or more and 8 or less carbon atoms. The alkoxyalkyl group, the aliphatic acyl group, the aliphatic acyloxy group, the alkoxycarbonyl group, the alkoxyalkylthio group, or the aliphatic acylthio group should have at least two carbon atoms.

Preferred examples of the substituent alkyl group include methyl, ethyl, n-propyl, isopropyl, n-butyl, isobutyl, sec-butyl, tert-butyl, n-pentyl, n-hexyl, n-heptyl, and n-octyl.

Preferred examples of the substituent alkoxy group include methoxy, ethoxy, n-propyloxy, isopropyloxy, n-butyloxy, isobutyloxy, sec-butyloxy, tert-butyloxy, n-pentyloxy, n-hexyloxy, n-heptyloxy, and n-octyloxy.

Preferred examples of the substituent alkoxyalkyl group include methoxymethyl, ethoxymethyl, n-propyloxymethyl, n-butyloxymethyl, 2-methoxyethyl, 2-ethoxyethyl, 2-n-propyloxyethyl, 2-n-butyloxyethyl, 3-methoxy-n-propyloxy, 3-ethoxy-n-propyloxy, 3-n-propyloxy-n-propyloxy, 3-n-butyloxy-n-propyloxy, 4-methoxy-n-butyloxy, 4-ethoxy-n-butyloxy, 4-n-propyloxy-n-butyloxy, and 4-n-butyloxy-n-butyloxy.

Preferred examples of the substituent aliphatic acyl group include acetyl, propionyl, butanoyl, pentanoyl, hexanoyl, heptanoyl, and octanoyl.

Preferred examples of the substituent aliphatic acyloxy group include acetoxy, propionyloxy, butanoyloxy, pentanoyloxy, hexanoyloxy, heptanoyloxy, and octanoyloxy.

Preferred examples of the substituent alkoxycarbonyl group include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, n-hexyloxycarbonyl, n-heptyloxycarbonyl, and n-octyloxycarbonyl.

Preferred examples of the substituent alkylthio group include methylthio, ethylthio, n-propylthio, isopropylthio, n-butylthio, isobutylthio, sec-butylthio, tert-butylthio, n-pentylthio, n-hexylthio, n-heptylthio, and n-octylthio.

Preferred examples of the substituent aliphatic acylthio group include acetylthio, propionylthio, butanoylthio, pentanoylthio, hexanoylthio, heptanoylthio, and octanoylthio.

The quinolinyl or isoquinolinyl group may have any number of substituents as long as the desired effect will not be impaired. The quinolinyl or isoquinolinyl group preferably has one or more and four or less substituents, more preferably one or two substituents, and even more preferably one substituent. The quinolinyl or isoquinolinyl group may have two or more substituents different from one another.

The 2-substituted benzothiazolyl group of $R^{A01}$ has, at position 2, a group represented by —S—$R^{A0}$. The 2-substituted benzothiazolyl group of $R^{A01}$ may have a substituent other than the group represented by —S—$R^{A0}$ at a position other than position 2. $R^{A0}$ is a hydrogen atom, a radically polymerizable group-containing group, or a cationically polymerizable group-containing group. The radically polymerizable group-containing group and the cationically polymerizable group-containing group will be described later.

Preferred examples of the 2-substituted benzothiazolyl group include the groups shown below.

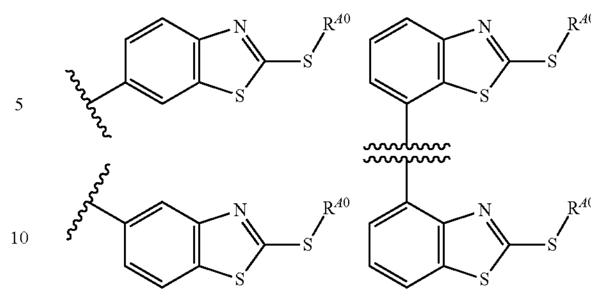

The 2-substituted benzothiazolyl group of $R^{A01}$ may have a substituent, examples of which are the same as those of the substituent that the quinolinyl or isoquinolinyl group may have. The 2-substituted benzothiazolyl group may have any number of substituents as long as the desired effect will not be impaired. The 2-substituted benzothiazolyl group preferably has one or two substituents, more preferably one substituent. The 2-substituted benzothiazolyl group may have two or more substituents different from one another.

$R^{A02}$ and $R^{A03}$ are both aromatic ring-containing groups having a radically polymerizable group-containing group or both aromatic ring-containing groups having a cationically polymerizable group-containing group. In this regard, the —NH— groups bonded to the triazine ring are bonded to the aromatic rings in $R^{A02}$ and $R^{A03}$, respectively. The aromatic ring-containing group of $R^{A02}$ or $R^{A03}$ may have a radically or cationically polymerizable group-containing group bonded at any position.

The aromatic ring-containing group of $R^{A02}$ may have any number of radically or cationically polymerizable group-containing groups. The aromatic ring-containing group of $R^{A03}$ may also have any number of radically or cationically polymerizable group-containing groups. The aromatic ring-containing group of $R^{A02}$ or $R^{A03}$ preferably has one, two, or three radically or cationically polymerizable group-containing groups, more preferably one or two radically or cationically polymerizable group-containing groups, even more preferably one radically or cationically polymerizable group-containing group.

The aromatic ring-containing group of $R^{A02}$ or $R^{A03}$ may have only one monocyclic aromatic ring or only one fused aromatic ring or may have two or more monocyclic aromatic rings and/or two or more fused aromatic rings. In a case where the aromatic ring-containing group of $R^{A02}$ or $R^{A03}$ has two or more monocyclic aromatic rings and/or two or more fused aromatic rings, any type of linking group may be used to link the monocyclic aromatic rings, to link the fused aromatic rings, or to link the monocyclic aromatic ring and the fused aromatic ring. The linking group may be divalent, trivalent, or polyvalent. Preferably, the linking group is divalent.

Examples of the divalent linking group include a divalent aliphatic hydrocarbon group, a divalent halogenated aliphatic hydrocarbon group, —CONH—, —NH—, —N═N—, —CH═N—, —COO—, —O—, —CO—, —SO—, —$SO_2$—, —S—, —S—S—, and a combination of two or more of these groups.

The divalent linking group is also preferably a group represented by —$CR^{a001}R^{a002}$—. $R^{a001}$ and $R^{a002}$ are each independently a hydrogen atom, an alkyl group having 1 or more and 4 or less carbon atoms, or a halogenated alkyl group having 1 or more and 4 or less carbon atoms. $R^{a001}$ and $R^{a002}$ may be bonded to each other to form a ring. Examples of the group represented by —$CR^{a001}R^{a002}$— include methylene, ethane-1,1-diyl, propane-2,2-diyl, butane-2,2-diyl, 1,1,1,3,3,3-hexafluoropropane-2,2-diyl, cyclopentylidene, cyclohexylidene, and cycloheptylidene.

The aromatic ring-containing group of $R^{A02}$ or $R^{A03}$ has a radically or cationically polymerizable group-containing group. The radically or cationically polymerizable group-containing group may be as mentioned above.

Preferred examples of the radically polymerizable group-containing group include groups of Formulae (A-I) and (A-II) below, excluding vinyloxy group-containing groups.

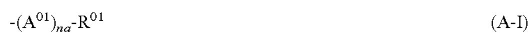
$$-(A^{01})_{na}-R^{01} \quad \text{(A-I)}$$

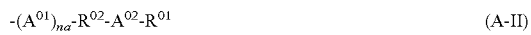
$$-(A^{01})_{na}-R^{02}-A^{02}-R^{01} \quad \text{(A-II)}$$

In Formulae (A-I) and (A-II), $R^{01}$ is an alkenyl group having 2 or more and 10 or less carbon atoms, $R^{02}$ is an alkylene group having 1 or more and 10 or less carbon atoms, $A^{01}$ is —O—, —S—, —CO—, —CO—O—, —CO—S—, —O—CO—, —S—CO—, —CO—NH—, —NH—CO—, or —NH—, $A^{02}$ is —O—, —S—, —CO—, —CO—C—, —CO—S—, —O—CO—, —S—CO—, —CO—NH—, —NH—CO—, or —NH—, and na is 0 or 1.

Preferred examples of the radically polymerizable group-containing group include the following groups:

—O—$R^{03}$,

—S—$R^{03}$,

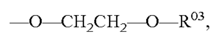
—O—$CH_2CH_2$—O—$R^{03}$,

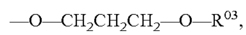
—O—$CH_2CH_2CH_2$—O—$R^{03}$,

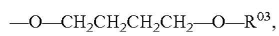
—O—$CH_2CH_2CH_2CH_2$—O—$R^{03}$,

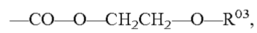
—CO—O—$CH_2CH_2$—O—$R^{03}$,

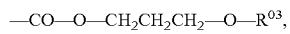
—CO—O—$CH_2CH_2CH_2$—O—$R^{03}$,

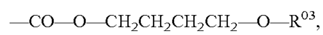
—CO—O—$CH_2CH_2CH_2CH_2$—O—$R^{03}$,

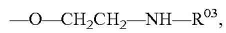
—O—$CH_2CH_2$—NH—$R^{03}$,

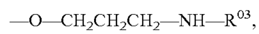
—O—$CH_2CH_2CH_2$—NH—$R^{03}$,

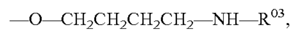
—O—$CH_2CH_2CH_2CH_2$—NH—$R^{03}$,

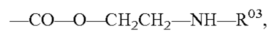
—CO—O—$CH_2CH_2$—NH—$R^{03}$,

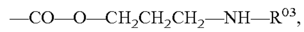
—CO—O—$CH_2CH_2CH_2$—NH—$R^{03}$,

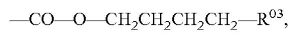
—CO—O—$CH_2CH_2CH_2CH_2$—$R^{03}$,

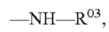
—NH—$R^{03}$,

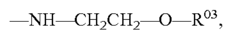
—NH—$CH_2CH_2$—O—$R^{03}$,

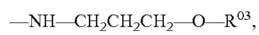
—NH—$CH_2CH_2CH_2$—O—$R^{03}$,

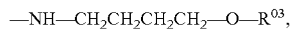
—NH—$CH_2CH_2CH_2CH_2$—O—$R^{03}$,

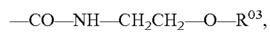
—CO—NH—$CH_2CH_2$—O—$R^{03}$,

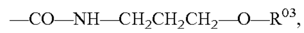
—CO—NH—$CH_2CH_2CH_2$—O—$R^{03}$,

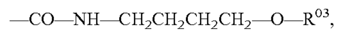
—CO—NH—$CH_2CH_2CH_2CH_2$—O—$R^{03}$,

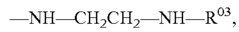
—NH—$CH_2CH_2$—NH—$R^{03}$,

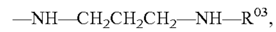
—NH—$CH_2CH_2CH_2$—NH—$R^{03}$,

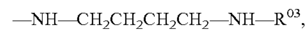
—NH—$CH_2CH_2CH_2CH_2$—NH—$R^{03}$,

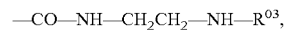
—CO—NH—$CH_2CH_2$—NH—$R^{03}$,

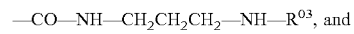
—CO—NH—$CH_2CH_2CH_2$—NH—$R^{03}$, and

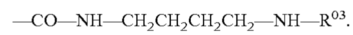
—CO—NH—$CH_2CH_2CH_2CH_2$—NH—$R^{03}$.

In these groups, $R^{03}$ is an allyl group or a (meth)acryloyl group.

Preferred examples of the cationically polymerizable group-containing group include a vinyloxy group and groups of Formulae (A3) to (A8) below.

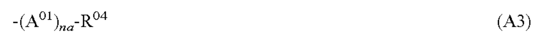
$$-(A^{01})_{na}-R^{04} \quad \text{(A3)}$$

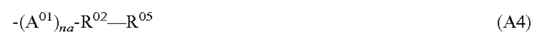
$$-(A^{01})_{na}-R^{02}-R^{05} \quad \text{(A4)}$$

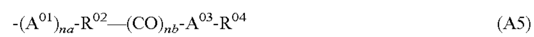
$$-(A^{01})_{na}-R^{02}-(CO)_{nb}-A^{03}-R^{04} \quad \text{(A5)}$$

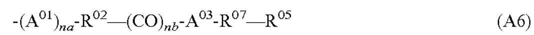
$$-(A^{01})_{na}-R^{02}-(CO)_{nb}-A^{03}-R^{07}-R^{05} \quad \text{(A6)}$$

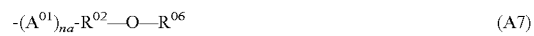
$$-(A^{01})_{na}-R^{02}-O-R^{06} \quad \text{(A7)}$$

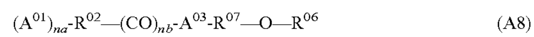
$$(A^{01})_{na}-R^{02}-(CO)_{nb}-A^{03}-R^{07}-O-R^{06} \quad \text{(A8)}$$

In Formulae (A3) to (A8), $R^{02}$ is an alkylene group having 1 or more and 10 or less carbon atoms, $R^{04}$ is an epoxyalkyl group having 2 or more and 20 or less carbon atoms or an alicyclic epoxy group having 3 or more and 20 or less carbon atoms, $R^{05}$ is an alicyclic epoxy group having 3 or more and 20 or less carbon atoms, $R^{06}$ is a vinyl group, $R^{07}$ is an alkylene group having 1 or more and 10 or less carbon atoms, $A^{01}$ is —O—, —S—, —CO—, —CO—O—, —CO—S—, —O—CO—, —S—CO—, —CO—NH—, —NH—CO—, or —NH—, $A^{03}$ is —O— or —NH—, and nb is 0 or 1.

Preferred examples of the cationically polymerizable group-containing group include groups represented by the following:

—$R^{08}$,

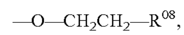
—O—$CH_2CH_2$—$R^{08}$,

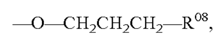
—O—$CH_2CH_2CH_2$—$R^{08}$,

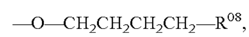
—O—$CH_2CH_2CH_2CH_2$—$R^{08}$,

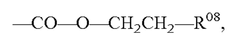
—CO—O—$CH_2CH_2$—$R^{08}$,

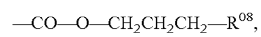
—CO—O—$CH_2CH_2CH_2$—$R^{08}$,

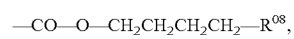
—CO—O—$CH_2CH_2CH_2CH_2$—$R^{08}$,

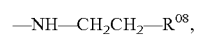
—NH—$CH_2CH_2$—$R^{08}$,

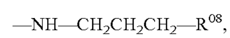
—NH—$CH_2CH_2CH_2$—$R^{08}$,

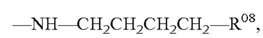
—NH—$CH_2CH_2CH_2CH_2$—$R^{08}$,

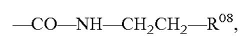
—CO—NH—$CH_2CH_2$—$R^{08}$,

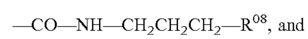
—CO—NH—$CH_2CH_2CH_2$—$R^{08}$, and

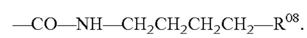
—CO—NH—$CH_2CH_2CH_2CH_2$—$R^{08}$.

In these groups, $R^{08}$ is a vinyloxy group, a glycidyloxy group, a glycidylthio group, an epoxycyclopentyl group, an epoxycyclohexyl group, or an epoxycycloheptyl group.

In a case where the aromatic ring-containing group of $R^{A402}$ or $R^{A403}$ has a single radically or cationically polymerizable group-containing group, preferred examples of $R^{A402}$ or $R^{A403}$ include groups of the formulae shown below. In the formulae below, PG is a radically or cationically polymerizable group-containing group.

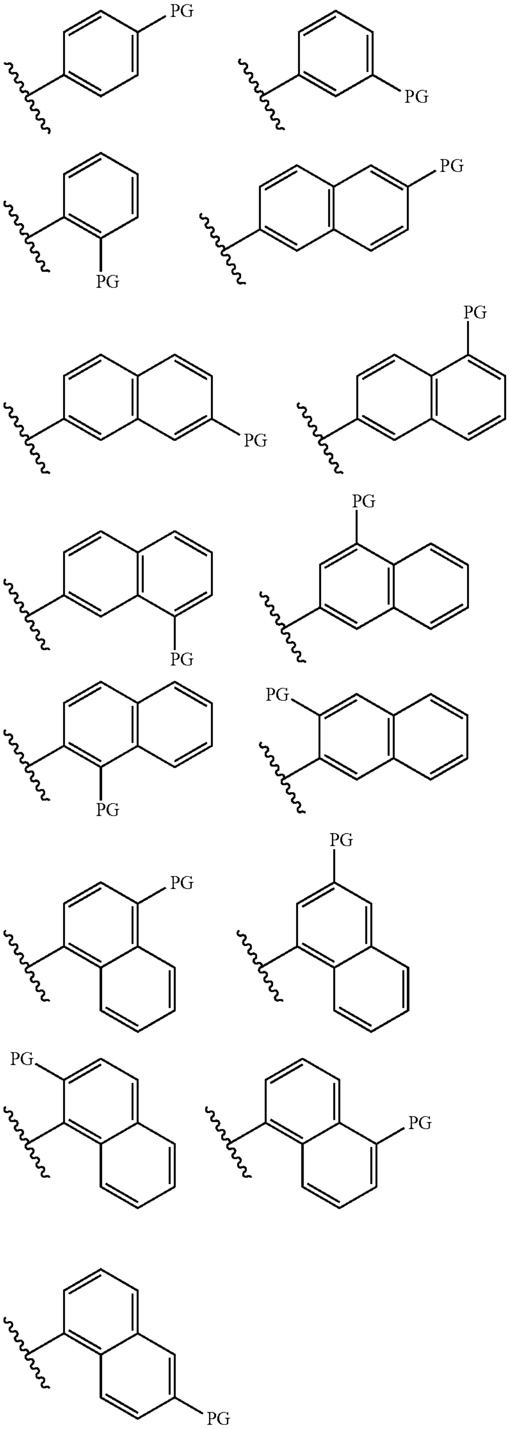

-continued

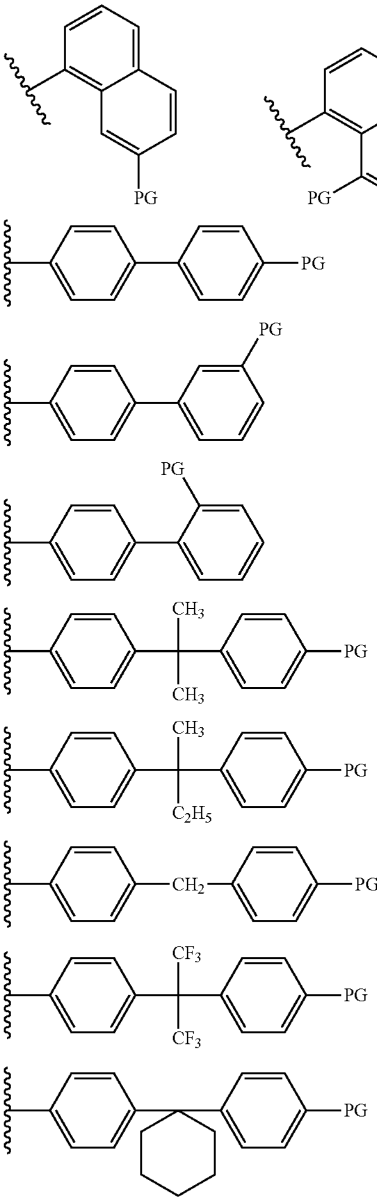

Preferred examples of the compound of Formula (A-2e) include compounds of the formulae shown below. In the formulae below, $X^A$ is a group selected from the group consisting of a (meth)acryloyloxy group, a (meth)acryloylthio group, a 3-(meth)acryloyloxy-2-hydroxy-n-propyloxycarbonyl group, and a glycidyloxy group.

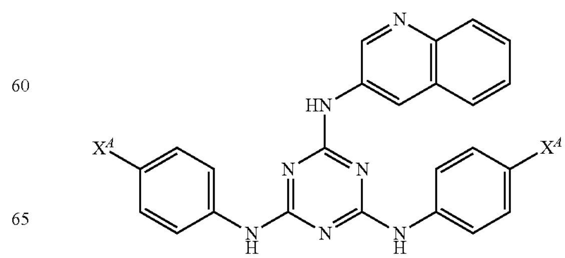

-continued
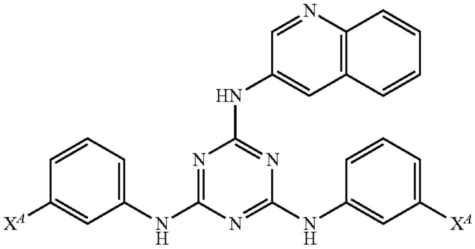
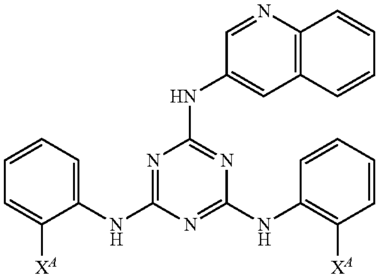
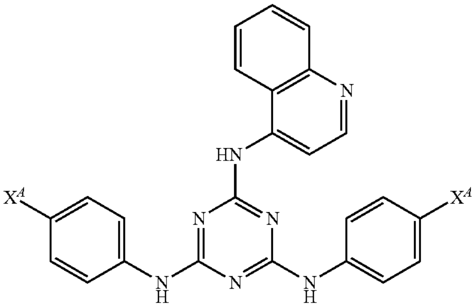
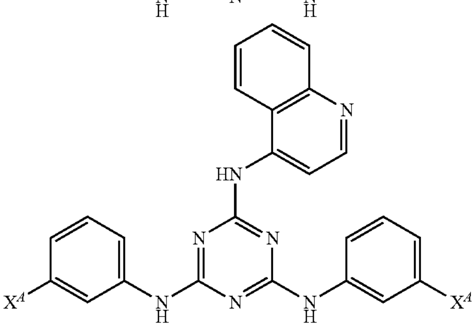
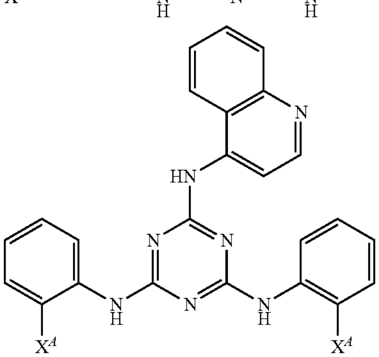
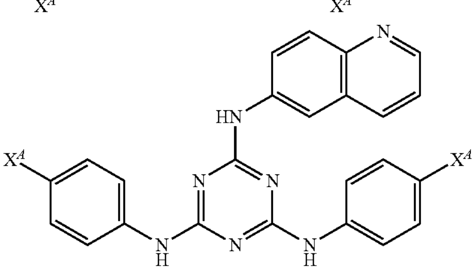
-continued
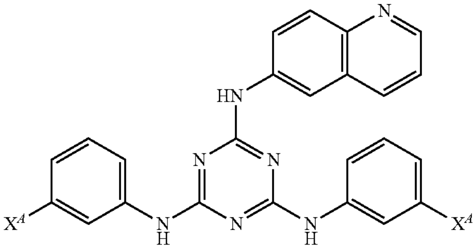
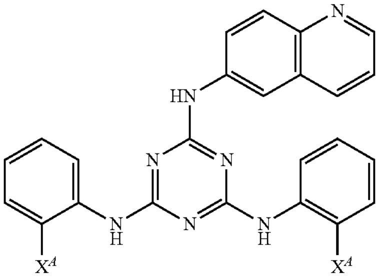
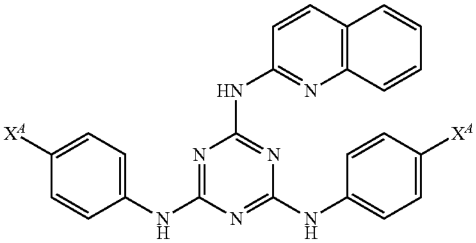
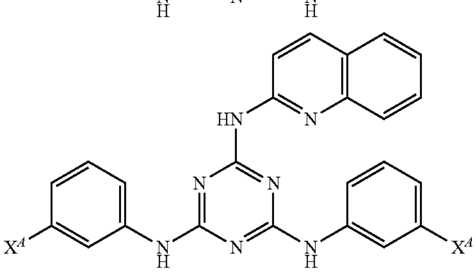
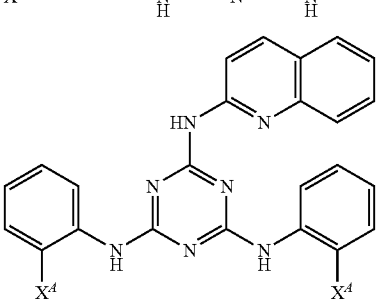
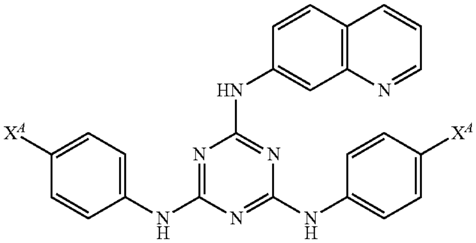

-continued
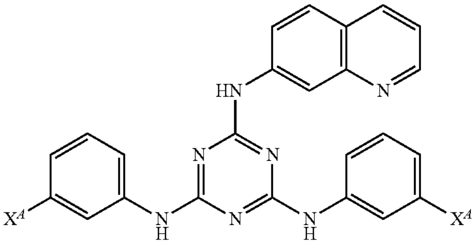
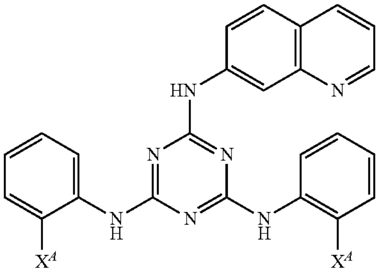
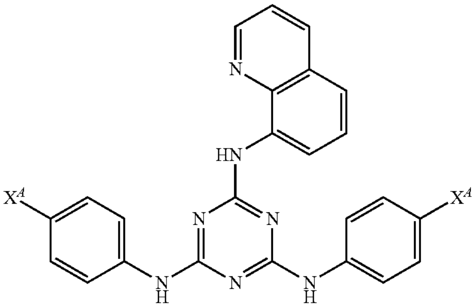
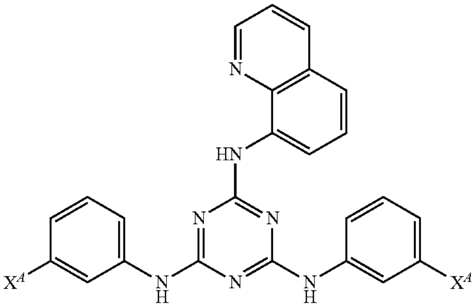
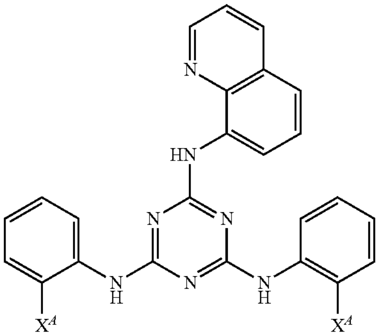
-continued
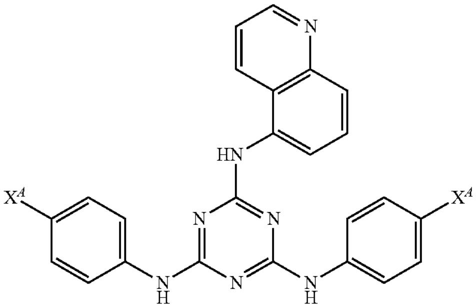
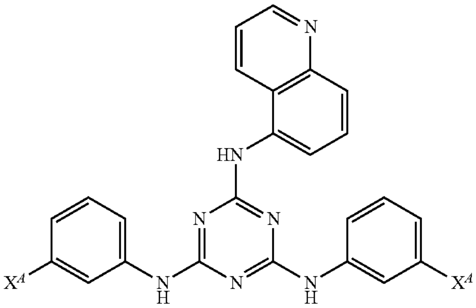
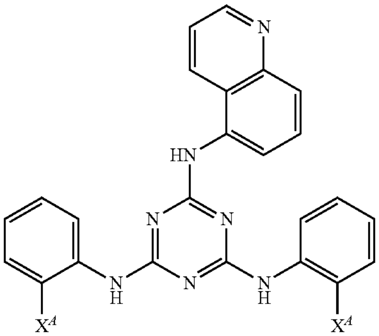
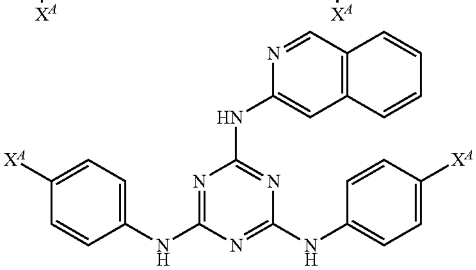
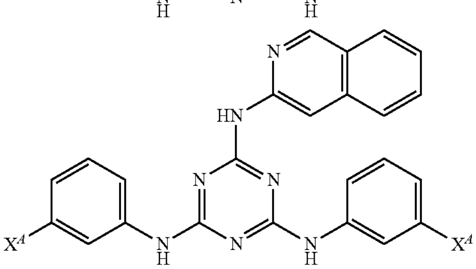
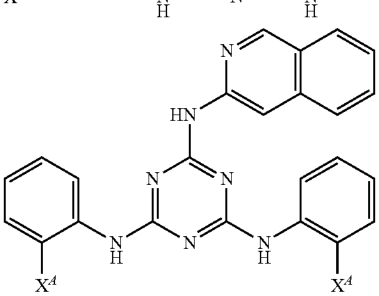

-continued
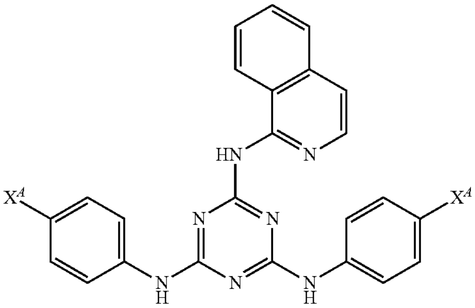
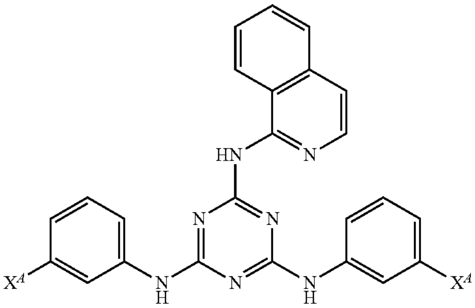
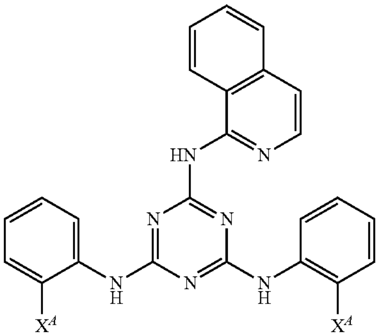
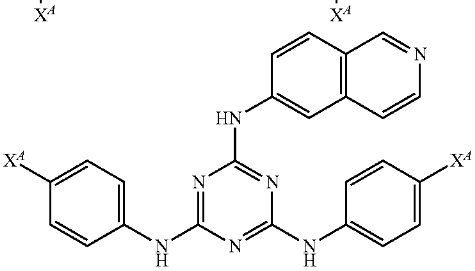
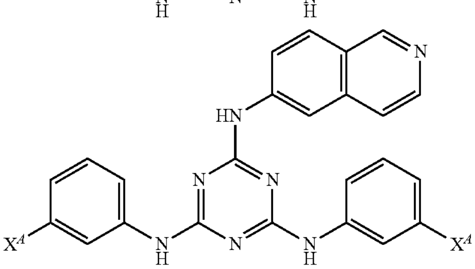
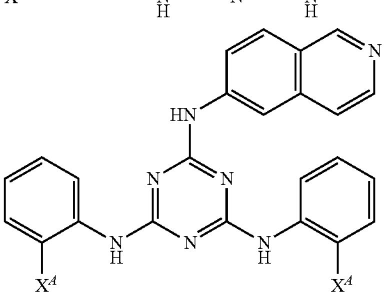
-continued
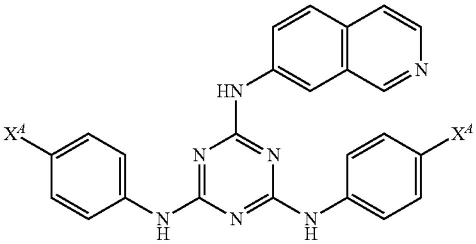
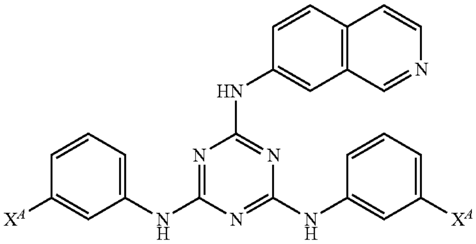
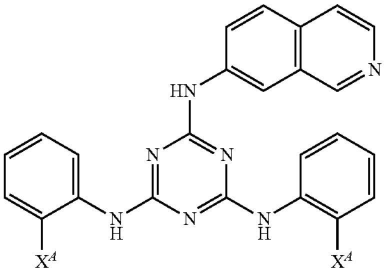
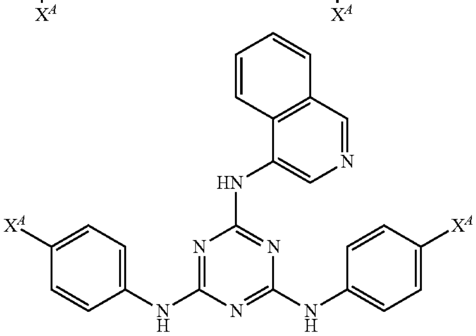
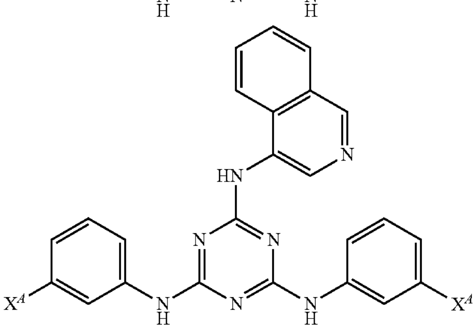
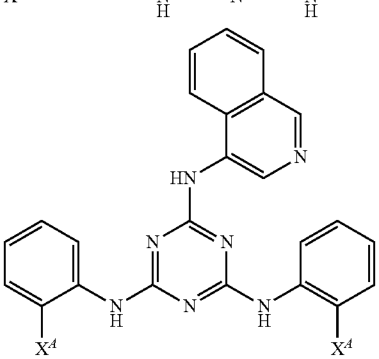

-continued
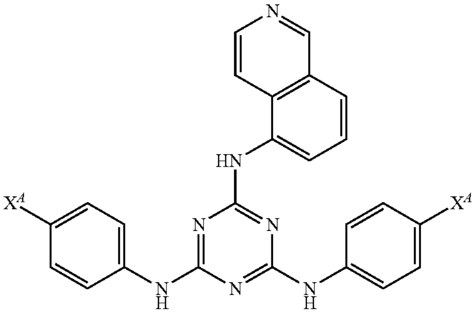
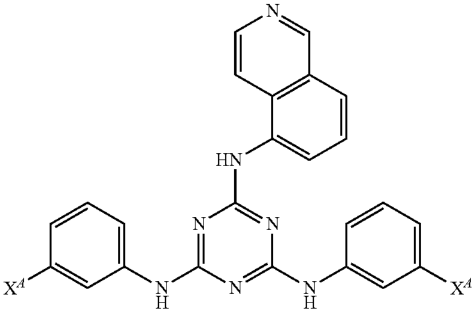
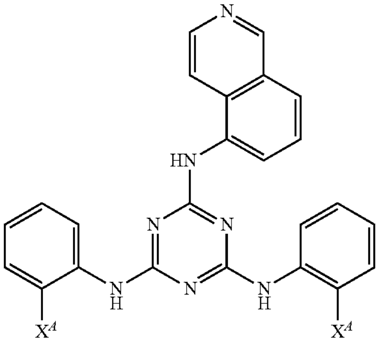
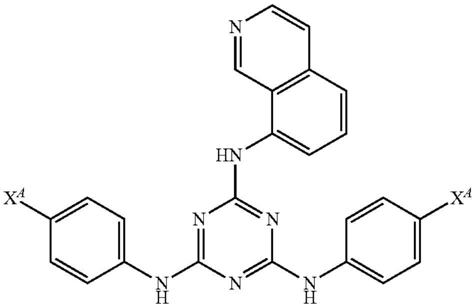
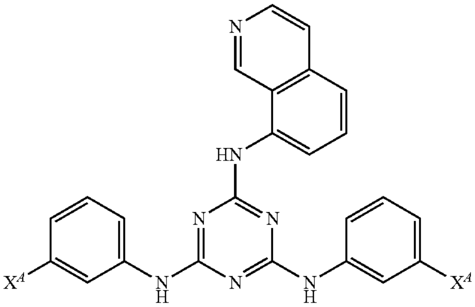
-continued
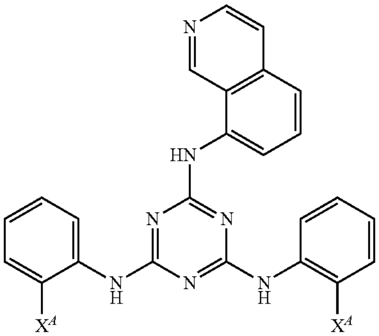
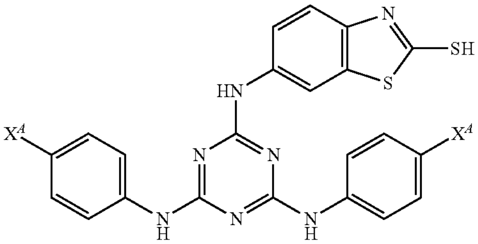
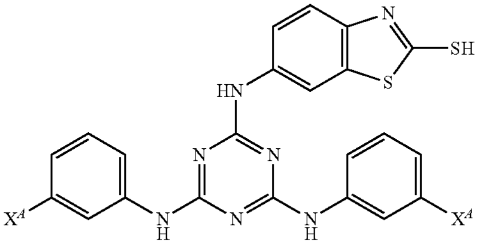
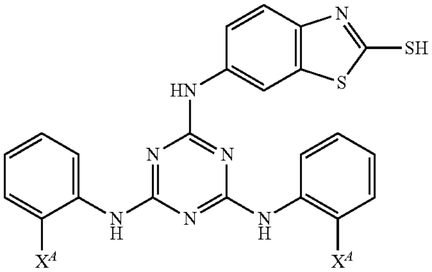
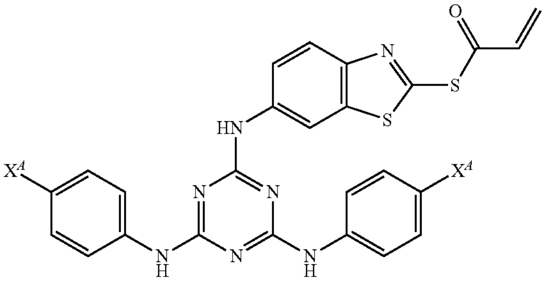
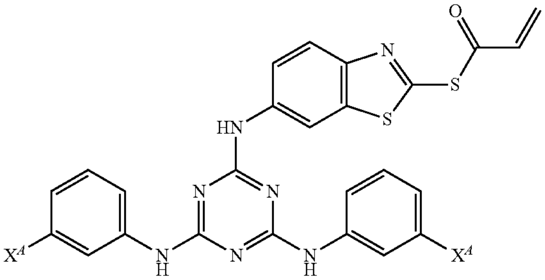

-continued

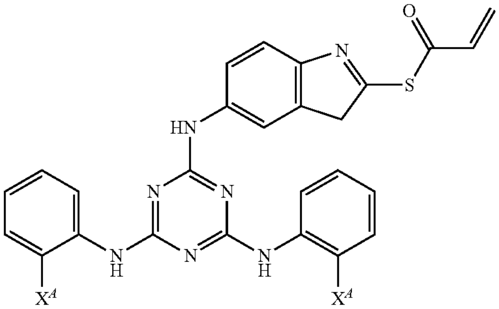

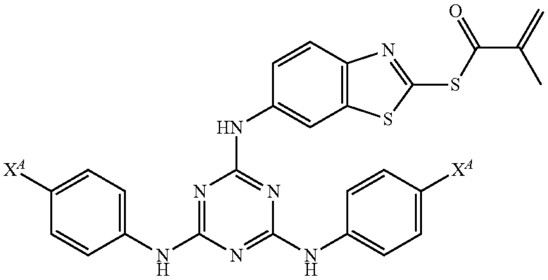

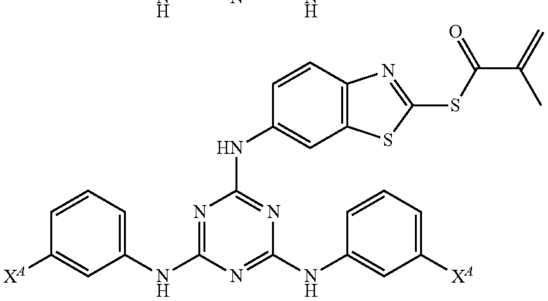

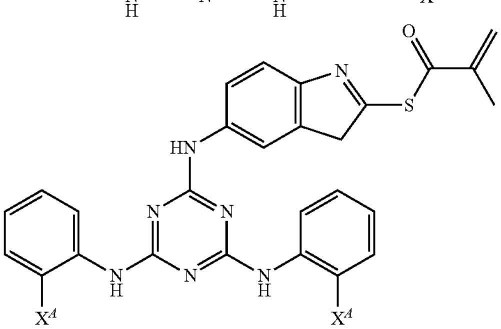

The compound of Formula (A-2e-a) may be produced by any suitable method. Typically, the compound of Formula (A-2e-a) may be produced by allowing a cyanuric halide, such as cyanuric chloride, to react with aromatic amines represented by $R^{A01}$—$NH_2$, $R^{A02}$—$NH_2$, and $R^{A03}$—$NH_2$. These amines may be allowed to react simultaneously or sequentially with the cyanuric halide. Preferably, these amines are allowed to react sequentially with the cyanuric halide.

$R^{A02}$ or $R^{A03}$ in Formula (A-2e-a) may be formed by a process including: allowing the cyanuric halide to react with an aromatic amine having a functional group, such as hydroxyl, mercapto, carboxy, or amino; and then allowing the functional group to react with a compound for forming a radically or cationically polymerizable group-containing group. The compound for forming a radically or cationically polymerizable group-containing group may be a polymerizable group-containing compound, such as (meth)acrylic acid, (meth)acrylic acid halide, halogenated olefin, epichlorohydrin, or glycidyl (meth)acrylate. The reaction of the functional group, such as hydroxyl, mercapto, carboxy, or amino, with the polymerizable group-containing compound may be a well-known reaction for forming an ether bond, a carboxylic acid ester bond, a carboxylic acid amide bond, or a thioether bond.

The reaction for forming the radically or cationically polymerizable group-containing group may be a multi-stage reaction. For example, a radically polymerizable group-containing group of the formula below may be introduced onto an aromatic ring by a process including: allowing the cyanuric halide to react with an aromatic amine having a phenolic hydroxyl group; then allowing the phenolic hydroxyl group to react with epichlorohydrin to form a glycidyl group; and then allowing acrylic acid to react with the glycidyl group.

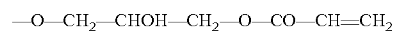

$$—O—CH_2—CHOH—CH_2—O—CO—CH{=}CH_2$$

The above reaction is a mere example, and the radically or cationically polymerizable group-containing group may be formed by any suitable combination of various reactions.

The compound of Formula (A-2e-a) is usually synthesized in an organic solvent. Such an organic solvent may be any inert solvent that does not react with the cyanuric halide, the aromatic amines, the radically polymerizable group, or the cationically polymerizable group. Such a solvent may be any of organic solvent examples listed for the solvent (S) described later. For the production of the compound of Formula (A-2e-a), the cyanuric halide may be allowed to react at any suitable temperature with aromatic amines, such as the aromatic amines represented by $R^{A01}$—$NH_2$, $R^{A02}$—$NH_2$, and $R^{A03}$—$NH_2$. Typically, the reaction temperature is preferably 0° C. or more and 150° C. or less.

Other preferred examples of the compound of Formula (A-2e) include compounds of Formula (A-2e-b) below.

(A-2e-b)

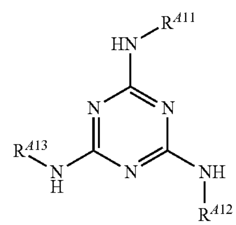

In Formula (A-2e-b), $R^{A11}$, $R^{A12}$, and $R^{A13}$ are each an aromatic ring-containing group, and at least one of $R^{A12}$ or $R^{A13}$ is a group of Formula (A-2e-b1) below.

(A-2e-b1)

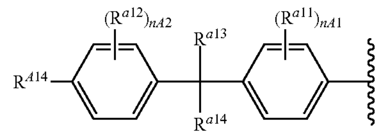

The —NH— groups bonded to the triazine ring are bonded to the aromatic rings in $R^{A11}$, $R^{A12}$, and $R^{A13}$, respectively. In Formula (A-2e-b1), $R^{a11}$ and $R^{a12}$ are each independently an alkyl group having 1 or more and 4 or less carbon atoms, an alkoxy group having 1 or more and 4 or less carbon atoms, or a halogen atom, nA1 and nA2 are each independently an integer of 0 or more and 4 or less, $R^{a13}$ and $R^{a14}$ are each independently a hydrogen atom, an alkyl group having 1 or more and 4 or less carbon atoms, a halogenated alkyl group having 1 or more and 4 or less carbon atoms, or a phenyl group, $R^{a13}$ and $R^{a14}$ may be bonded to each other to form a ring, $R^{a14}$ is a radically polymerizable group-containing group or a cationically polymerizable group-containing group, and when $R^{A12}$ and $R^{A13}$ are both groups of Formula (A-2e-b1), $R^{A12}$ and $R^{A13}$ both have radically polymerizable group-containing groups or cationically polymerizable group-containing groups.

As defined above, in Formula (A-2e-b), $R^{A11}$, $R^{A12}$, and $R^{A13}$ are each an aromatic ring-containing group. In Formula (A-2e-b), the —NH— groups bonded to the triazine ring are bonded to the aromatic rings in $R^{A11}$, $R^{A12}$, and $R^{A13}$, respectively. When the aromatic ring-containing group is a group other than the group of Formula (A-2e-b1), the aromatic ring-containing group may be any type satisfying the requirements specified above.

Such an aromatic ring-containing group other than the group of Formula (A-2e-b1) may have only one monocyclic aromatic ring or only one fused aromatic ring or may have two or more monocyclic aromatic rings and/or two or more fused aromatic rings. In a case where the aromatic ring-containing group has two or more monocyclic aromatic rings and/or two or more fused aromatic rings, any linking group may be used to link the monocyclic aromatic rings, to link the fused aromatic rings, or to link the monocyclic aromatic ring and the fused aromatic ring. The linking group may be divalent, trivalent, or polyvalent. Preferably, the linking group is divalent.

Examples of the divalent linking group include a divalent aliphatic hydrocarbon group, a divalent halogenated aliphatic hydrocarbon group, —CONH—, —NH—, —N═N—, —CH═N—, —COO—, —O—, —CO—, —SO—, $—SO_2—$, —S—, —S—S—, and any combination of two or more of these groups.

Preferred examples of the aromatic ring-containing group include an optionally substituted quinolinyl group, an optionally substituted isoquinolinyl group, and an optionally substituted 2-substituted benzothiazolyl group. Examples of these groups are the same as those of the optionally substituted quinolinyl, isoquinolinyl, and 2-substituted benzothiazolyl groups described for $R^{A01}$ in Formula (A-2e-a).

Other preferred examples of the aromatic ring-containing group include optionally substituted phenyl, optionally substituted naphthyl, optionally substituted biphenylyl, optionally substituted phenylthiophenyl, optionally substituted phenoxyphenyl, optionally substituted phenylsulfonylphenyl, optionally substituted benzothiazolyl, optionally substituted benzoxazolyl, and optionally substituted terphenyl. Examples of the optional substituent of these groups are the same as those of the substituent that the quinolinyl or isoquinolinyl group may have. These groups may have two or more substituents different from one another.

Preferred examples of the optionally substituted phenyl group include phenyl, 4-cyanophenyl, 3-cyanophenyl, 2-cyanophenyl, 2,3-dicyanophenyl, 2,4-dicyanophenyl, 2,5-dicyanophenyl, 2,6-dicyanophenyl, 3,4-dicyanophenyl, 3,5-dicyanophenyl, 4-nitrophenyl, 3-nitrophenyl, 2-nitrophenyl, 4-chlorophenyl, 3-chlorophenyl, 2-chlorophenyl, 4-bromophenyl, 3-bromophenyl, 2-bromophenyl, 4-iodophenyl, 3-iodophenyl, 2-iodophenyl, 4-methoxyphenyl, 3-methoxyphenyl, 2-methoxyphenyl, 4-methylphenyl, 3-methylphenyl, and 2-methylphenyl.

Preferred examples of the optionally substituted naphthyl group include naphthalen-1-yl and naphthalen-2-yl.

Preferred examples of the optionally substituted biphenylyl group include 4-phenylphenyl, 3-phenylphenyl, 2-phenylphenyl, 4-(4-nitrophenyl)phenyl, 3-(4-nitrophenyl)phenyl, 2-(4-nitrophenyl)phenyl, 4-(4-cyanophenyl)phenyl, 3-(4-cyanophenyl)phenyl, and 2-(4-cyanophenyl)phenyl.

Preferred examples of the optionally substituted phenylthiophenyl group include 4-phenylthiophenyl, 3-phenylthiophenyl, and 2-phenylthiophenyl.

Preferred examples of the optionally substituted phenoxyphenyl group include 4-phenoxyphenyl, 3-phenoxyphenyl, and 2-phenoxyphenyl.

Preferred examples of the optionally substituted phenylsulfonylphenyl group include 4-phenylsulfonylphenyl, 3-phenylsulfonylphenyl, and 2-phenylsulfonylphenyl.

Preferred examples of the optionally substituted benzothiazolyl group include benzothiazol-2-yl, benzothiazol-4-yl, benzothiazol-5-yl, benzothiazol-6-yl, and benzothiazol-7-yl.

Preferred examples of the optionally substituted benzoxazolyl group include benzoxazol-2-yl, benzoxazol-4-yl, benzoxazol-5-yl, benzoxazol-6-yl, and benzoxazol-7-yl.

Preferred examples of the optionally substituted terphenyl group include 4-(4-phenylphenyl)phenyl, 3-(4-phenylphenyl)phenyl, 2-(4-phenylphenyl)phenyl, 4-(3-phenylphenyl)phenyl, 3-(3-phenylphenyl)phenyl, 2-(3-phenylphenyl)phenyl, 4-(2-phenylphenyl)phenyl, 3-(2-phenylphenyl)phenyl, and 2-(2-phenylphenyl)phenyl.

As mentioned above, the aromatic ring-containing group other than the group of Formula (A-2e-b1) may have a radically or cationically polymerizable group-containing group as a substituent. The aromatic ring-containing group may have a radically or cationically polymerizable group-containing group bonded at any position.

The aromatic ring-containing group may have any number of radically or cationically polymerizable group-containing groups. The aromatic ring-containing group preferably has one, two, or three radically or cationically polymerizable group-containing groups, more preferably one or two radically or cationically polymerizable group-containing groups, even more preferably one radically or cationically polymerizable group-containing group.

Preferred examples of the aromatic ring-containing group having one radically or cationically polymerizable group-containing group include groups of the formulae shown below. In the formulae below, PG is a radically polymerizable group-containing group or a cationically polymerizable group-containing group.

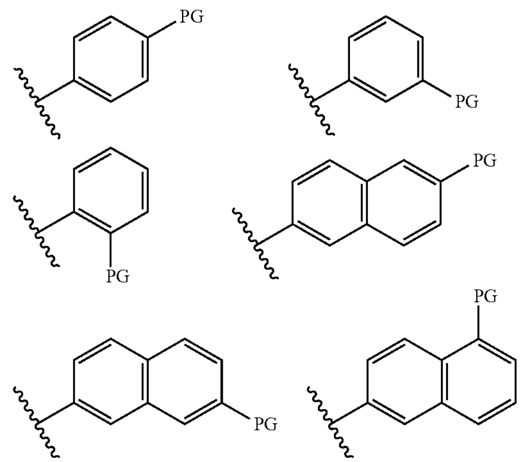

-continued

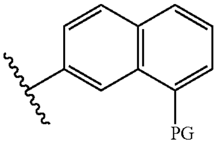
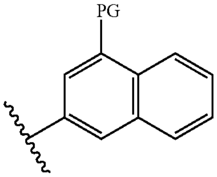
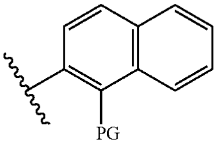
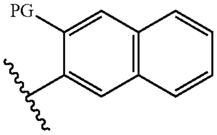
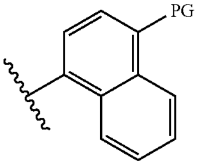
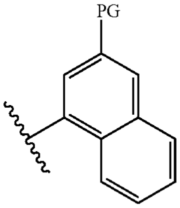
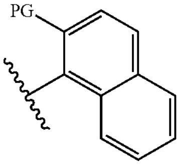
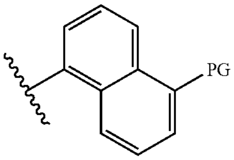
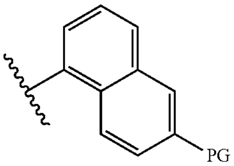
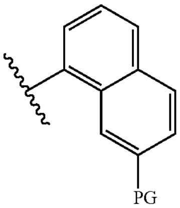
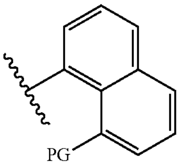
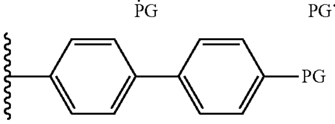
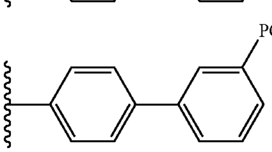
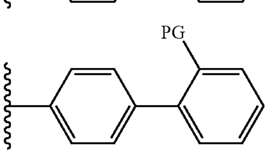
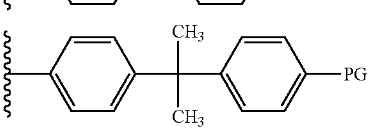
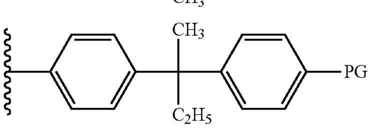

-continued

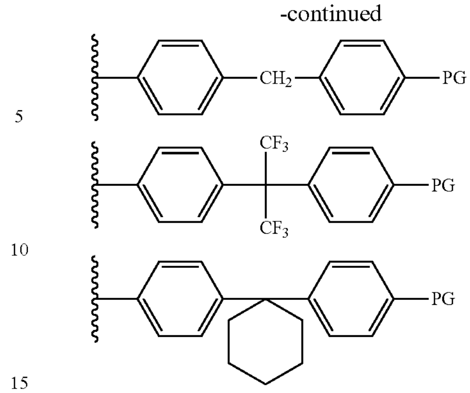

In Formula (A-2e-b), at least one of $R^{A12}$ or $R^{A13}$ is a group of Formula (A-2e-b1):

(A-2e-b1)

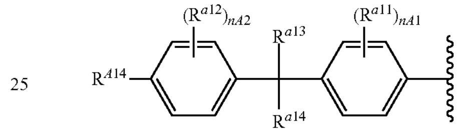

In Formula (A-2e-b1), $R^{a11}$ and $R^{a12}$ are each independently an alkyl group having 1 or more and 4 or less carbon atoms, an alkoxy group having 1 or more and 4 or less carbon atoms, or a halogen atom, nA1 and nA2 are each independently an integer of 0 or more and 4 or less, $R^{a13}$ and $R^{a14}$ are each independently a hydrogen atom, an alkyl group having 1 or more and 4 or less carbon atoms, a halogenated alkyl group having 1 or more and 4 or less carbon atoms, or a phenyl group, $R^{a13}$ and $R^{a14}$ may be bonded to each other to form a ring, $R^{A14}$ is a radically polymerizable group-containing group or a cationically polymerizable group-containing group, and when $R^{A12}$ and $R^{A13}$ are both groups of Formula (A-2e-b1), $R^{A12}$ and $R^{A13}$ both have radically polymerizable group-containing groups or cationically polymerizable group-containing groups.

The alkyl group of $R^{a11}$ or $R^{a12}$ having 1 or more and 4 or less carbon atoms may be methyl, ethyl, n-propyl, isopropyl, n-butyl, isobutyl, sec-butyl, or tert-butyl. The alkoxy group of $R^{a11}$ or $R^{a12}$ having 1 or more and 4 or less carbon atoms may be methoxy, ethoxy, n-propyloxy, isopropyloxy, n-butyloxy, isobutyloxy, sec-butyloxy, or tert-butyloxy. The halogen atom of $R^{a11}$ or $R^{a12}$ may be fluorine, chlorine, bromine, or iodine.

Examples of the alkyl group of $R^{a13}$ or $R^{a14}$ having 1 or more and 4 or less carbon atoms are the same as those of the alkyl group of $R^{a11}$ or $R^{a12}$ having 1 or more and 4 or less carbon atoms. Examples of the halogenated alkyl group of $R^{a13}$ or $R^{a14}$ having 1 or more and 4 or less carbon atoms include chloromethyl, dichloromethyl, trichloromethyl, bromomethyl, dibromomethyl, tribromomethyl, fluoromethyl, difluoromethyl, trifluoromethyl, 3,3,3-trifluoroethyl, pentafluoroethyl, and heptafluoropropyl.

Preferred examples of the group of Formula (A-2e-b1) include groups of the formulae shown below.

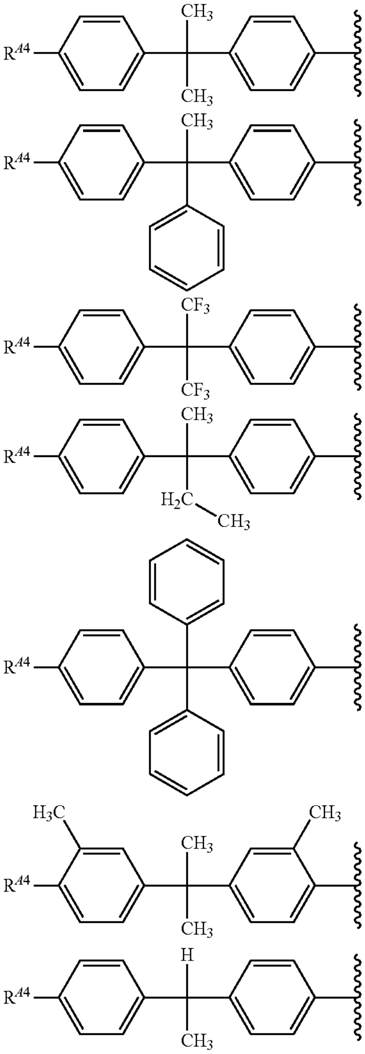

-continued

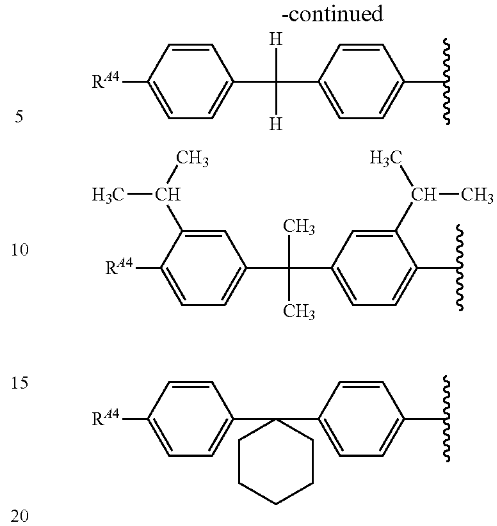

The group of Formula (A-2e-b1) has a radically or cationically polymerizable group-containing group represented by $R^{A14}$. The radically or cationically polymerizable group-containing group is as described above. Preferred examples of the radically polymerizable group-containing group and preferred examples of the cationically polymerizable group-containing group are the same as those shown for the compound of Formula (A-2e-a).

Preferred examples of the compound of Formula (A-2e-b) include compounds of the formulae shown below. In the formulae below, $X^A$ is a group selected from the group consisting of (meth)acryloyloxy, (meth)acryloylthio, 3-(meth)acryloyloxy-2-hydroxy-n-propyloxycarbonyl, and glycidyloxy, and $Y^A$ is a group selected from the group consisting of quinolin-3-yl, phenyl, 4-cyanophenyl, 3-cyanophenyl, 2-cyanophenyl, 3,4-dicyanophenyl, 4-nitrophenyl, 4-methoxyphenyl, 4-phenylthiophenyl, 4-phenylsulfonylphenyl, 4-iodophenyl, benzothiazol-2-yl, 2-mercaptobenzothiazol-5-yl, 4-phenylphenyl, 4-(4-nitrophenyl)phenyl, 4-(4-cyanophenyl)phenyl, naphthalen-1-yl, and 4-(4-phenylphenyl)phenyl.

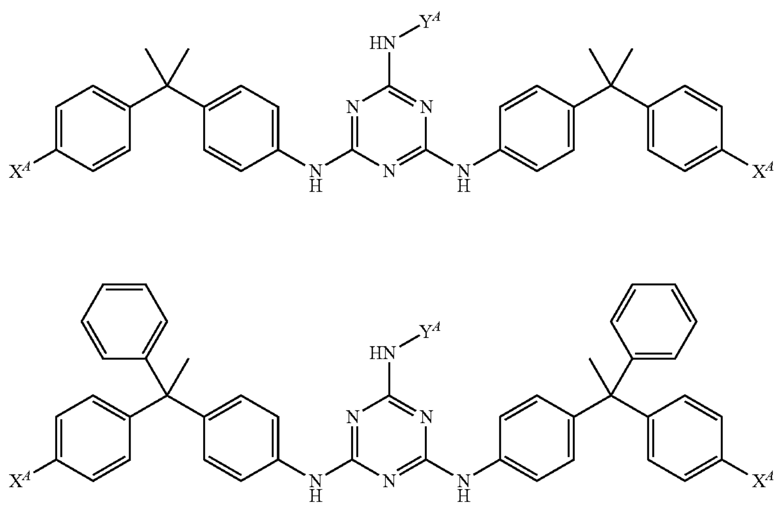

-continued
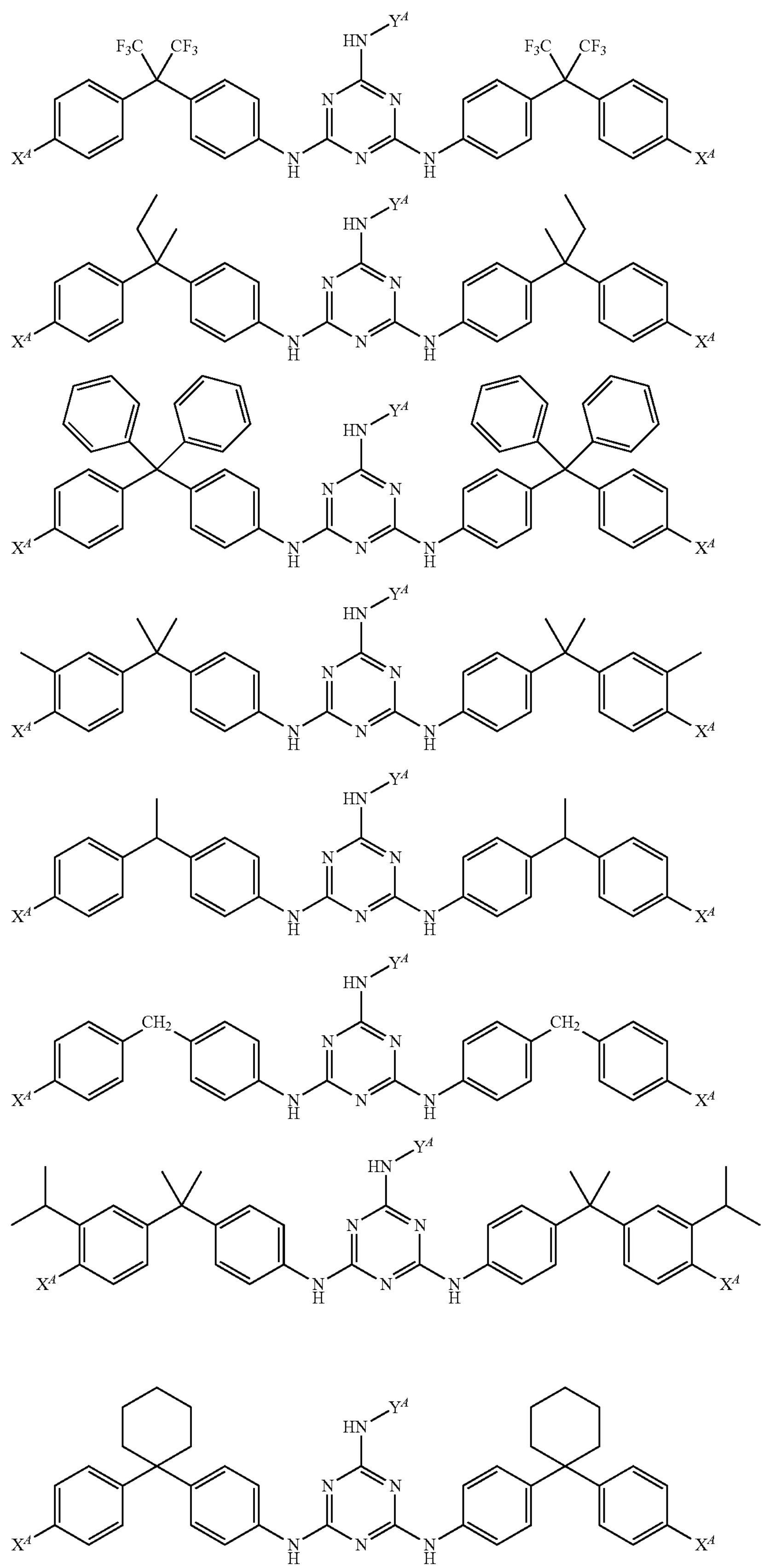

-continued

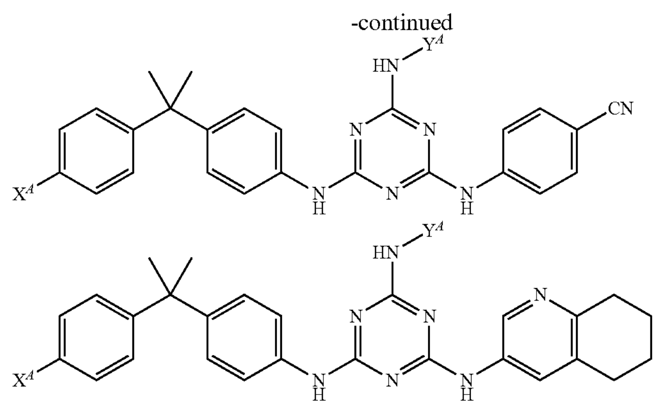

The compound of Formula (A-2e-b) may be produced by any suitable method. Typically, the compound of Formula (A-2e-b) may be produced by allowing a cyanuric halide, such as cyanuric chloride, to react with aromatic amines represented by $R^{A11}$—$NH_2$, $R^{A12}$—$NH_2$, and $R^{A13}$—$NH_2$. These amines may be allowed to react simultaneously or sequentially with the cyanuric halide. Preferably, these amines are allowed to react sequentially with the cyanuric halide.

The aromatic ring-containing group bonded to the triazine ring via —NH— may have a radically or cationically polymerizable group-containing group. Such a radically or cationically polymerizable group-containing group may be formed by a process including: allowing the cyanuric halide to react with an aromatic amine having a functional group, such as hydroxyl, mercapto, carboxy, or amino; and then allowing the functional group to react with a compound for forming a radically or cationically polymerizable group-containing group. The compound for forming a radically or cationically polymerizable group-containing group may be a polymerizable group-containing compound, such as (meth)acrylic acid, (meth)acrylic acid halide, halogenated olefin, epichlorohydrin, or glycidyl (meth)acrylate. The reaction of the functional group, such as hydroxyl, mercapto, carboxy, or amino, with the polymerizable group-containing compound may be a well-known reaction for forming an ether bond, a carboxylic acid ester bond, a carboxylic acid amide bond, or a thioether bond.

The reaction for forming the radically or cationically polymerizable group-containing group may be a multi-stage reaction. For example, a radically polymerizable group-containing group of the formula below may be introduced onto an aromatic ring by a process including: allowing the cyanuric halide to react with an aromatic amine having a phenolic hydroxyl group; then allowing the phenolic hydroxyl group to react with epichlorohydrin to form a glycidyl group; and then allowing acrylic acid to react with the glycidyl group.

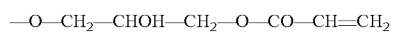

$$—O—CH_2—CHOH—CH_2—O—CO—CH{=}CH_2$$

The above reaction is a mere example, and the radically or cationically polymerizable group-containing group may be formed by any suitable combination of various reactions.

The compound of Formula (A-2e-b) is usually synthesized in an organic solvent. Such an organic solvent may be any inert solvent that does not react with the cyanuric halide, the aromatic amines, the radically polymerizable group, or the cationically polymerizable group. Such a solvent may be any of organic solvent examples listed for the solvent (S). For the production of the compound of Formula (A-2e-b), the cyanuric halide may be allowed to react at any suitable temperature with aromatic amines, such as the aromatic amines represented by $R^{A11}$—$NH_2$, $R^{A12}$—$NH_2$, and $R^{A13}$—$NH_2$. Typically, the reaction temperature is preferably 0° C. or more and 150° C. or less.

In the photosensitive composition, the ratio of the mass of the additional photopolymerizable compound(s) (A2) to the mass of the photopolymerizable compounds (A) is preferably 10 mass % or more and 90 mass % or less, more preferably 20 mass % or more and 80 mass % or less, even more preferably 30 mass % or more and 70 mass % or less, furthermore preferably 40 mass % or more and 60 mass % or less.

The content of the photopolymerizable compounds (A) in the photosensitive composition may be any level as long as the desired effect will not be impaired. The content of the photopolymerizable compounds (A) in the photosensitive composition is preferably 0.1 parts by mass or more and 50 parts by mass or less, more preferably 0.5 parts by mass or more and 40 parts by mass or less, even more preferably 1 part by mass or more and 25 parts by mass or less, based on the mass calculated by subtracting the mass of the solvent (S) described later from the mass of the photosensitive composition, which corresponds to 100 parts by mass.

Inorganic Fine Particles (B)

The photosensitive composition may contain inorganic fine particles (B). The inorganic fine particles (B) may be made of any inorganic material. The inorganic fine particles (B) are preferably one or more selected from the group consisting of metal oxide fine particles (B1) and metal fine particles (B2). Using the photosensitive composition containing metal oxide fine particles (B1) makes it easy to form high refractive index materials. Using the photosensitive composition containing metal fine particles (B2) makes it possible to form materials with electrical conductivity or materials with strong optical absorption at a specific wavelength. Thus, the photosensitive composition containing metal fine particles (B2) can be used to form materials suitable for use in bandpass filters. The metal oxide fine particles (B1) may include any type of metal oxide that does not compromise the desired effect. Preferred examples of the metal oxide fine particles (B1) are at least one type of particles selected from the group consisting of zirconium oxide fine particles, titanium oxide fine particles, barium titanate fine particles, cerium oxide fine particles, and niobium pentoxide fine particles. The metal fine particles (B2) may include any type of metal that does not compromise the desired effect. The metal fine particles (B2) may include an elementary metal or an alloy. Preferred examples of the metal fine particles (B2) include gold fine particles and platinum fine particles. Other preferred examples of the inorganic fine particles (B) include semimetal fine particles such as silicon fine particles (silicon nanoparticles (SiNPs)). Among the examples of the inorganic fine particles shown above, at least one type of metal oxide fine particles (B1) selected from the group consisting of titanium oxide fine particles, zirconium oxide fine particles, and niobium oxide fine particles are particularly preferred. The photosensitive composition may contain one or a combination of two or more of these types of inorganic fine particles (B).

The inorganic fine particles (B) preferably have an average particle size of 500 nm or less or an average particle size of 2 nm or more and 100 nm or less for production of transparent materials from the photosensitive composition or for stable dispersion of the inorganic fine particles (B) in the photosensitive composition.

The metal oxide fine particles (B1) preferably have surfaces modified with an ethylenically unsaturated double bond-containing group. The surface modification with an ethylenically unsaturated double bond-containing group will make the metal oxide fine particles (B1) less likely to aggregate. Thus, in particular, the photosensitive composition containing the metal oxide fine particles (B1) surface-modified with an ethylenically unsaturated double bond-containing group can easily form a material containing less localized metal oxide fine particles (B1).

For example, an ethylenically unsaturated double bond-containing capping agent may be allowed to react with the surfaces of the metal oxide fine particles (B1) to form ethylenically unsaturated double bond-containing group-modified metal oxide fine particles (B1), which have a chemical bond, such as a covalent bond, between their surfaces and the ethylenically unsaturated double bond-containing group.

Any suitable method may be used to bond the ethylenically unsaturated double bond-containing capping agent to the surfaces of the metal oxide fine particles (B1) via a chemical bond, such as a covalent bond. In general, the surfaces of the metal oxide fine particles (B1) have hydroxyl groups. The reactive group of the capping agent may be allowed to react with such hydroxyl groups so that the capping agent can be covalently bonded to the surfaces of the metal oxide fine particles (B1). Preferred examples of the reactive group of the capping agent include trialkoxysilyl groups, such as trimethoxysilyl and triethoxysilyl; dialkoxysilyl groups, such as dimethoxysilyl and diethoxysilyl; monoalkoxysilyl groups, such as monomethoxysilyl and monoethoxysilyl; trihalosilyl groups, such as trichlorosilyl; dihalosilyl groups, such as dichlorosilyl; monohalosilyl groups, such as monochlorosilyl; carboxy groups; halocarbonyl groups, such as chlorocarbonyl; a hydroxyl group; a phosphono group ($—P(═O)(OH)_2$); and a phosphate group ($—O—P(═O)(OH)_2$).

The trialkoxysilyl, dialkoxysilyl, monoalkoxysilyl, trihalosilyl, dihalosilyl, or monohalosilyl group will form a siloxane bond with the surfaces of the metal oxide nanoparticles (B). The carboxy or halocarbonyl group will form a bond represented by "metal oxide-O—CO—" with the surfaces of the metal oxide fine particles (B1). The hydroxyl group will form a bond represented by "metal oxide-O—" with the surfaces of the metal oxide fine particles (B1). The phosphono or phosphate group will form a bond represented by "metal oxide-O—P(═O)<" with the surfaces of the metal oxide fine particles (B1).

The capping agent may have a group bonded to the reactive group. Such a group may include a hydrogen atom or any organic group. Such an organic group may contain a heteroatom, such as O, N, S, P, B, Si, or halogen. The group bonded to the reactive group may be an alkyl group that may be linear or branched and may be interrupted by an oxygen atom (—O—); an alkenyl group that may be linear or branched and may be interrupted by an oxygen atom (—O); an alkynyl group that may be linear or branched and may be interrupted by an oxygen atom (—O—); a cycloalkyl group; an aromatic hydrocarbon group; or a heterocyclic group. These groups may be substituted with a substituent, such as a halogen atom, an epoxy-containing group, such as glycidyl, a hydroxyl group, a mercapto group, an amino group, a (meth)acryloyl group, or an isocyanate group. These groups may have any number of substituents.

The group bonded to the reactive group is also preferably a group represented by $—(SiR^{b1}R^{b2}—O—)_r—(SiR^{b3}R^{b4}—O—)_s—R^{b5}$. $R^{b1}$, $R^{b2}$, $R^{b3}$, and $R^{b4}$ may be the same organic group or different organic groups. Preferred examples of the organic group include alkyl groups, such as methyl and ethyl; alkenyl groups, such as vinyl and allyl; aromatic hydrocarbon groups, such as phenyl, naphthyl, and tolyl; epoxy-containing groups, such as 3-glycidoxypropyl; and a (meth)acryloyloxy group. In the formula, $R^{b5}$ may be, for example, $—Si(CH_3)_3$, $—Si(CH_3)_2H$, $—Si(CH_3)_2(CH═CH_2)$, $—Si(CH_3)_2(CH_2CH_2CH_2CH_3)$, or any other terminal group. In the formula, r and s are each independently an integer of 0 or more and 60 or less. In the formula, r and s are not simultaneously 0.

Preferred examples of the capping agent include unsaturated group-containing alkoxysilanes, such as vinyltrimethoxysilane, vinyltriethoxysilane, allyltrimethoxysilane, allyltriethoxysilane, 1-hexenyltrimethoxysilane, 1-hexenyltriethoxysilane, 1-octenyltrimethoxysilane, 1-octenyltriethoxysilane, 3-acryloyloxypropyltrimethoxysilane, 3-acryloylpropyltriethoxysilane, 3-methacryloyloxypropyltrimethoxysilane, and 3-methacryloyloxypropyltriethoxysilane; unsaturated group-containing alcohols, such as 2-hydroxyethyl (meth)acrylate, 3-hydroxypropyl (meth)acrylate, allyl alcohol, ethylene glycol monoallyl ether, propylene glycol monoallyl ether, and 3-allyloxypropanol; (meth)acrylic acid; and (meth)acrylic acid halides, such as (meth)acrylic acid chloride.

The capping agent may be used in any suitable amount to form a chemical bond, such as a covalent bond, on the surfaces of the metal oxide fine particles (B1). Preferably, the capping agent is used in a sufficient amount to react with almost all the hydroxyl groups on the surfaces of the metal oxide fine particles (B1).

The content of the inorganic fine particles (B) in the photosensitive composition may be any level as long as the object of the present invention will not be compromised. The content of the inorganic fine particles (B) in the photosensitive composition is preferably 5 mass % or more and 95 mass % or less, more preferably 35 mass % or more and 93 mass % or less, even more preferably 40 mass % or more and 90 mass % or less, based on the mass calculated by subtracting the mass of the solvent (S) from the mass of the photosensitive composition. The photosensitive composition with the content of the inorganic fine particles (B) falling within the above range can easily keep the inorganic fine particles (B) stably dispersed. The inorganic fine particles (B) can also produce the desired effect in the photosensitive composition with the content of the inorganic fine particles (B) falling within the above range. In particular, for ease of forming high refractive index materials in a case where the inorganic fine particles (B) are metal oxide fine particles (B1), the photosensitive composition preferably has a metal oxide fine particle (B1) content of 70 mass % or more, more preferably 75 mass % or more and 98 mass % or less, even more preferably 80 mass % or more and 95 mass % or less, based on the mass calculated by subtracting the mass of the solvent (S) from the mass of the photosensitive composition. In this regard, when the surfaces of the metal oxide fine particles (B1) are modified with an ethylenically unsaturated double bond-containing group, the mass of the capping agent having the ethylenically unsaturated double bond-containing group on the surfaces of the metal oxide fine particles (B1) should be counted into the mass of the metal oxide fine particles (B1).

Initiating Agent (C)

The photosensitive composition contains an initiating agent (C) for curing the photopolymerizable compound(s) (A). Although the compound (A1) may act as an initiating agent, the term "initiating agent (C)" as used herein means a compound different from the compound (A1). When the photopolymerizable compound (A) has a radically polymerizable group, a radical polymerization initiating agent (C1) may be used as the initiating agent (C). When the photopolymerizable compound (A) has a cationically polymerizable group, a cationic polymerization initiating agent (C2) may be used as the initiating agent (C). The initiating agent (C) may be a photo-initiating agent, which allows regioselective curing of the photosensitive composition and can be used without any concern about, for example, heat-induced degradation, volatilization, or sublimation of components of the photosensitive composition. The initiating agent (C) may be any of various conventionally-known polymerization initiating agents.

A photo-radical polymerization initiating agent is useful as the radical polymerization initiating agent (C1). Examples of such a photo-radical polymerization initiating agent include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl) ketone, 2-methyl-1-[4-(methylthio)phenyl]-2-morpholinopropan-1-one, 2-benzyl-2-dimethylamino-l-(4-morpholinophenyl)-butan-1-one, O-acetyl-1-[6-(2-methylbenzoyl)-9-ethyl-9H-carbazol-3-yl]ethanone oxime, (9-ethyl-6-nitro-9H-carbazol-3-yl) [4-(2-methoxy-1-methylethoxy)-2-methylphenyl]methanone O-acetyloxime, 2-(benzoyloxyimino)-1-[4-(phenylthio)phenyl]-1-octanone, 2,4,6-trimethylbenzoyl diphenylphosphine oxide, 4-benzoyl-4'-methyl dimethyl sulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexyl benzoate, 4-dimethylamino-2-isoamyl benzoate, benzyl-β-methoxyethyl acetal, benzyl dimethyl ketal, 1-phenyl-1,2-propanedione-2-(O-ethoxycarbonyl) oxime, methyl o-benzoyl benzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene hydroperoxide, 2-mercaptobenzimidazole, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylaminobenzophenone, 4,4'-bisdiethylaminobenzophenone, 4,4'-dichlorobenzophenone, 3,3-dimethyl-4-methoxybenzophenone, benzil, benzoin, benzoin methyl ether, benzoin ethyl ether, benzoin isopropyl ether, benzoin n-butyl ether, benzoin isobutyl ether, benzoin butyl ether, acetophenone, 2,2-diethoxyacetophenone, p-dimethylacetophenone, p-dimethylaminopropiophenone, 2-hydroxy-2-methylpropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylaminobenzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy)styrylphenyl-s-triazine, and 2,4-bis-trichloromethyl-6-(2-bromo-4-methoxy)styrylphenyl-s-triazine. These photo-radical polymerization initiating agents may be used alone, or two or more of these photo-radical polymerization initiating agents may be used in combination.

In particular, in view of the sensitivity of the photosensitive composition, the photo-radical polymerization initiating agent is preferably an oxime ester compound. Such an oxime ester compound is preferably a compound having a partial structure of Formula (c1) below.

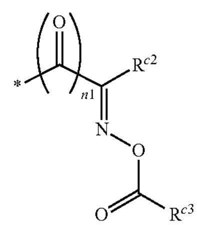

(c1)

In Formula (c1), n1 is 0 or 1, $R^{c2}$ is a monovalent organic group, $R^{c3}$ is a hydrogen atom, an optionally substituted aliphatic hydrocarbon group having 1 or more and 20 or less carbon atoms, or an optionally substituted aryl group, and

* indicates a bond.

The compound having a partial structure of Formula (c1) preferably has a carbazole skeleton, a fluorene skeleton, a diphenyl ether skeleton, or a phenyl sulfide skeleton. The compound having a partial structure of Formula (c1) preferably has one or two partial structures of Formula (c1).

The compound having a partial structure of Formula (c1) may be a compound of Formula (c2) below.

(c2)

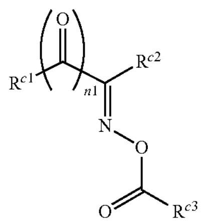

In Formula (c2), $R^{c1}$ is a group of Formula (c3), (c4), or (c5) below, n1 is 0 or 1, $R^{c2}$ is a monovalent organic group, and $R^{c3}$ is a hydrogen atom, an optionally substituted aliphatic hydrocarbon group having 1 or more and 20 or less carbon atoms, or an optionally substituted aryl group.

(c3)

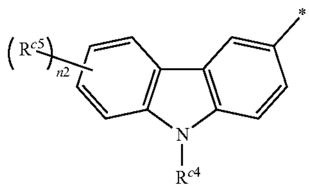

In Formula (c3), $R^{c4}$ and $R^{c5}$ are each independently a monovalent organic group, n2 is an integer of 0 or more and 3 or less, when n2 is 2 or 3, two or more $R^{c5}$s may be the same or different and may be bonded together to form a ring, and

* indicates a bond.

(c4)

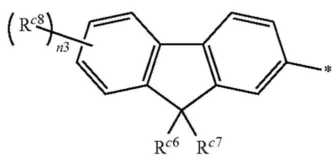

In Formula (c4), $R^{c6}$ and $R^{c7}$ are each independently an optionally substituted chain alkyl group, an optionally substituted chain alkoxy group, an optionally substituted cyclic organic group, or a hydrogen atom, $R^{c6}$ and $R^{c7}$ may be bonded to each other to form a ring, $R^{c7}$ and the benzene ring in the fluorene skeleton may be bonded to each other to form a ring, $R^{c8}$ is a nitro group or a monovalent organic group, n3 is an integer of 0 or more and 4 or less, and

* indicates a bond.

(c5)

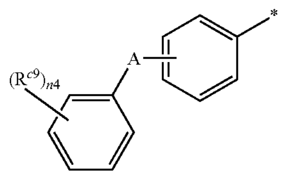

In Formula (c5), $R^{c9}$ is a monovalent organic group, a halogen atom, a nitro group, or a cyano group, A is S or O, n4 is an integer of 0 or more and 4 or less, and

* indicates a bond.

In Formula (c3), $R^{c4}$ is a monovalent organic group. $R^{c4}$ may be selected from various organic groups that do not compromise the object of the present invention. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not limited to, 1 or more and 50 or less, more preferably 1 or more and 20 or less. Preferred examples of $R^{c4}$ include an optionally substituted alkyl group having 1 or more and 20 or less carbon atoms, an optionally substituted cycloalkyl group having 3 or more and 20 or less carbon atoms, an optionally substituted saturated aliphatic acyl group having 2 or more and 20 or less carbon atoms, an optionally substituted alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthyl group, an optionally substituted naphthoyl group, an optionally substituted naphthoxycarbonyl group, an optionally substituted naphthylalkyl group having 11 or more and 20 or less carbon atoms, an optionally substituted heterocyclyl group, and an optionally substituted heterocyclylcarbonyl group.

In particular, $R^{c4}$ is preferably an alkyl group having 1 or more and 20 or less carbon atoms. The alkyl group may be linear or branched. In order for the compound of Formula (c3) to have good solubility in the photosensitive composition, the alkyl group of $R^{e4}$ preferably has 2 or more carbon atoms, more preferably 5 or more carbon atoms, even more preferably 7 or more carbon atoms. In order for the compound of Formula (c3) to have good compatibility with other components in the photosensitive composition, the alkyl group of $R^{e4}$ preferably has 15 or less carbon atoms, more preferably 10 or less carbon atoms.

When $R^{c4}$ has a substituent, preferred examples of the substituent include a hydroxyl group, an alkyl group having 1 or more and 20 or less carbon atoms, an alkoxy group having 1 or more and 20 or less carbon atoms, an aliphatic acyl group having 2 or more and 20 or less carbon atoms, an aliphatic acyloxy group having 2 or more and 20 or less carbon atoms, a phenoxy group, a benzoyl group, a benzoyloxy group, a group represented by —$PO(OR)_2$ (wherein R is an alkyl group having 1 or more and 6 or less carbon atoms), a halogen atom, a cyano group, and a heterocyclyl group.

The heterocyclyl group of $R^{c4}$ may be an aliphatic heterocyclic group or an aromatic heterocyclic group. The heterocyclyl group of $R^{c}a$ may also be a five- or six-membered monocyclic ring containing one or more N, S, or O atoms, or a heterocyclyl group including such monocyclic rings fused together or including such a monocyclic ring and a benzene ring fused together. When the heterocyclyl group is a fused ring, it should have up to three rings. The heterocyclic ring constituting the heterocyclyl group may be furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, or tetrahydrofuran. The heterocyclyl group of $R^{c4}$ may have a substituent, such as a hydroxyl group, an alkoxy group having 1 or more and 6 or less carbon atoms, a halogen atom, a cyano group, or a nitro group.

Preferred examples of $R^{c4}$ described above include methyl, ethyl, n-propyl, isopropyl, n-butyl, isobutyl, sec-butyl, tert-butyl, n-pentyl, isopentyl, neopentyl, pentan-3-yl, sec-pentyl, tert-pentyl, n-hexyl, n-heptyl, n-octyl, and 2-ethylhexyl. In order for the compound of Formula (c3) to have good solubility in the photosensitive composition, $R^{c4}$ is preferably n-octyl or 2-ethylhexyl, more preferably 2-ethylhexyl.

In Formula (c3), $R^{c5}$ is a monovalent organic group. $R^{c5}$ may be selected from various organic groups that do not compromise the object of the present invention. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not limited to, 1 or more and 50 or less, more preferably 1 or more and 20 or less. Preferred examples of the monovalent organic group of $R^{c5}$ include alkyl, alkoxy, cycloalkyl, cycloalkoxy, saturated aliphatic acyl, alkoxycarbonyl, saturated aliphatic acyloxy, optionally substituted phenyl, optionally substituted phenoxy, optionally substituted benzoyl, optionally substituted phenoxycarbonyl, optionally substituted benzoyloxy, optionally substituted phenylalkyl, optionally substituted naphthyl, optionally substituted naphthoxy, optionally substituted naphthoyl, optionally substituted naphthoxycarbonyl, optionally substituted naphthoyloxy, optionally substituted naphthylalkyl, optionally substituted heterocyclyl, optionally substituted heterocyclylcarbonyl, amino substituted with one or two organic groups, morpholin-1-yl, piperazin-1-yl, halogen, nitro, cyano, and a substituent containing a group represented by $HX_2C$— or $H_2XC$—, wherein Xs are each independently a halogen atom.

The alkyl group of $R^{c5}$ preferably has 1 or more and 20 or less carbon atoms, more preferably 1 or more and 6 or less carbon atoms. The alkyl group of $R^{c5}$ may be linear or branched. Examples of the alkyl group of $R^{c5}$ include methyl, ethyl, n-propyl, isopropyl, n-butyl, isobutyl, sec-butyl, tert-butyl, n-pentyl, isopentyl, sec-pentyl, tert-pentyl, n-hexyl, n-heptyl, n-octyl, isooctyl, sec-octyl, tert-octyl, n-nonyl, isononyl, n-decyl, and isodecyl. The alkyl group of $R^{c5}$ may have a carbon chain containing an ether bond (—O—). Examples of the alkyl group having an ether bond-containing carbon chain include methoxyethyl, ethoxyethyl, methoxyethoxyethyl, ethoxyethoxyethyl, propyloxyethoxyethyl, and methoxypropyl.

The alkoxy group of $R^{c5}$ preferably has 1 or more and 20 or less carbon atoms, more preferably 1 or more and 6 or less carbon atoms. The alkoxy group of $R^{c5}$ may be linear or branched. Examples of the alkoxy group of $R^{c5}$ include methoxy, ethoxy, n-propyloxy, isopropyloxy, n-butyloxy, isobutyloxy, sec-butyloxy, tert-butyloxy, n-pentyloxy, isopentyloxy, sec-pentyloxy, tert-pentyloxy, n-hexyloxy, n-heptyloxy, n-octyloxy, isooctyloxy, sec-octyloxy, tert-octyloxy, n-nonyloxy, isononyloxy, n-decyloxy, and isodecyloxy. The alkoxy group of $R^{c5}$ may have a carbon chain containing an ether bond (—O—). Examples of the alkoxy group having an ether bond-containing carbon chain include methoxyethoxy, ethoxyethoxy, methoxyethoxyethoxy, ethoxyethoxyethoxy, propyloxyethoxyethoxy, and methoxypropyloxy.

The cycloalkyl or cycloalkoxy group of $R^{c5}$ preferably has 3 or more and 10 or less carbon atoms, more preferably 3 or more and 6 or less carbon atoms. Examples of the cycloalkyl group of $R^{c5}$ include cyclopropyl, cyclobutyl, cyclopentyl, cyclohexyl, cycloheptyl, and cyclooctyl. Examples of the cycloalkoxy group of $R^{c5}$ include cyclopropyloxy, cyclobutyloxy, cyclopentyloxy, cyclohexyloxy, cycloheptyloxy, and cyclooctyloxy.

The saturated aliphatic acyl or acyloxy group of $R^{c5}$ preferably has 2 or more and 21 or less carbon atoms, more preferably 2 or more and 7 or less carbon atoms. Examples of the saturated aliphatic acyl group of $R^{c5}$ include acetyl, propanoyl, n-butanoyl, 2-methylpropanoyl, n-pentanoyl, 2,2-dimethylpropanoyl, n-hexanoyl, n-heptanoyl, n-octanoyl, n-nonanoyl, n-decanoyl, n-undecanoyl, n-dodecanoyl, n-tridecanoyl, n-tetradecanoyl, n-pentadecanoyl, and n-hexadecanoyl. Examples of the saturated aliphatic acyloxy group of $R^{c5}$ include acetyloxy, propanoyloxy, n-butanoyloxy, 2-methylpropanoyloxy, n-pentanoyloxy, 2,2-dimethylpropanoyloxy, n-hexanoyloxy, n-heptanoyloxy, n-octanoyloxy, n-nonanoyloxy, n-dodecanoyloxy, n-undecanoyloxy, n-dodecanoyloxy, n-tridecanoyloxy, n-tetradecanoyloxy, n-pentadecanoyloxy, and n-hexadecanoyloxy.

The alkoxycarbonyl group of $R^{c5}$ preferably has 2 or more and 20 or less carbon atoms, more preferably 2 or more and 7 or less carbon atoms. Examples of the alkoxycarbonyl group of $R^{c5}$ include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, isopentyloxycarbonyl, sec-pentyloxycarbonyl, tert-pentyloxycarbonyl, n-hexyloxycarbonyl, n-heptyloxycarbonyl, n-octyloxycarbonyl, isooctyloxycarbonyl, sec-octyloxycarbonyl, tert-octyloxycarbonyl, n-nonyloxycarbonyl, isononyloxycarbonyl, n-decyloxycarbonyl, and isodecyloxycarbonyl.

The phenylalkyl group of $R^{c5}$ preferably has 7 or more and 20 or less carbon atoms, more preferably 7 or more and 10 or less carbon atoms. The naphthylalkyl group of $R^{c5}$ preferably has 11 or more and 20 or less carbon atoms, more preferably 11 or more and 14 or less carbon atoms. Examples of the phenylalkyl group of $R^{c5}$ include benzyl, 2-phenylethyl, 3-phenylpropyl, and 4-phenylbutyl. Examples of the naphthylalkyl group of $R^{c5}$ include a-naphthylmethyl, β-naphthylmethyl, 2-(α-naphthyl)ethyl, and 2-(β-naphthyl)ethyl. The phenylalkyl or naphthylalkyl group of $R^{c5}$ may further have a substituent on the phenyl or naphthyl group.

The heterocyclyl group of $R^{c5}$ may further have a substituent as in the case of the heterocyclyl group of $R^{c4}$ in Formula (c3). Examples of the heterocyclyl group in the heterocyclylcarbonyl group of $R^{c5}$ are the same as those of the heterocyclyl group of $R^{c5}$.

When $R^{c5}$ is an amino group substituted with one or two organic groups, preferred examples of the organic group include alkyl having 1 or more and 20 or less carbon atoms, cycloalkyl having 3 or more and 10 or less carbon atoms, saturated aliphatic acyl having 2 or more and 21 or less carbon atoms, optionally substituted phenyl, optionally substituted benzoyl, optionally substituted phenylalkyl having 7 or more and 20 or less carbon atoms, optionally substituted naphthyl, optionally substituted naphthoyl, optionally substituted naphthylalkyl having 11 or more and 20 or less carbon atoms, and heterocyclyl. Preferred examples of the organic group are the same as those for $R^{c5}$. Examples of the amino group substituted with one or two organic groups include methylamino, ethylamino, diethylamino, n-propylamino, di-n-propylamino, isopropylamino, n-butylamino, di-n-butylamino, n-pentylamino, n-hexylamino, n-heptylamino, n-octylamino, n-nonylamino, n-decylamino, phenylamino, naphthylamino, acetylamino, propanoylamino, n-butanoylamino, n-pentanoylamino, n-hexanoylamino, n-heptanoylamino, n-octanoylamino, n-decanoylamino, benzoylamino, α-naphthoylamino, and β-naphthoylamino.

The phenyl, naphthyl, or heterocyclyl group in $R^5$ may further have a substituent. Such a substituent may be a substituent containing a group represented by $HX_2C$— or $H_2XC$— (e.g., a halogenated alkoxy group containing a group represented by $HX_2C$— or $H_2XC$—, a halogenated alkyl group containing a group represented by $HX_2C$— or $H_2XC$—), alkyl having 1 or more and 6 or less carbon atoms, alkoxy having 1 or more and 6 or less carbon atoms, saturated aliphatic acyl having 2 or more and 7 or less carbon atoms, alkoxycarbonyl having 2 or more and 7 or less carbon atoms, saturated aliphatic acyloxy having 2 or more and 7 or less carbon atoms, monoalkylamino having alkyl of 1 or more and 6 or less carbon atoms, dialkylamino having alkyl of 1 or more and 6 or less carbon atoms, morpholin-1-yl, piperazin-1-yl, benzoyl, halogen, nitro, or cyano. The phenyl, naphthyl, or heterocyclyl group in $R^{c5}$ may further have any number of substituents as long as the object of the present invention will not be compromised. Preferably, the phenyl, naphthyl, or heterocyclyl group in RCS has one or more and four or less substituents. The phenyl, naphthyl, or heterocyclyl group in $R^{c5}$ may have two or more substituents the same as or different from one another.

The benzoyl group in $R^{c5}$ may further have a substituent. Such a substituent may be alkyl having 1 or more and 6 or less carbon atoms, morpholin-1-yl, piperazin-1-yl, 2-thenoyl (thiophen-2-ylcarbonyl), furan-3-ylcarbonyl, or phenyl.

The halogen atom represented by X may be fluorine, chlorine, or bromine, and is preferably fluorine.

The substituent containing a group represented by $HX_2C$— or $H_2XC$— may be a halogenated alkoxy group containing a group represented by $HX_2C$— or $H_2XC$—, a group having a halogenated alkoxy group containing a group represented by $HX_2C$— or $H_2XC$—, a halogenated alkyl group containing a group represented by $HX_2C$— or $H_2XC$—, or a group having a halogenated alkyl group containing a group represented by $HX_2C$— or $H_2XC$—, and is more preferably a halogenated alkoxy group containing a group represented by $HX_2C$— or $H_2XC$— or a group having a halogenated alkoxy group containing a group represented by $HX_2C$— or $H_2XC$—.

The group having a halogenated alkyl group containing a group represented by $HX_2C$— or $H_2XC$— may be an aromatic group (e.g., phenyl, naphthyl) substituted with a halogenated alkyl group containing a group represented by $HX_2C$— or $H_2XC$— or a cycloalkyl group (e.g., cyclopentyl, cyclohexyl) substituted with a halogenated alkyl group containing a group represented by $HX_2C$— or $H_2XC$—, and is preferably an aromatic group substituted with a halogenated alkyl group containing a group represented by $HX_2C$— or $H_2XC$—.

The group having a halogenated alkoxy group containing a group represented by $HX_2C$— or $H_2XC$— may be an aromatic group (e.g., phenyl, naphthyl) substituted with a halogenated alkoxy group containing a group represented by $HX_2C$— or $H_2XC$—, an alkyl group (e.g., methyl, ethyl, n-propyl, isopropyl) substituted with a halogenated alkoxy group containing a group represented by $HX_2C$— or $H_2XC$—, or a cycloalkyl group (e.g., cyclopentyl, cyclohexyl) substituted with a halogenated alkoxy group containing a group represented by $HX_2C$— or $H_2XC$—, and is preferably an aromatic group substituted with a halogenated alkoxy group containing a group represented by $HX_2C$— or $H_2XC$—.

$R^{c5}$ is also preferably a cycloalkylalkyl group, a phenoxyalkyl group optionally having a substituent on the aromatic ring, or a phenylthioalkyl group optionally having a substituent on the aromatic ring. The phenoxyalkyl or phenylthioalkyl group may have the same substituent as the phenyl group in $R^{c5}$ may have.

The monovalent organic group of $R^{c5}$ is preferably alkyl, cycloalkyl, optionally substituted phenyl, cycloalkylalkyl, or phenylthioalkyl optionally having a substituent on the aromatic ring. The alkyl group is preferably alkyl having 1 or more and 20 or less carbon atoms, more preferably alkyl having 1 or more and 8 or less carbon atoms, even more preferably alkyl having 1 or more and 4 or less carbon atoms, most preferably methyl. The optionally substituted phenyl group is preferably methylphenyl, more preferably 2-methylphenyl. The cycloalkyl group in the cycloalkylalkyl group preferably has 5 or more and 10 or less carbon atoms, more preferably 5 or more and 8 or less carbon atoms, even more preferably 5 or 6 carbon atoms. The alkylene group in the cycloalkylalkyl group preferably has 1 or more and 8 or less carbon atoms, more preferably 1 or more and 4 or less carbon atoms, even more preferably 2 carbon atoms. The cycloalkylalkyl group is preferably cyclopentylethyl. The alkylene group in the phenylthioalkyl group optionally having a substituent on the aromatic ring preferably has 1 or more and 8 or less carbon atoms, more preferably 1 or more and 4 or less carbon atoms, even more preferably 2 carbon atoms. The phenylthioalkyl group optionally having a substituent on the aromatic ring is preferably 2-(4-chlorophenylthio)ethyl.

The group of Formula (c3) may have two or more $R^c$s that are bonded together to form a ring, such as a hydrocarbon ring or a heterocyclic ring. The heteroatom in the heterocyclic ring may be, for example, N, O, or S. In particular, the ring formed by two or more $R^{c5}$s bonded together is preferably an aromatic ring. Such an aromatic ring may be an aromatic hydrocarbon ring or an aromatic heterocyclic ring. The aromatic ring is preferably an aromatic hydrocarbon ring. Examples of the group of Formula (c3) having two or more $R^{c5}$s bonded together to form a benzene ring are shown below.

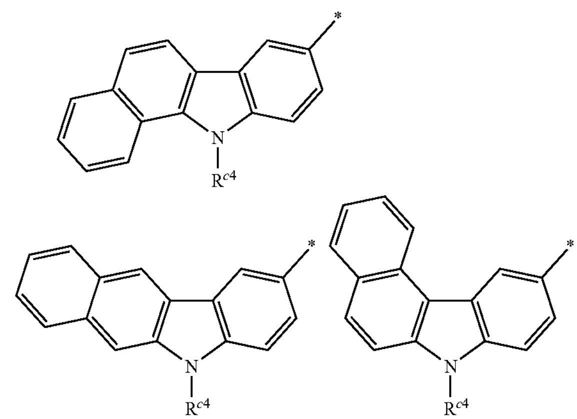

In the group of Formula (c4), $R^{c8}$ is a nitro group or a monovalent organic group. $R^{c8}$ on the fused ring in Formula (c4) is bonded to a six-membered aromatic ring different from the aromatic ring to which the group represented by $-(CO)_{n1}-$ is bonded. In Formula (c4), $R^{c8}$ may be bonded at any position. When the group of Formula (c4) has one or more $R^{c8}$s, one $R^{c8}$ should preferably be bonded at position 7 of the fluorene skeleton for ease of synthesis of the compound of Formula (c2). In other words, when the group of Formula (c4) has one or more $R^{c8}$s, the group of Formula (c4) should preferably be represented by Formula (c6) below. Two or more $R^{c8}$s may be the same or different.

(c6)

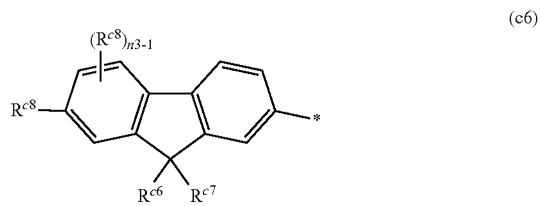

In Formula (c6), $R^{c6}$, $R^{c7}$, $R^{c8}$, and n3 respectively have the same meaning as $R^{c6}$, $R^{c7}$, $R^{c8}$, and n3 in Formula (c4).

$R^{c8}$ may be any monovalent organic group that does not compromise the object of the present invention. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not limited to, 1 or more and 50 or less, more preferably 1 or more and 20 or less. Preferred examples of the monovalent organic group of $R^{c8}$ may be the same as those of the monovalent organic group of $R^{c5}$ in Formula (c3).

In Formula (c4), $R^{c6}$ and $R^{c7}$ are each an optionally substituted chain alkyl group, an optionally substituted chain alkoxy group, an optionally substituted cyclic organic group, or a hydrogen atom. $R^{c6}$ and $R^{c7}$ may be bonded to each other to form a ring. In particular, $R^{c6}$ and $R^{c7}$ are each preferably an optionally substituted chain alkyl group. The optionally substituted chain alkyl group of $R^{c6}$ or $R^{c7}$ may be linear or branched.

$R^{c6}$ and $R^{c7}$ may each be an unsubstituted chain alkyl group. In this case, the chain alkyl group preferably has 1 or more and 20 or less carbon atoms, more preferably 1 or more and 10 or less carbon atoms, even more preferably 1 or more and 6 or less carbon atoms. Examples of the chain alkyl group of $R^{c6}$ or $R^{c7}$ include methyl, ethyl, n-propyl, isopropyl, n-butyl, isobutyl, sec-butyl, tert-butyl, n-pentyl, isopentyl, sec-pentyl, tert-pentyl, n-hexyl, n-heptyl, n-octyl, isooctyl, sec-octyl, tert-octyl, n-nonyl, isononyl, n-decyl, and isodecyl. The alkyl group of $R^{c6}$ or $R^{c7}$ may have a carbon chain containing an ether bond (—O—). Examples of the alkyl group having an ether bond-containing carbon chain include methoxyethyl, ethoxyethyl, methoxyethoxyethyl, ethoxyethoxyethyl, propyloxyethoxyethyl, and methoxypropyl.

The chain alkyl group of the substituted chain alkyl group of $R^{c6}$ or $R^{c7}$ preferably has 1 or more and 20 or less carbon atoms, more preferably 1 or more and 10 or less carbon atoms, even more preferably 1 or more and 6 or less carbon atoms. In this case, the number of carbon atoms in the substituent should not be counted into the number of carbon atoms in the chain alkyl group. The substituted chain alkyl group is preferably linear.

The alkyl group may have any substituent that does not compromise the object of the present invention. Preferred examples of such a substituent include alkoxy, cyano, a halogen atom, halogenated alkyl, a cyclic organic group, and alkoxycarbonyl. The halogen atom may be fluorine, chlorine, bromine, or iodine. In particular, fluorine, chlorine, or bromine is preferred. Examples of the cyclic organic group include a cycloalkyl group, an aromatic hydrocarbon group, and a heterocyclyl group. Examples of the cycloalkyl group are the same as those of the cycloalkyl group of $R^{c8}$. Examples of the aromatic hydrocarbon group include phenyl, naphthyl, biphenylyl, anthryl, and phenanthryl. Examples of the heterocyclyl group are the same as those of the heterocyclyl group of $R^{c8}$e. The alkoxycarbonyl group of $R^{c8}$ may have a linear or branched alkoxy group and preferably has a linear alkoxy group. The alkoxy group in the alkoxycarbonyl group preferably has 1 or more and 10 or less carbon atoms, more preferably 1 or more and 6 or less carbon atoms.

The chain alkyl group may have any number of substituents. The preferred number of substituents depends on the number of carbon atoms in the chain alkyl group. The number of substituents is typically 1 or more and 20 or less, preferably 1 or more and 10 or less, more preferably 1 or more and 6 or less.

The chain alkoxy group of the unsubstituted chain alkoxy group of $R^{c6}$ or $R^{c7}$ preferably has 1 or more and 20 or less carbon atoms, more preferably 1 or more and 10 or less carbon atoms, even more preferably 1 or more and 6 or less carbon atoms. Examples of the chain alkoxy group of $R^{c6}$ or $R^{c7}$ include methoxy, ethoxy, n-propyloxy, isopropyloxy, n-butyloxy, isobutyloxy, sec-butyloxy, tert-butyloxy, n-pentyloxy, isopentyloxy, sec-pentyloxy, tert-pentyloxy, n-hexyloxy, n-heptyloxy, n-octyloxy, isooctyloxy, sec-octyloxy, tert-octyloxy, n-nonyloxy, isononyloxy, n-decyloxy, and isodecyloxy. The alkoxy group of $R^{c6}$ or $R^{c7}$ may have a carbon chain containing an ether bond (—O—). Examples of the alkoxy group having an ether bond-containing carbon chain include methoxyethoxy, ethoxyethoxy, methoxyethoxyethoxy, ethoxyethoxyethoxy, propyloxyethoxyethoxy, and methoxypropyloxy.

The chain alkoxy group of $R^{c6}$ or $R^{c7}$ may have a substituent, examples of which are the same as those of the substituent that the chain alkyl group of $R^{c6}$ or $R^{c7}$ may have.

The cyclic organic group of $R^{c6}$ or $R^{c7}$ may be alicyclic or aromatic. The cyclic organic group may be an aliphatic cyclic hydrocarbon group, an aromatic hydrocarbon group, or a heterocyclyl group. The cyclic organic group of $R^{c6}$ or $R^{c7}$ may have a substituent, examples of which are the same as those of the substituent that the chain alkyl group of $R^{c6}$ or $R^{c7}$ may have.

The aromatic hydrocarbon group of $R^{c6}$ or $R^{c7}$ is preferably a phenyl group, a group including two or more benzene rings bonded through a carbon-carbon bond, or a group including two or more benzene rings fused together. When the aromatic hydrocarbon group is a phenyl group or a group including two or more benzene rings bonded or fused together, the number of benzene rings in the aromatic hydrocarbon group is preferably, but not limited to, 3 or less, more preferably 2 or less, even more preferably 1. Preferred examples of the aromatic hydrocarbon group include phenyl, naphthyl, biphenylyl, anthryl, and phenanthryl.

The aliphatic cyclic hydrocarbon group of $R^{c6}$ or $R^{c7}$ may be monocyclic or polycyclic. The number of carbon atoms in the aliphatic cyclic hydrocarbon group is preferably, but not limited to, 3 or more and 20 or less, more preferably 3 or more and 10 or less. Examples of the monocyclic hydrocarbon group include cyclopropyl, cyclobutyl, cyclopentyl, cyclohexyl, cycloheptyl, cyclooctyl, norbornyl, isobornyl, tricyclononyl, tricyclodecyl, tetracyclododecyl, and adamantyl.

Examples of the heterocyclyl group of $R^{c6}$ or $R^{c7}$ may be the same as those of the heterocyclyl group of $R^{c5}$ in Formula (c3).

$R^{c6}$ and $R^{c7}$ may be bonded to each other to form a ring. The ring group formed by $R^{c6}$ and $R^{c7}$ is preferably a cycloalkylidene group. The cycloalkylidene group formed by $R^{c6}$ and $R^{c7}$ bonded together preferably has a five- or six-membered ring, more preferably a five-membered ring.

$R^{c7}$ and the benzene ring of the fluorene skeleton may form a ring, which may be an aromatic ring or an aliphatic ring.

The cycloalkylidene group formed by $R^{c6}$ and $R^{c7}$ bonded together may be fused with one or more other rings. For example, the cycloalkylidene group may be fused with a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, a pyrimidine ring, or any other ring.

In particular, the group of $R^{c6}$ or $R^{c7}$ described above is preferably, for example, a group represented by the formula $-A^1-A^2$. In the formula, $A^1$ is a linear alkylene group, and $A^2$ is an alkoxy group, a cyano group, a halogen atom, a halogenated alkyl group, a cyclic organic group, or an alkoxycarbonyl group.

The linear alkylene group of $A^1$ preferably has 1 or more and 10 or less carbon atoms, more preferably 1 or more and 6 or less carbon atoms. The alkoxy group of $A^2$ may be linear or branched, and is preferably linear. The alkoxy group preferably has 1 or more and 10 or less carbon atoms, more preferably 1 or more and 6 or less carbon atoms. The halogen atom represented by $A^2$ is preferably fluorine, chlorine, bromine, or iodine, more preferably fluorine, chlorine, or bromine. The halogen atom in the halogenated alkyl group of $A^2$ is preferably fluorine, chlorine, bromine, or iodine, more preferably fluorine, chlorine, or bromine. The halogenated alkyl group may be linear or branched, and is preferably linear. Examples of the cyclic organic group of $A^2$ are the same as those of the cyclic organic group that $R^{c6}$ or $R^{c7}$ may have as a substituent. Examples of the alkoxycarbonyl group of $A^2$ are the same as those of the alkoxycarbonyl group that $R^{c6}$ or $R^{c7}$ may have as a substituent.

Preferred examples of $R^{c6}$ or $R^{c7}$ include alkyl groups, such as ethyl, n-propyl, n-butyl, n-hexyl, n-heptyl, and n-octyl; alkoxyalkyl groups, such as 2-methoxyethyl, 3-methoxy-n-propyl, 4-methoxy-n-butyl, 5-methoxy-n-pentyl, 6-methoxy-n-hexyl, 7-methoxy-n-heptyl, 8-methoxy-n-octyl, 2-ethoxyethyl, 3-ethoxy-n-propyl, 4-ethoxy-n-butyl, 5-ethoxy-n-pentyl, 6-ethoxy-n-hexyl, 7-ethoxy-n-heptyl, and 8-ethoxy-n-octyl; cyanoalkyl groups, such as 2-cyanoethyl, 3-cyano-n-propyl, 4-cyano-n-butyl, 5-cyano-n-pentyl, 6-cyano-n-hexyl, 7-cyano-n-heptyl, and 8-cyano-n-octyl; phenylalkyl groups, such as 2-phenylethyl, 3-phenyl-n-propyl, 4-phenyl-n-butyl, 5-phenyl-n-pentyl, 6-phenyl-n-hexyl, 7-phenyl-n-heptyl, and 8-phenyl-n-octyl; cycloalkylalkyl groups, such as 2-cyclohexylethyl, 3-cyclohexyl-n-propyl, 4-cyclohexyl-n-butyl, 5-cyclohexyl-n-pentyl, 6-cyclohexyl-n-hexyl, 7-cyclohexyl-n-heptyl, 8-cyclohexyl-n-octyl, 2-cyclopentylethyl, 3-cyclopentyl-n-propyl, 4-cyclopentyl-n-butyl, 5-cyclopentyl-n-pentyl, 6-cyclopentyl-n-hexyl, 7-cyclopentyl-n-heptyl, and 8-cyclopentyl-n-octyl; alkoxycarbonylalkyl groups, such as 2-methoxycarbonylethyl, 3-methoxycarbonyl-n-propyl, 4-methoxycarbonyl-n-butyl, 5-methoxycarbonyl-n-pentyl, 6-methoxycarbonyl-n-hexyl, 7-methoxycarbonyl-n-heptyl, 8-methoxycarbonyl-n-octyl, 2-ethoxycarbonylethyl, 3-ethoxycarbonyl-n-propyl, 4-ethoxycarbonyl-n-butyl, 5-ethoxycarbonyl-n-pentyl, 6-ethoxycarbonyl-n-hexyl, 7-ethoxycarbonyl-n-heptyl, and 8-ethoxycarbonyl-n-octyl; and halogenated alkyl groups, such as 2-chloroethyl, 3-chloro-n-propyl, 4-chloro-n-butyl, 5-chloro-n-pentyl, 6-chloro-n-hexyl, 7-chloro-n-heptyl, 8-chloro-n-octyl, 2-bromoethyl, 3-bromo-n-propyl, 4-bromo-n-butyl, 5-bromo-n-pentyl, 6-bromo-n-hexyl, 7-bromo-n-heptyl, 8-bromo-n-octyl, 3,3,3-trifluoropropyl, and 3,3,4,4,5,5,5-heptafluoro-n-pentyl.

In particular, the group of $R^{c6}$ or $R^{c7}$ is preferably ethyl, n-propyl, n-butyl, n-pentyl, 2-methoxyethyl, 2-cyanoethyl, 2-phenylethyl, 2-cyclohexylethyl, 2-methoxycarbonylethyl, 2-chloroethyl, 2-bromoethyl, 3,3,3-trifluoropropyl, or 3,3,4,4,5,5,5-heptafluoro-n-pentyl.

In Formula (c5), A is preferably S in particular for easy availability of a photopolymerization initiating agent with high sensitivity.

In Formula (c5), $R^{c9}$ is a monovalent organic group, a halogen atom, a nitro group, or a cyano group. The monovalent organic group of $R^{c9}$ in Formula (c5) may be selected from various organic groups that do not compromise the object of the present invention. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not limited to, 1 or more and 50 or less, more preferably 1 or more and 20 or less. Preferred examples of the organic group of $R^{c9}$ in Formula (c5) may be the same as those of the monovalent organic group of $R^{c5}$ in Formula (c3).

$R^{c9}$ is preferably benzoyl; naphthoyl; benzoyl substituted with a group selected from the group consisting of alkyl having 1 or more and 6 or less carbon atoms, morpholin-1-yl, piperazin-1-yl, and phenyl; nitro; or optionally substituted benzofuranylcarbonyl, and more preferably benzoyl; naphthoyl; 2-methylphenylcarbonyl; 4-(piperazin-1-yl)phenylcarbonyl; or 4-(phenyl)phenylcarbonyl.

In Formula (c5), n4 is preferably an integer of 0 or more and 3 or less, more preferably an integer of 0 or more and 2 or less, even more preferably 0 or 1. When n4 is 1, $R^{c9}$ is preferably bonded at para position with respect to the bond between the oxygen or sulfur atom and the phenyl group to which $R^{c9}$ is bonded.

In Formula (c1) or (c2), the monovalent organic group of $R^{c2}$ may be any type as long as the object of the present invention will not be compromised. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not limited to, 1 or more and 50 or less, more preferably 1 or more and 20 or less. Preferred examples of the monovalent organic group of $R^{c2}$ may be the same as those of the monovalent organic group of $R^{c5}$ in Formula (c3). Examples of these groups are the same as those listed for $R^{c5}$ in Formula (c3). $R^{c2}$ is also preferably a cycloalkylalkyl group, a phenoxyalkyl group optionally having a substituent on the aromatic ring, or a phenylthioalkyl group optionally having a substituent on the aromatic ring. The phenoxyalkyl or phenylthioalkyl group may have a substituent, examples of which are the same as those of the substituent that the phenyl, naphthyl, or heterocyclyl group in $R^{c5}$ in Formula (c3) may further have.

In particular, the organic group of $R^{c2}$ is preferably a substituent containing a group represented by $HX_2C$— or $H_2XC$— shown above, an alkyl group, a cycloalkyl group, an optionally substituted phenyl group, a cycloalkylalkyl group, or a phenylthioalkyl group optionally having a substituent on the aromatic ring. The number of carbon atoms in the alkyl group, the optionally substituted phenyl group, or the cycloalkyl group of the cycloalkylalkyl group, the number of carbon atoms in the alkylene group of the cycloalkylalkyl group, or the number of carbon atoms in the cycloalkylalkyl group, the alkylene group of the phenylthioalkyl group optionally having a substituent on the aromatic ring, or the phenylthioalkyl group optionally having a substituent on the aromatic ring may be the same as that in $R^{c5}$ in Formula (c3).

$R^{c2}$ is also preferably a group represented by $-A^3$-CO—O-$A^4$. $A^3$ is a divalent organic group, and preferably a divalent hydrocarbon group or an alkylene group. $A^4$ is a monovalent organic group and preferably a monovalent hydrocarbon group.

The alkylene group of $A^3$ may be linear or branched and is preferably linear. The alkylene group of $A^3$ preferably has 1 or more and 10 or less carbon atoms, more preferably 1 or more and 6 or less carbon atoms, even more preferably 1 or more and 4 or less carbon atoms.

$A^4$ is preferably, for example, an alkyl group having 1 or more and 10 or less carbon atoms, an aralkyl group having 7 or more and 20 or less carbon atoms, or an aromatic hydrocarbon group having 6 or more and 20 or less carbon atoms. Preferred examples of $A^4$ include methyl, ethyl, n-propyl, isopropyl, n-butyl, isobutyl, sec-butyl, tert-butyl, n-pentyl, n-hexyl, phenyl, naphthyl, benzyl, phenethyl, a-naphthylmethyl, and β-naphthylmethyl.

Preferred examples of the group represented by $-A^3$-CO—O-A4 include 2-methoxycarbonylethyl, 2-ethoxycarbonylethyl, 2-n-propyloxycarbonylethyl, 2-n-butyloxycarbonylethyl, 2-n-pentyloxycarbonylethyl, 2-n-hexyloxycarbonylethyl, 2-benzyloxycarbonylethyl, 2-phenoxycarbonylethyl, 3-methoxycarbonyl-n-propyl, 3-ethoxycarbonyl-n-propyl, 3-n-propyloxycarbonyl-n-propyl, 3-n-butyloxycarbonyl-n-propyl, 3-n-pentyloxycarbonyl-n-propyl, 3-n-hexyloxycarbonyl-n-propyl, 3-benzyloxycarbonyl-n-propyl, and 3-phenoxycarbonyl-n-propyl.

$R^{c2}$ is also preferably a group of Formula (c7) or (c8) below.

(c7)

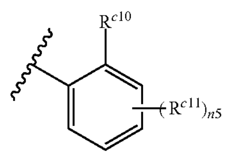

(c8)

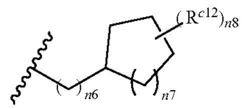

In Formulae (c7) and (c8), $R^{c10}$ and $R^{c11}$ are each independently a monovalent organic group, n5 is an integer of 0 or more and 4 or less, when $R^{c10}$ and $R^{c11}$ are in adjacent positions on the benzene ring, $R^{c10}$ and $R^{c11}$ may be bonded to each other to form a ring, $R^{c12}$ is a monovalent organic group, n6 is an integer of 1 or more and 8 or less, n7 is an integer of 1 or more and 5 or less, and n8 is an integer of 0 or more and n7+3 or less.

The organic group of $R^{c10}$ or $R^{c11}$ in Formula (c7) may be the same as $R^{c8}$ in Formula (c4). $R^{c10}$ is preferably a halogenated alkoxy group containing a group represented by $HX_2C$— or $H_2XC$—, a halogenated alkyl group containing a group represented by $HX_2C$— or $H_2XC$—, an alkyl group, or a phenyl group. $R^{c10}$ and $R^{c11}$ may be bonded to each other to form a ring, which may be an aromatic ring or an aliphatic ring. The group of Formula (c7) having $R^{c10}$ and $R^{c11}$ bonded to form a ring is preferably, for example, naphthalen-1-yl or 1,2,3,4-tetrahydronaphthalen-5-yl. In Formula (c7), n5 is an integer of 0 or more and 4 or less and preferably 0 or 1, more preferably 0.

In Formula (c8), $R^{c12}$ is an organic group. Examples of the organic group may be the same as those listed for the organic group of $R^{c8}$ in Formula (c4). The organic group is preferably alkyl. The alkyl group may be linear or branched. The alkyl group preferably has 1 or more and 10 or less carbon atoms, more preferably 1 or more and 5 or less carbon atoms, even more preferably 1 or more and 3 or less carbon atoms. $R^{c12}$ is preferably, for example, methyl, ethyl, propyl, isopropyl, or butyl and more preferably methyl.

In Formula (c8), n7 is an integer of 1 or more and 5 or less, preferably an integer of 1 or more and 3 or less, more preferably 1 or 2. In Formula (c8), n8 is an integer of 0 or more and n7+3 or less, preferably an integer of 0 or more and 3 or less, more preferably an integer of 0 or more and 2 or less, even more preferably 0. In Formula (c8), n6 is an integer of 1 or more and 8 or less, preferably an integer of 1 or more and 5 or less, more preferably an integer of 1 or more and 3 or less, even more preferably 1 or 2.

In Formula (c2), $R^{c3}$ is a hydrogen atom, an optionally substituted aliphatic hydrocarbon group having 1 or more and 20 or less carbon atoms, or an optionally substituted aryl group. The aliphatic hydrocarbon group of $R^{*3}$ may have a substituent, which is preferably, for example, phenyl or naphthyl.

In Formulae (c1) and (c2), $R^{c3}$ is preferably a hydrogen atom, methyl, ethyl, n-propyl, isopropyl, n-butyl, 2-cyclopentylethyl, 2-cyclobutylethyl, cyclohexylmethyl, phenyl, benzyl, methylphenyl, or naphthyl, and more preferably methyl or phenyl.

Preferred examples of the compound of Formula (c2) with $R^{c1}$ being the group of Formula (c3) include the compounds shown below.

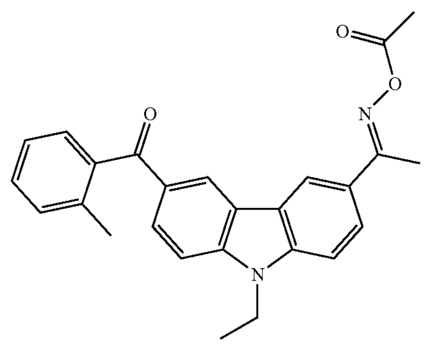

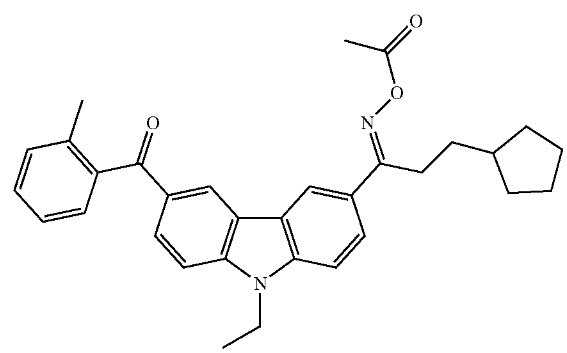
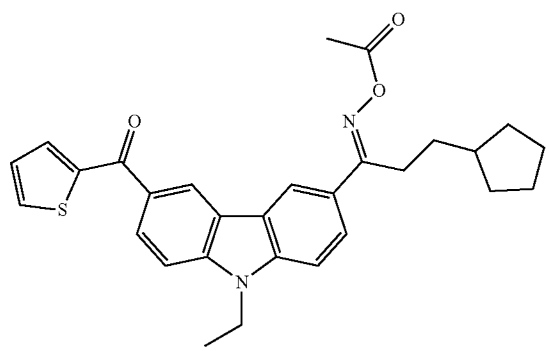
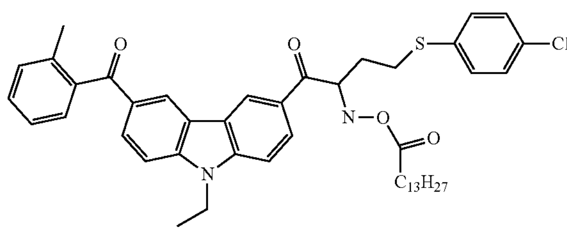
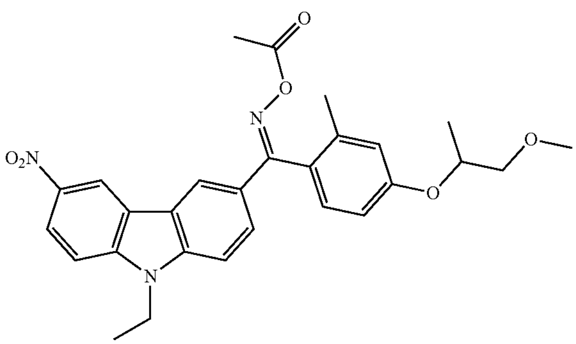
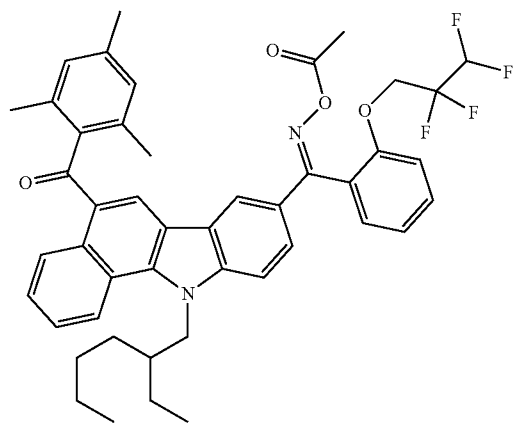
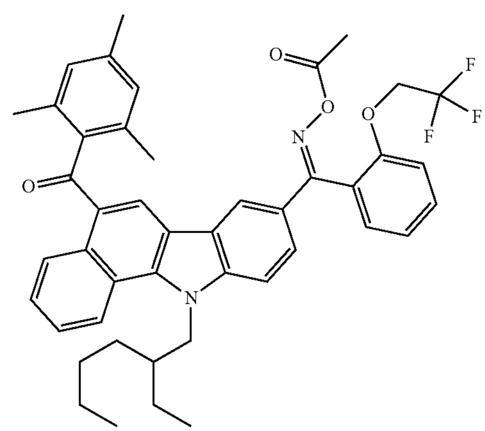
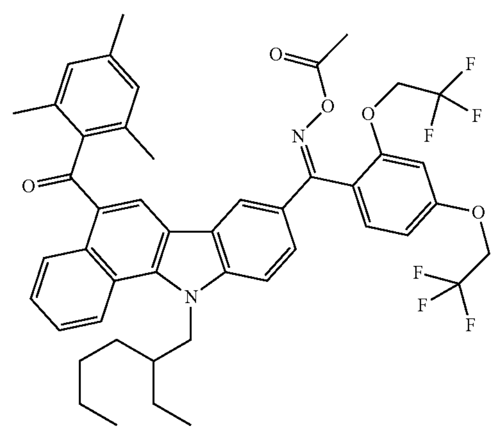
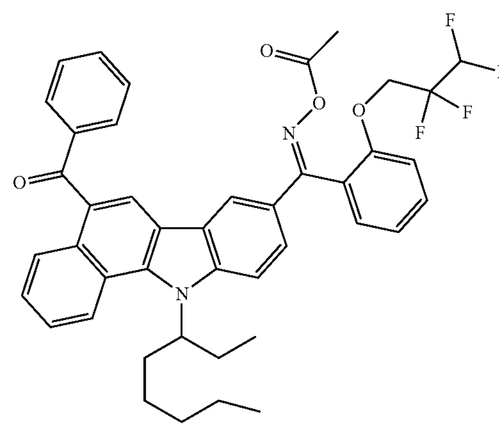
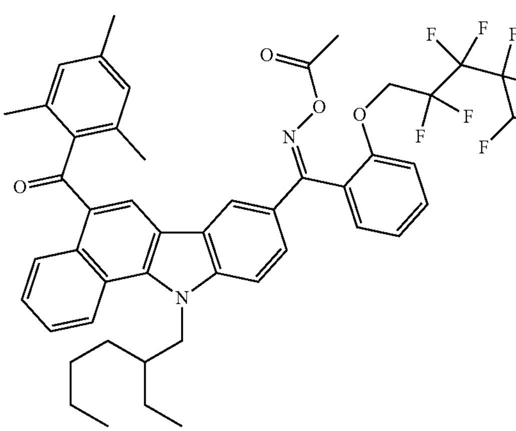

-continued
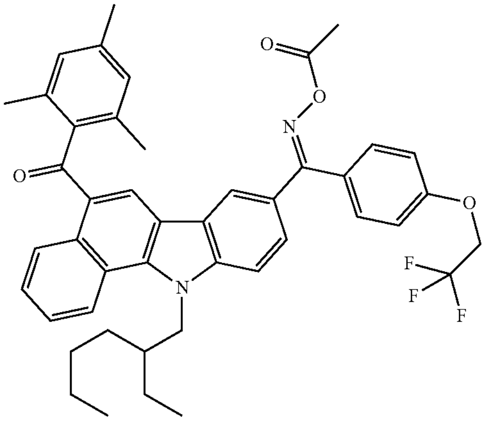
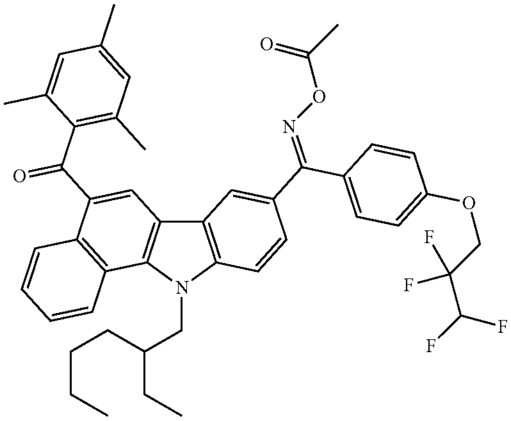
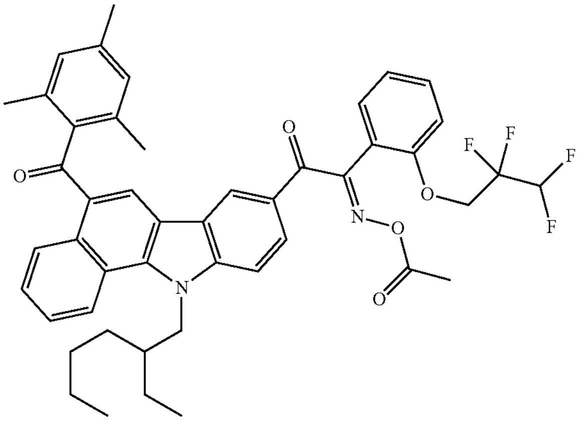
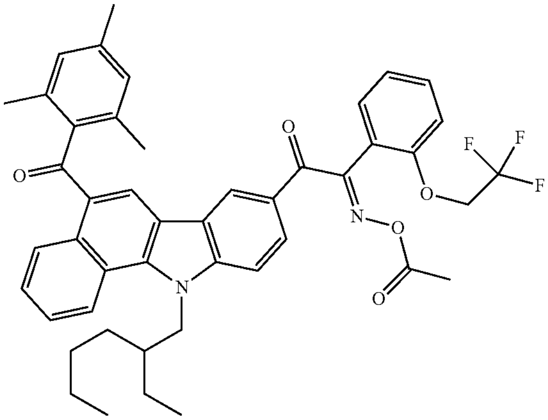
-continued
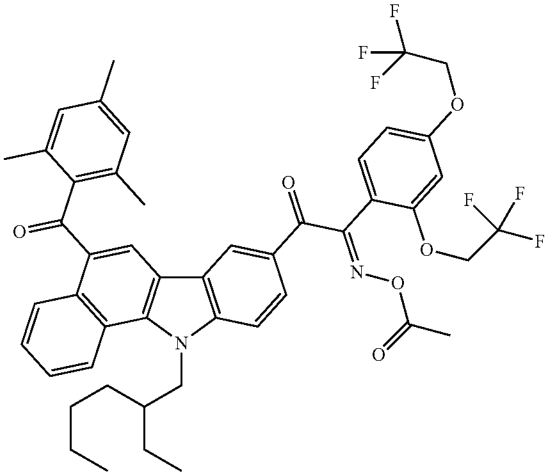
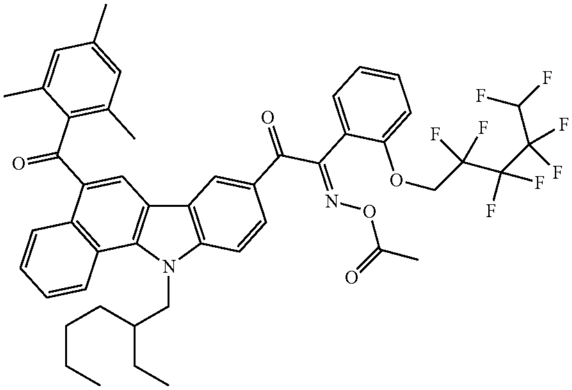
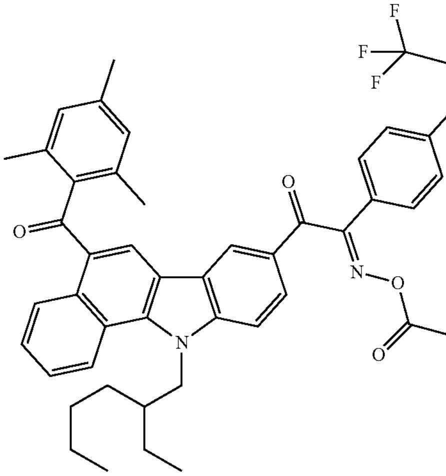

-continued
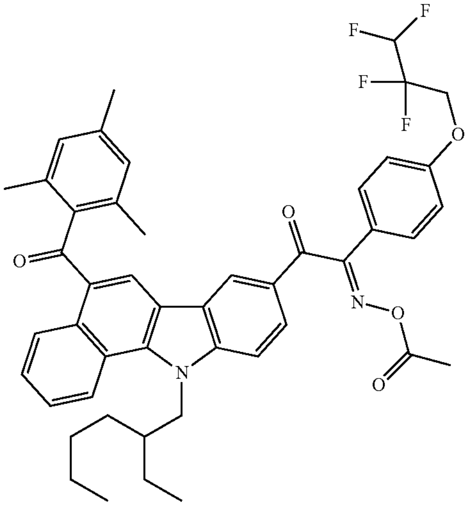
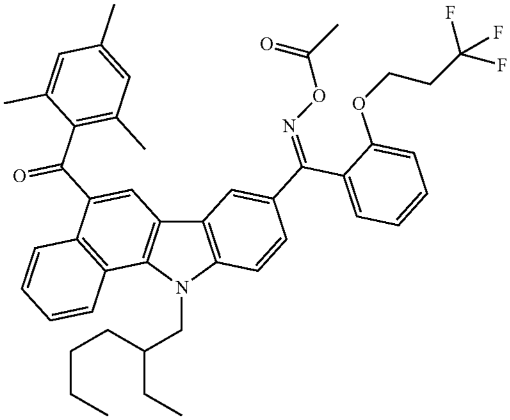
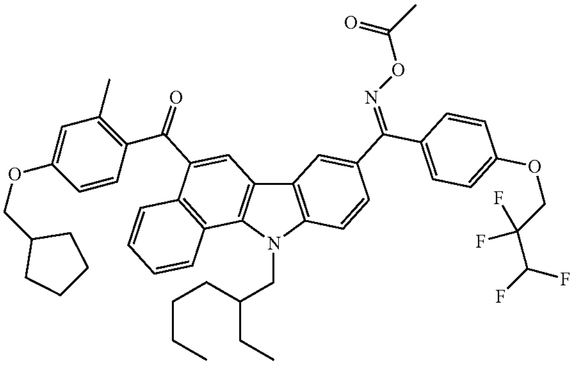
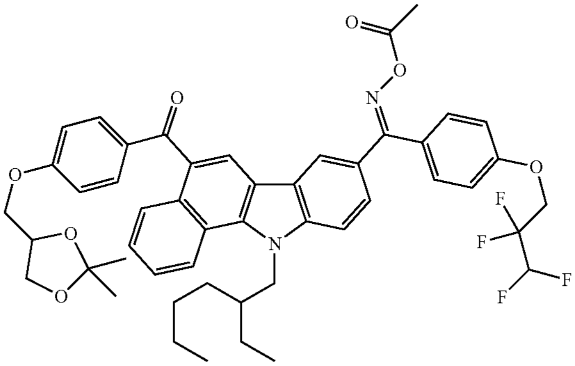
-continued
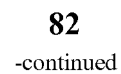
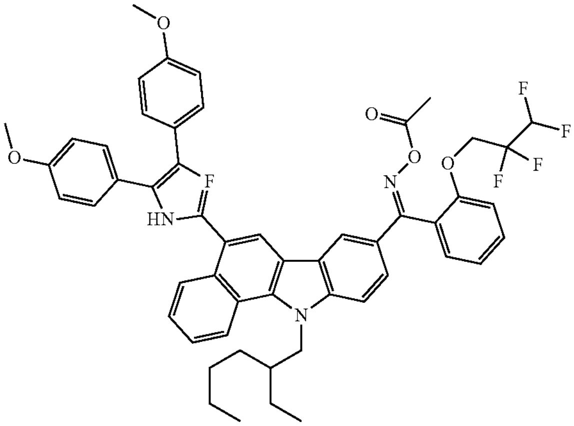
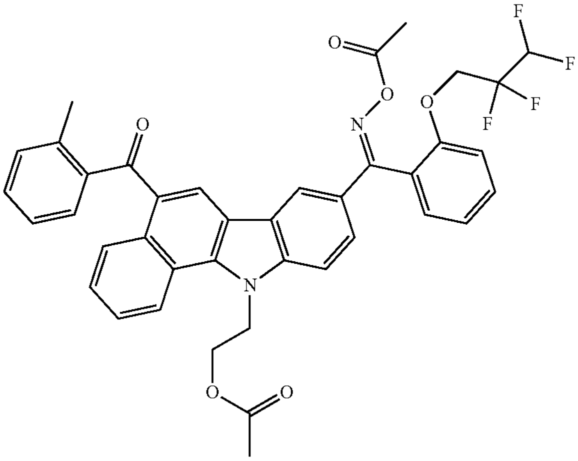
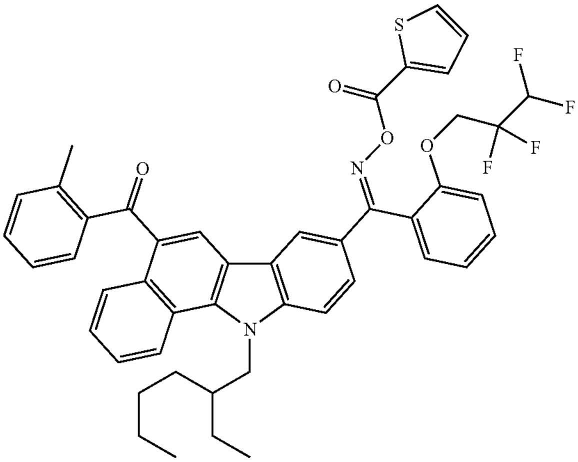

-continued
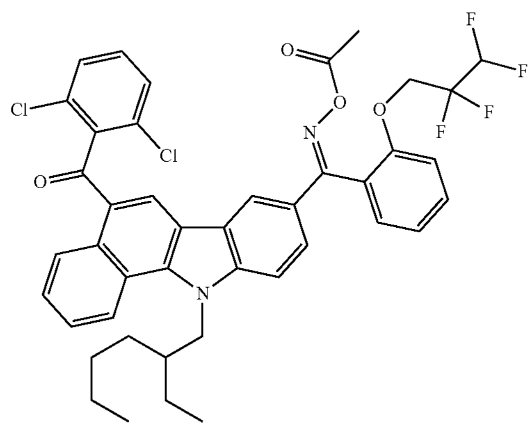
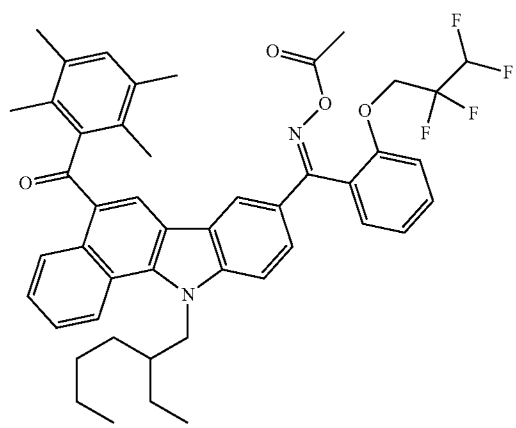
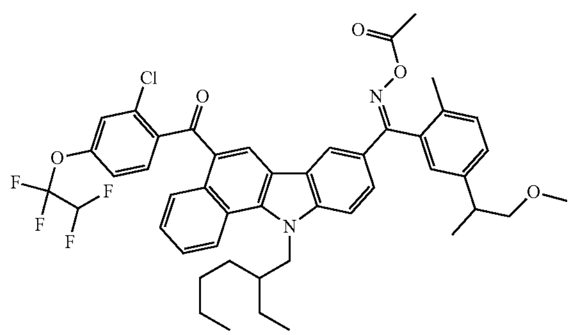
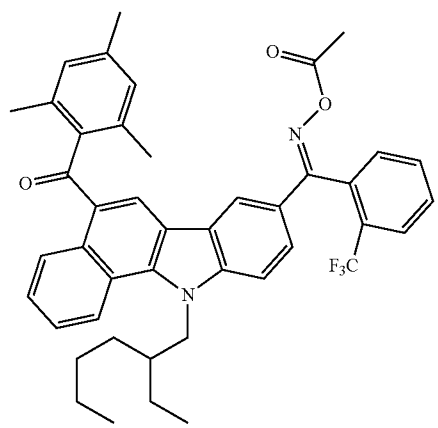
-continued
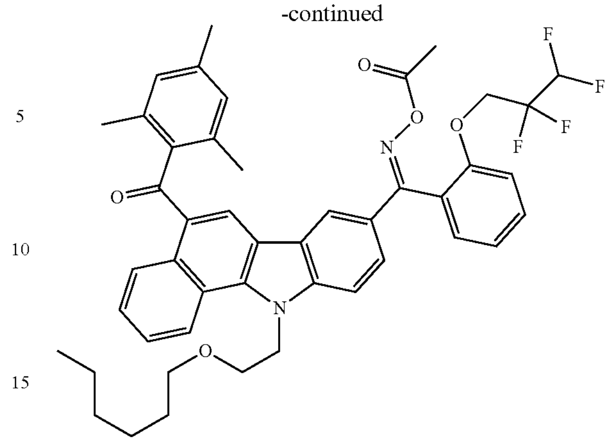
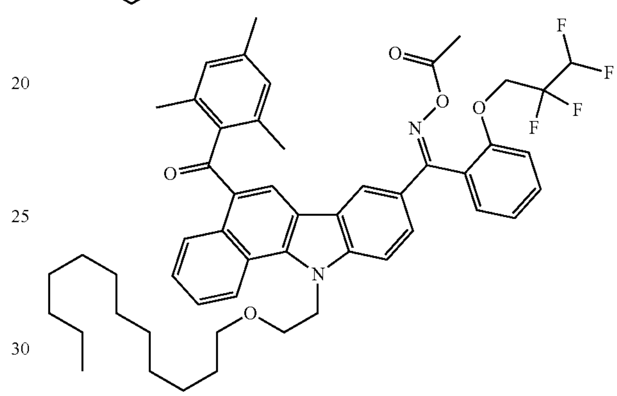
Preferred examples of the compound of Formula (c2) with $R^{c1}$ being the group of Formula (c4) include the compounds shown below.
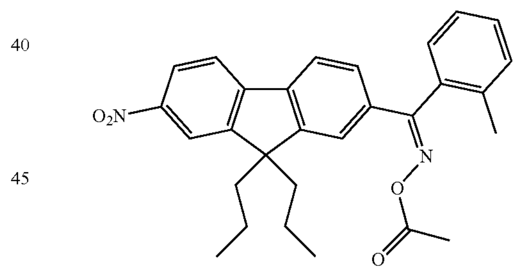
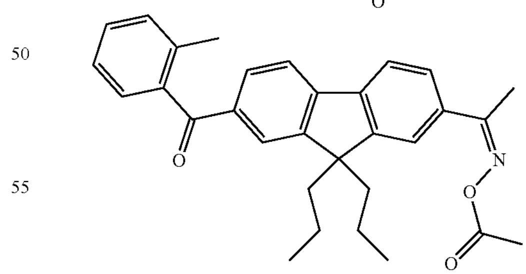
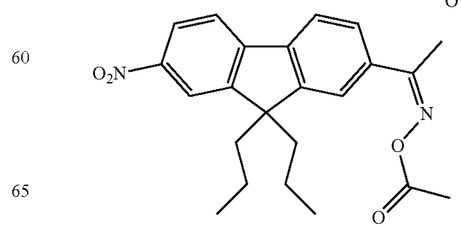

-continued
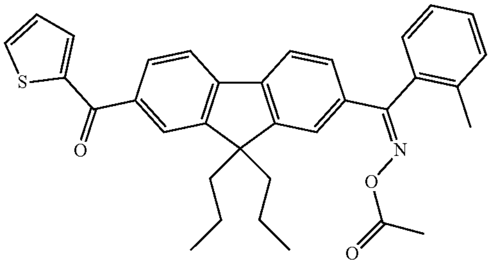
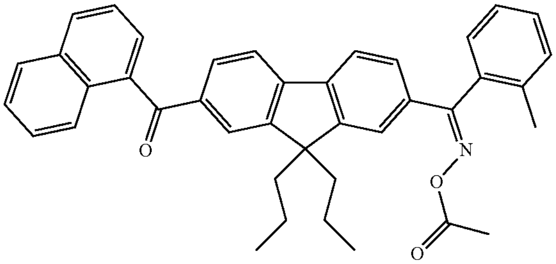
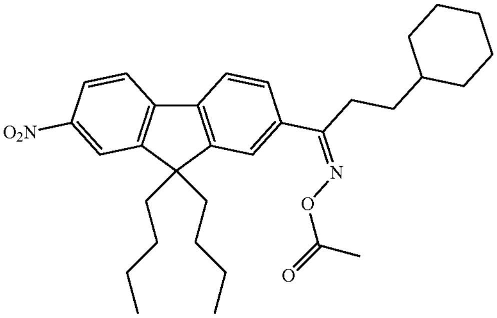
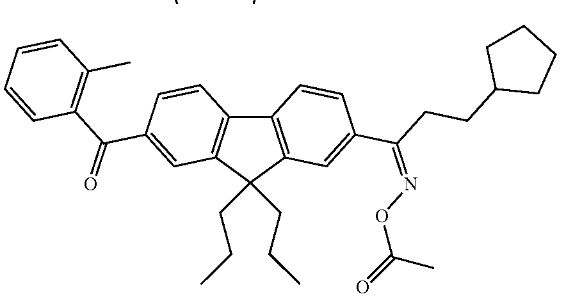
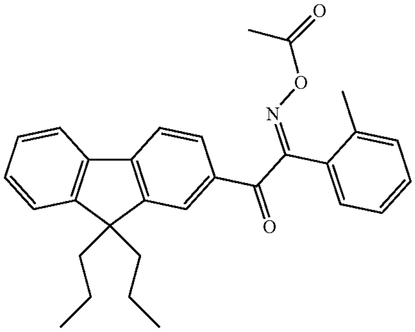
-continued
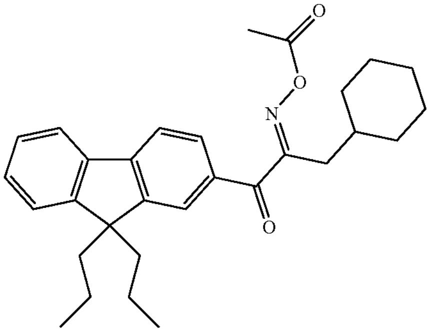
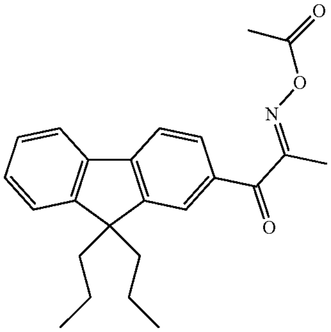
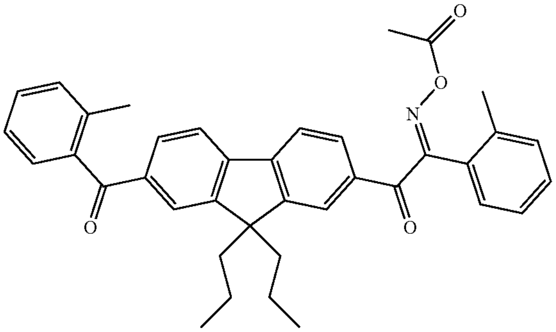
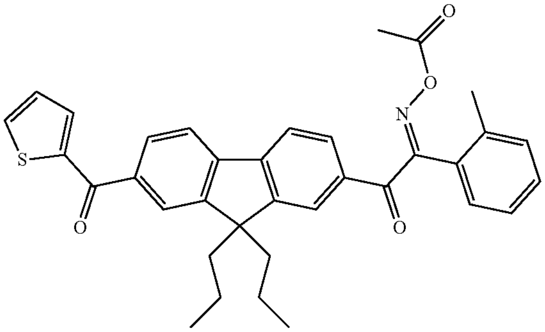
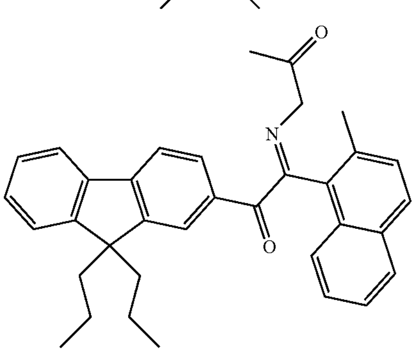

-continued
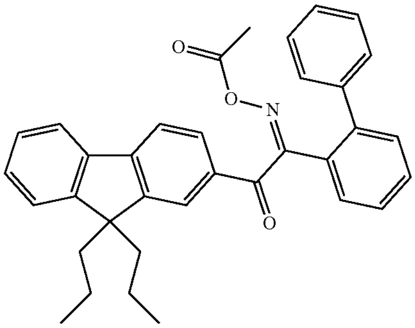
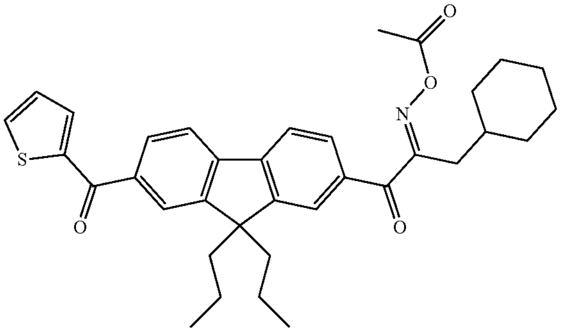
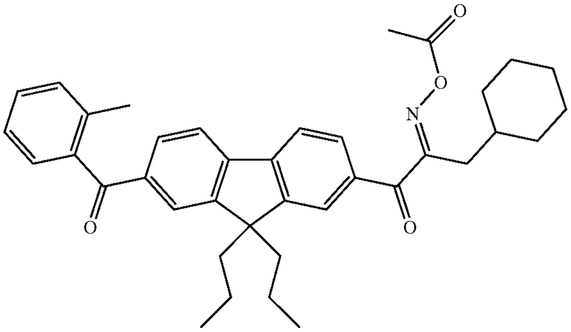
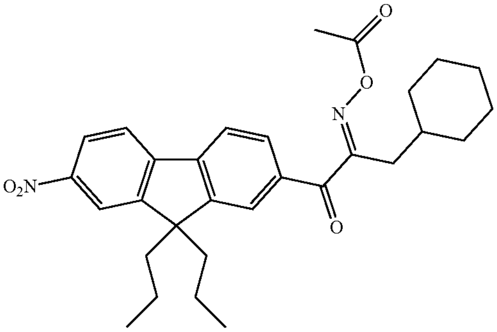
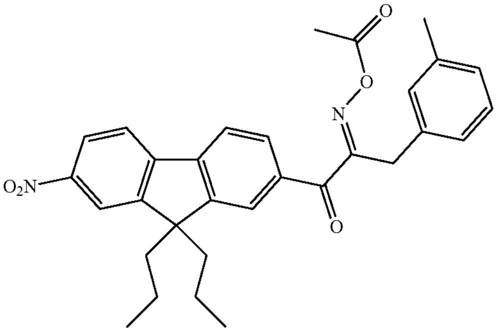
-continued
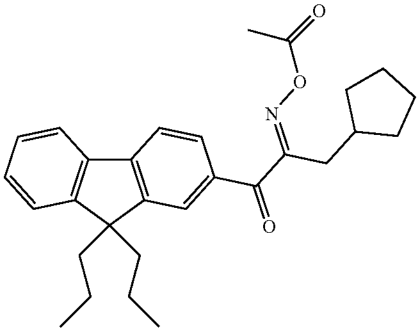
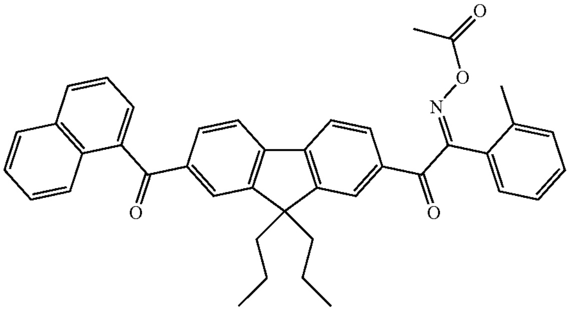
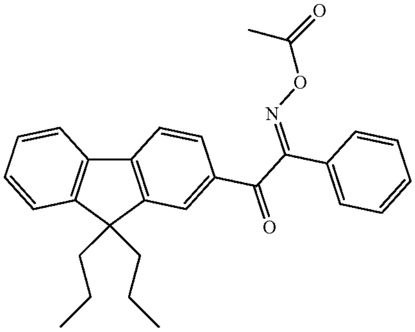
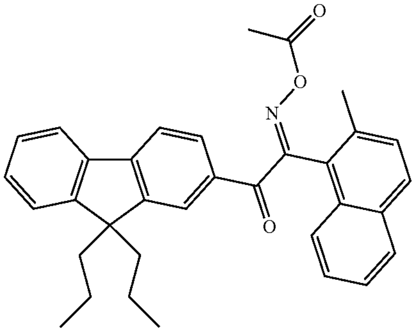
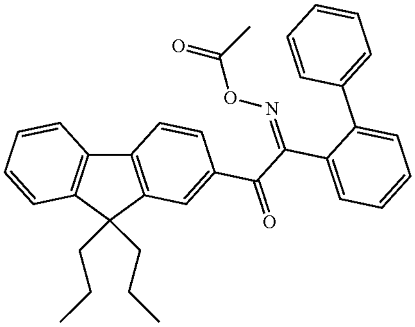

-continued
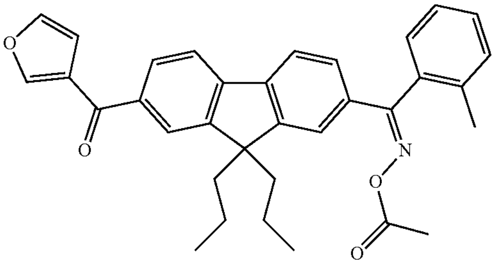
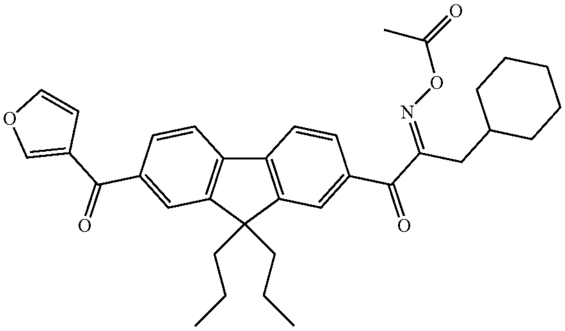
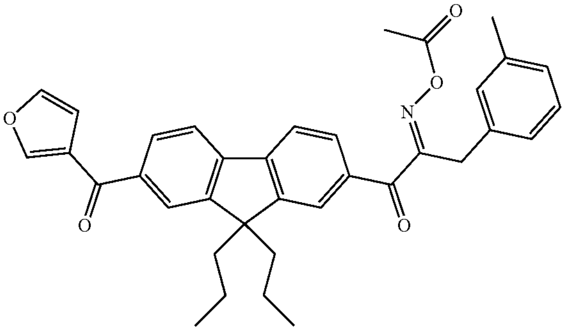
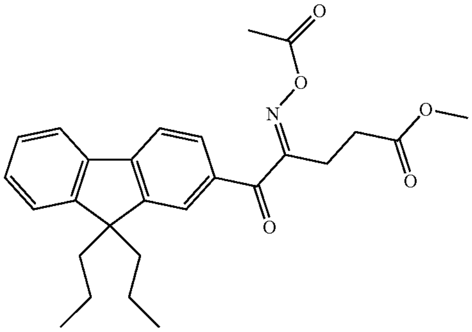
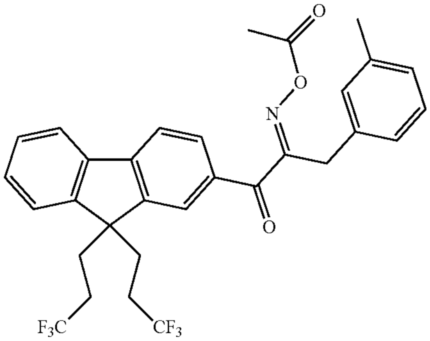
-continued
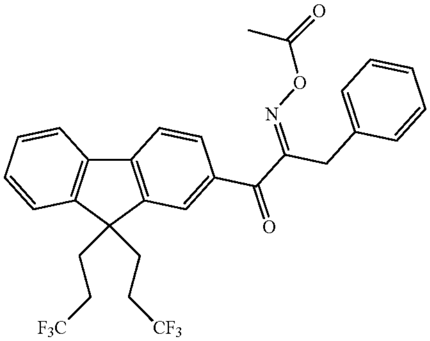
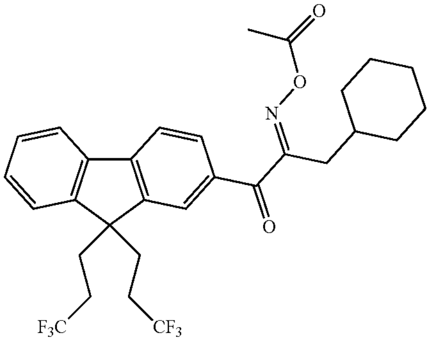
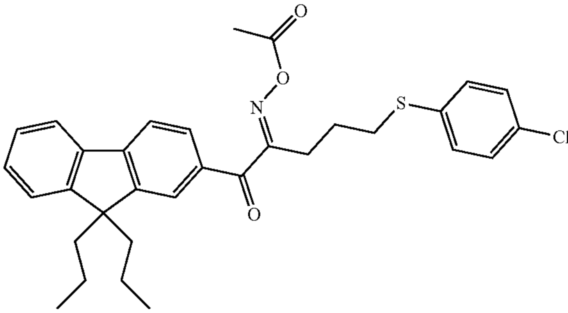
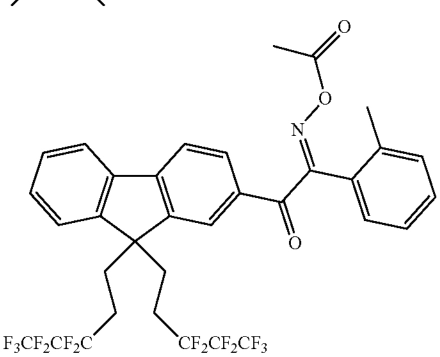
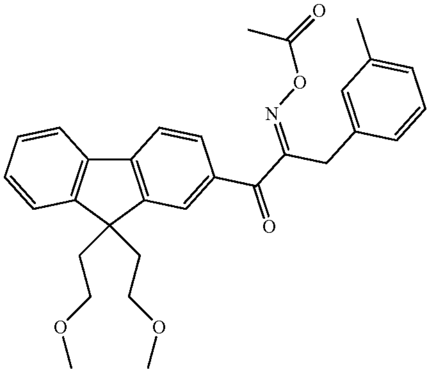

-continued
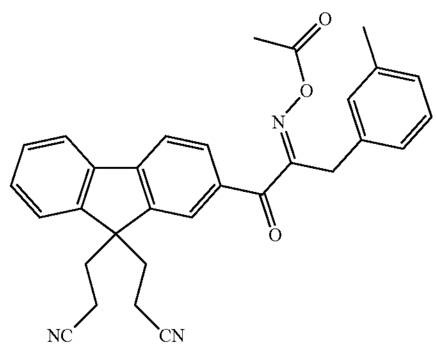
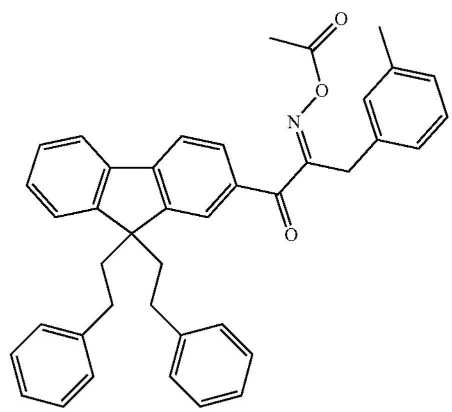
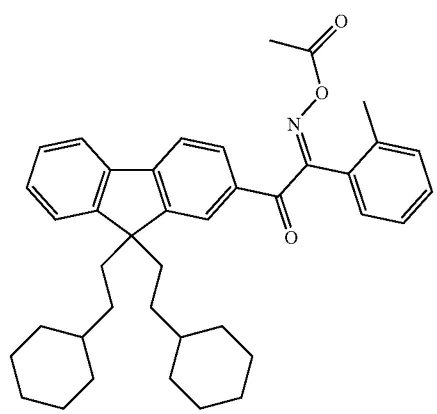
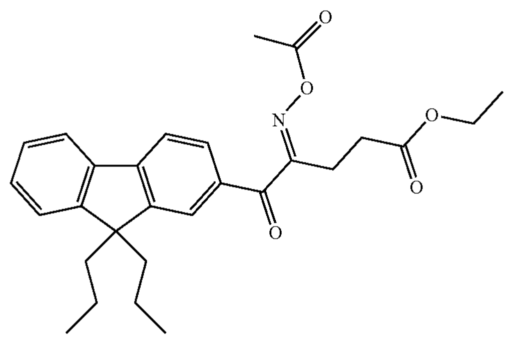
-continued
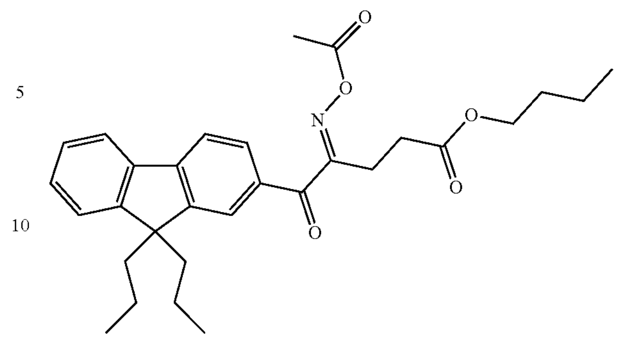
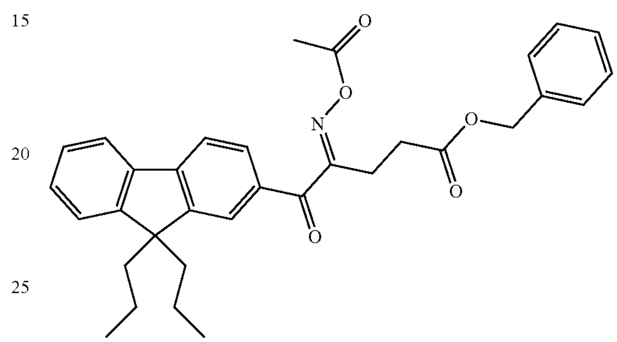
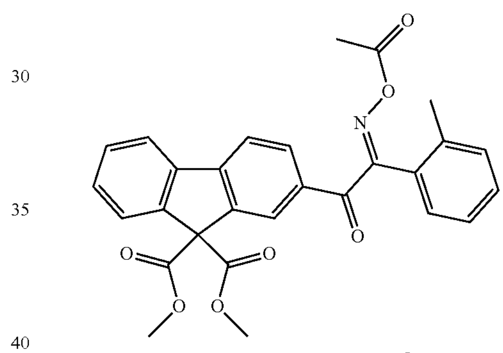
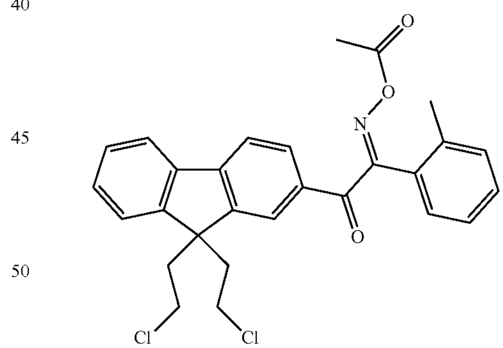
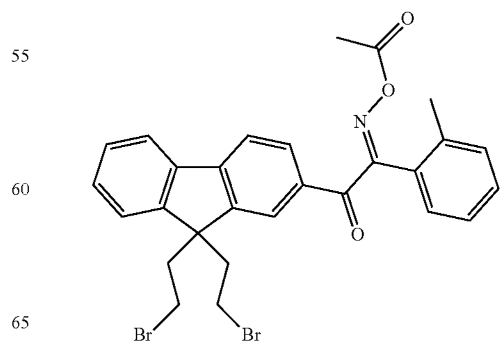

-continued
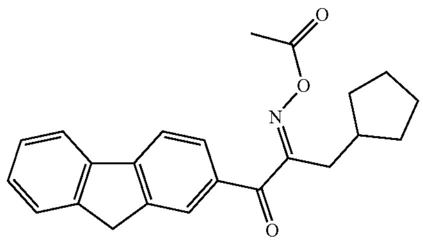
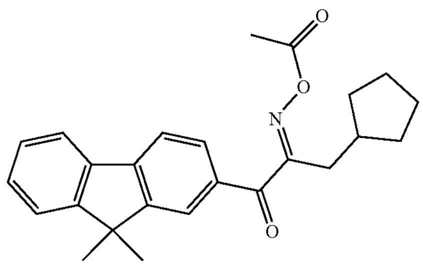
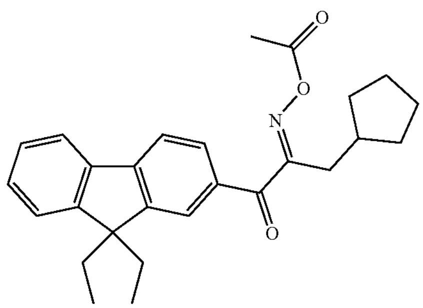
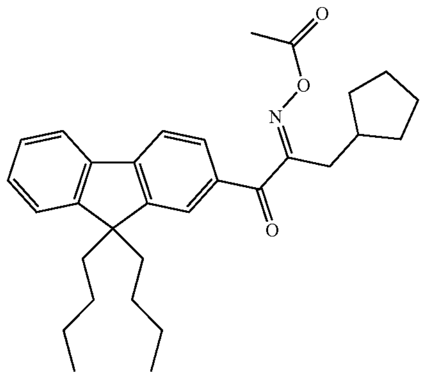
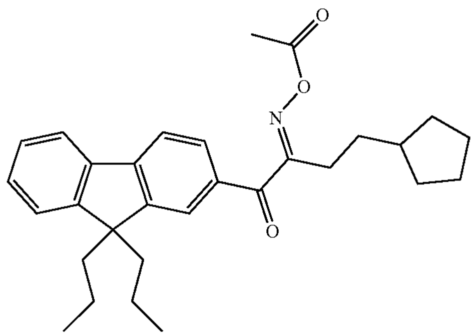
-continued
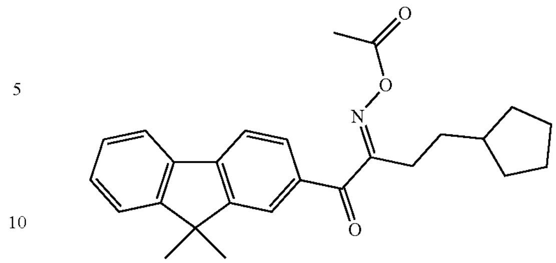
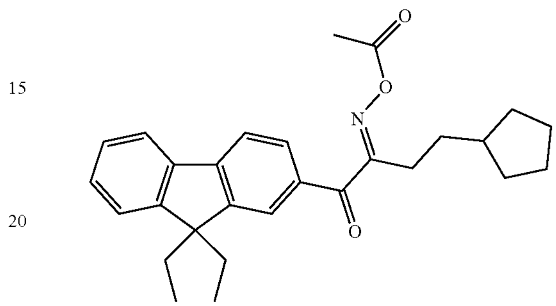
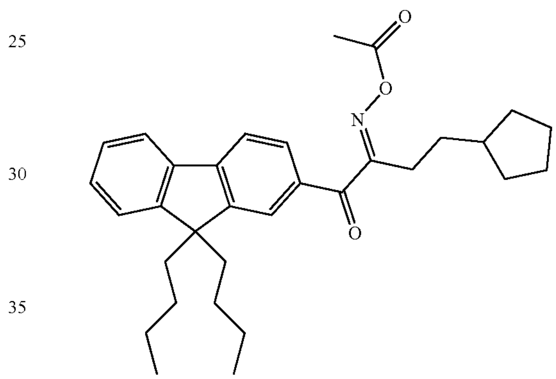
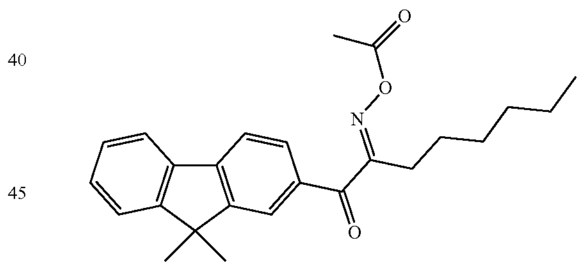
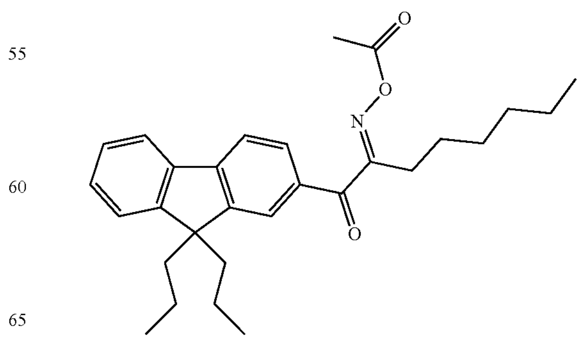

-continued
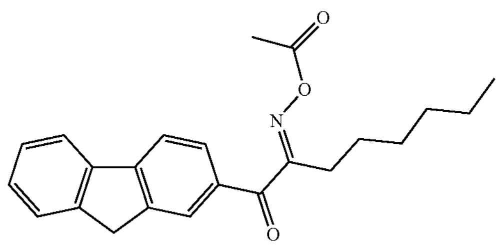
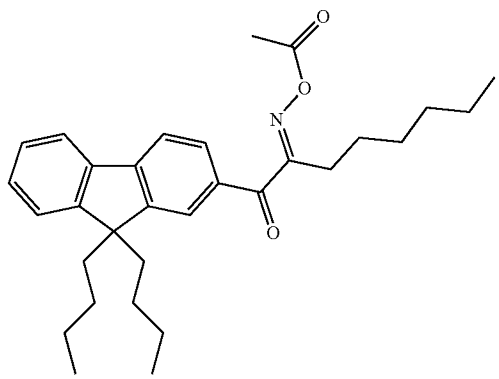
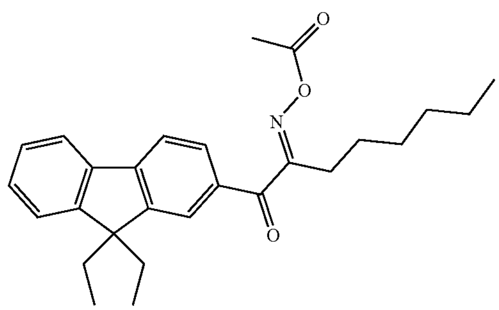
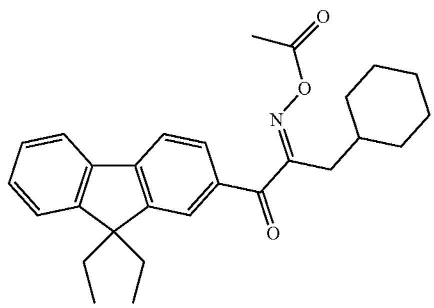
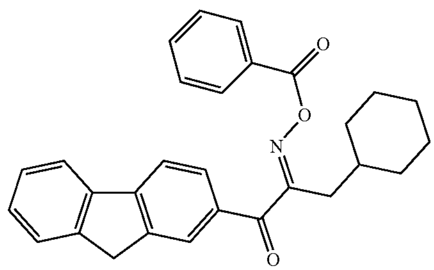
-continued
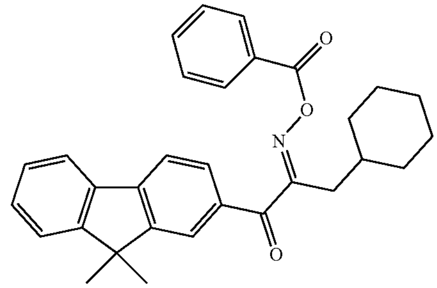
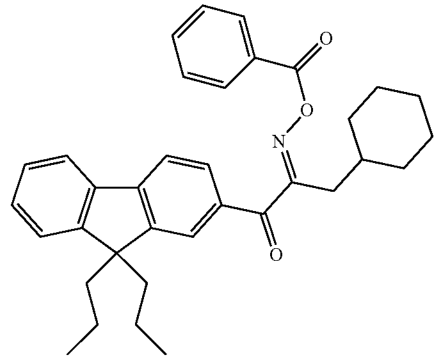
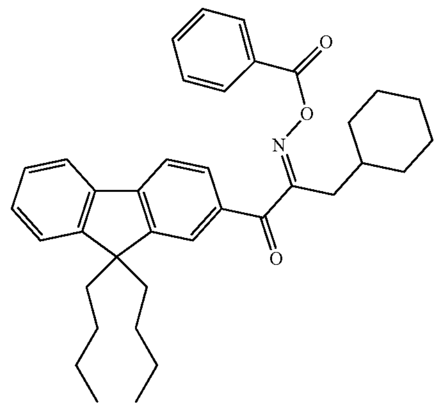
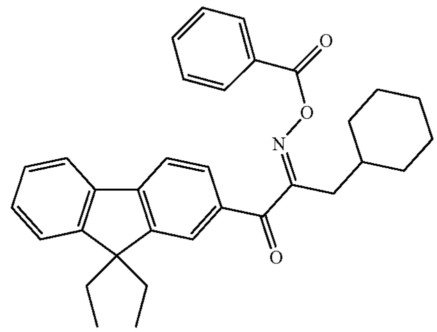
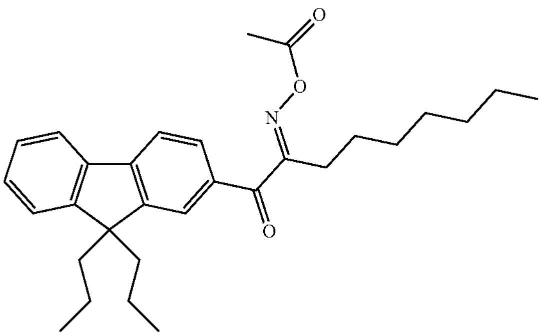

-continued
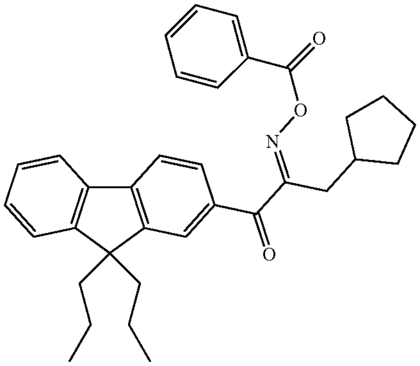
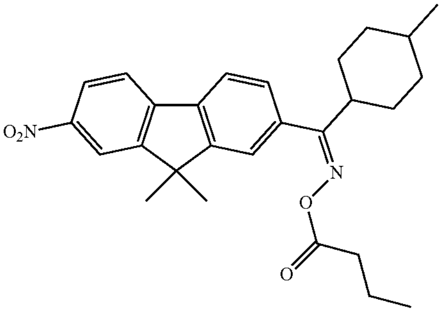
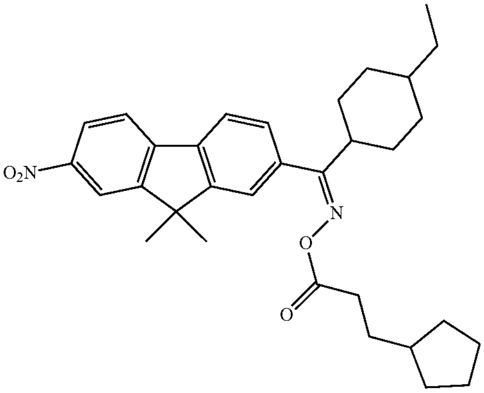
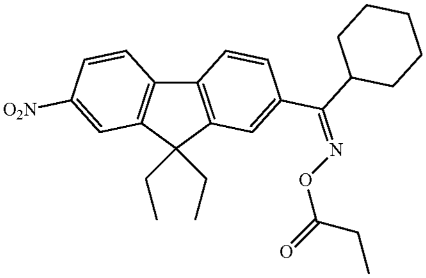
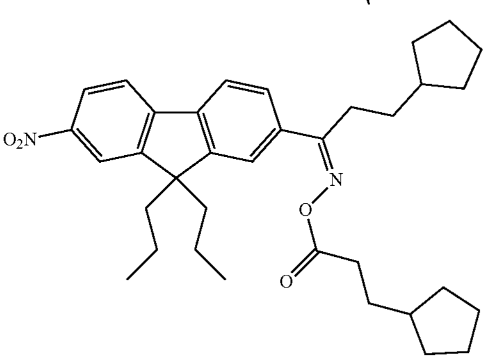
-continued
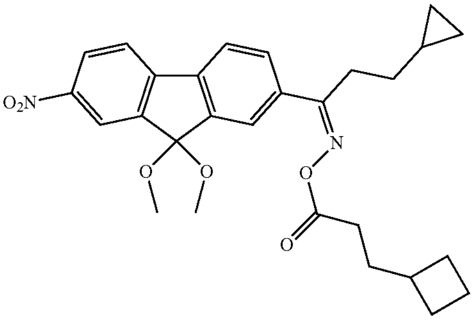
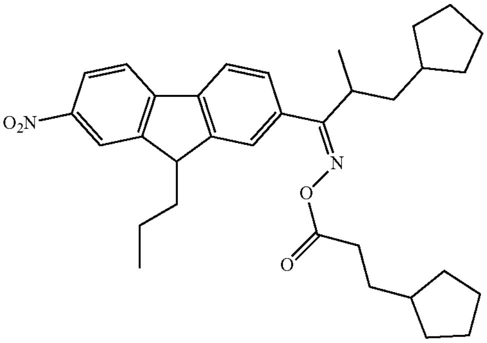
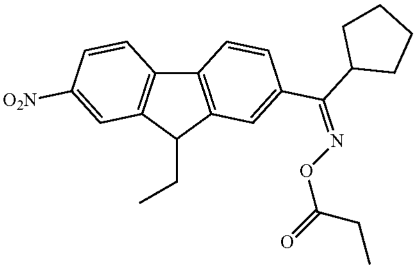
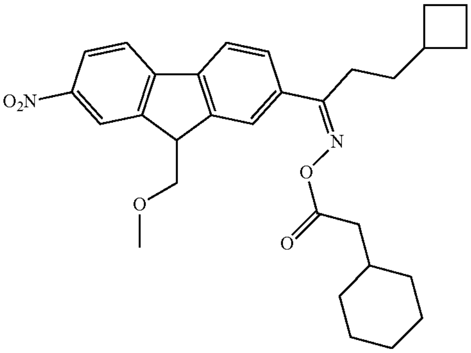
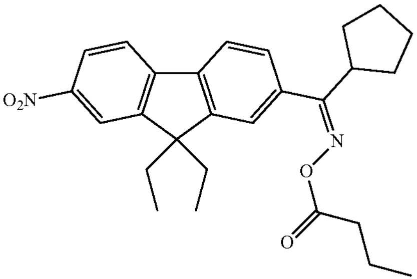

-continued
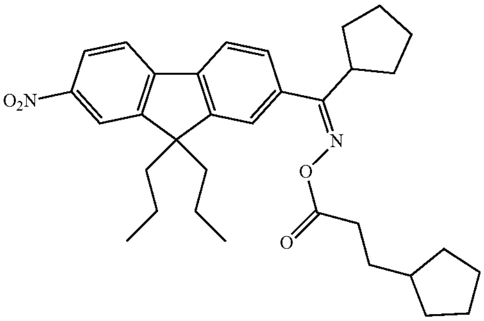
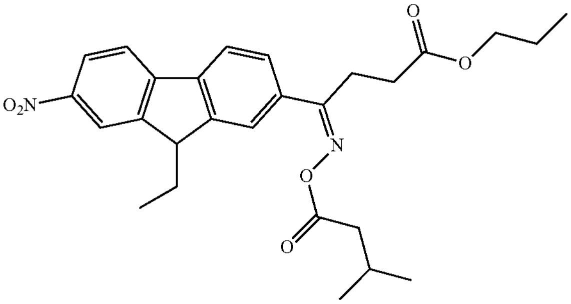
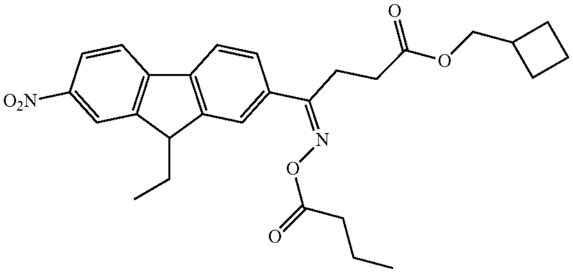
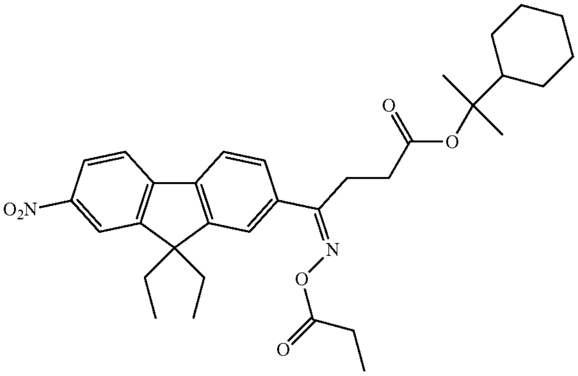
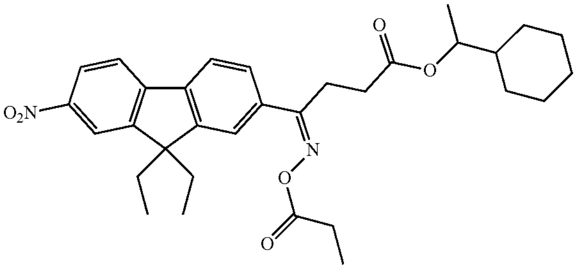
-continued
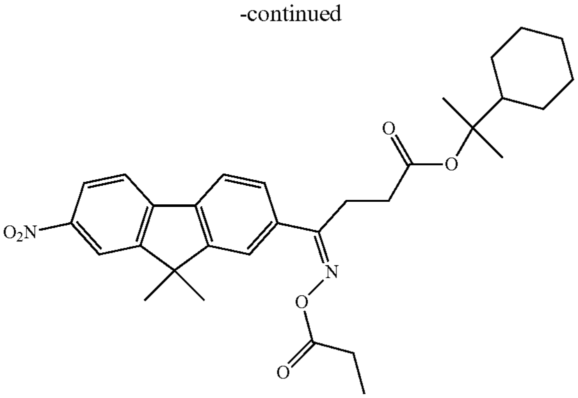
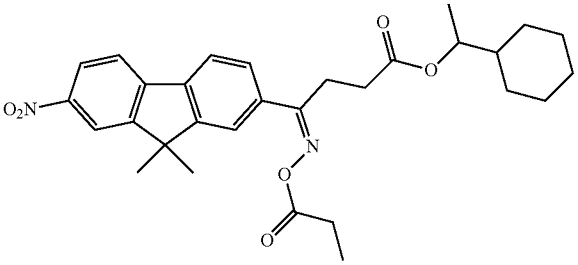
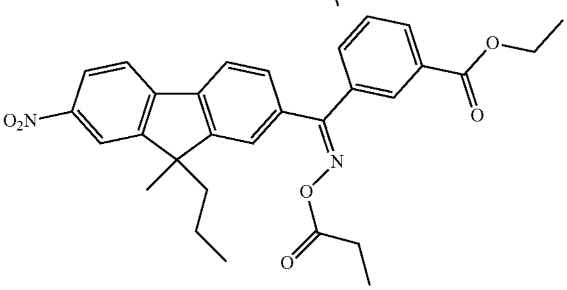
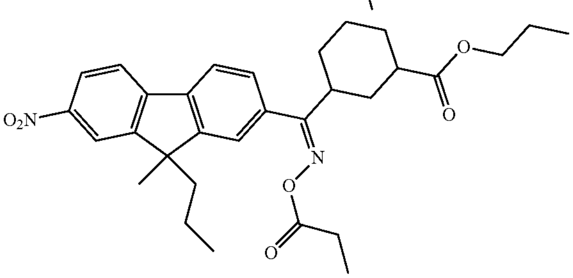
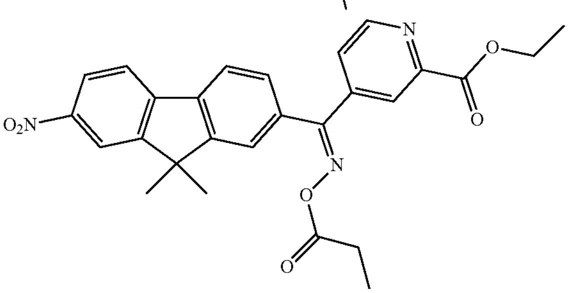
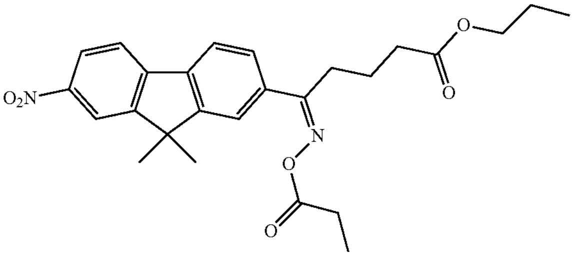

-continued
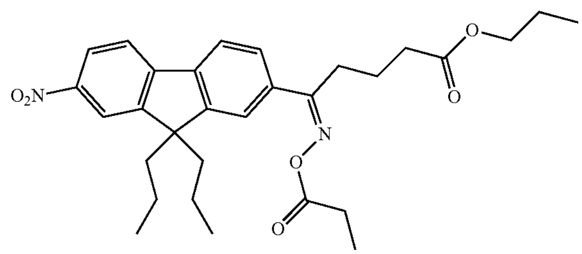
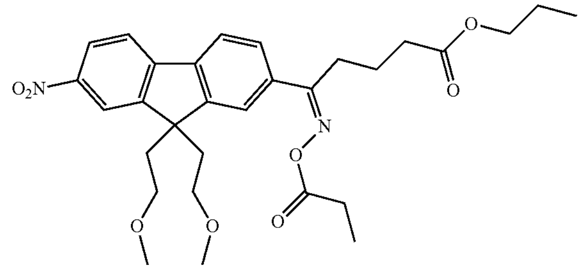
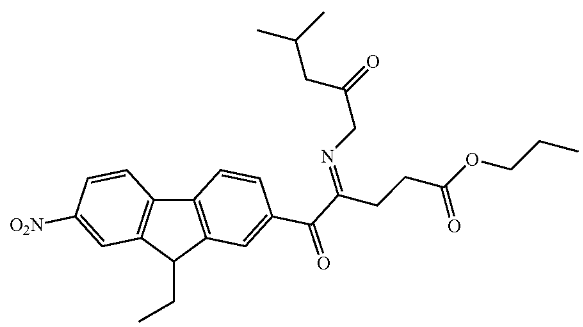
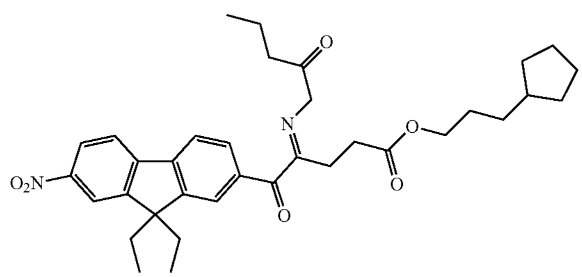
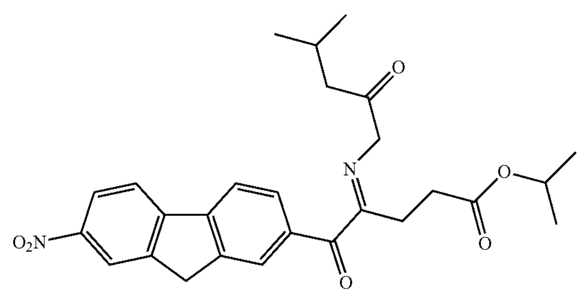
-continued
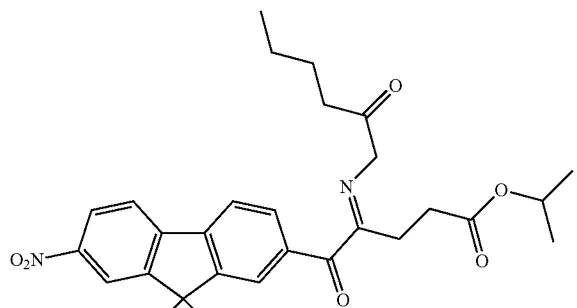
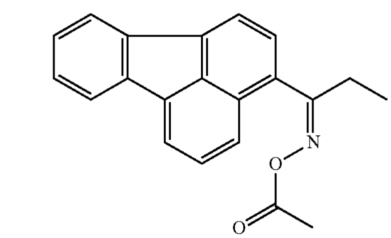
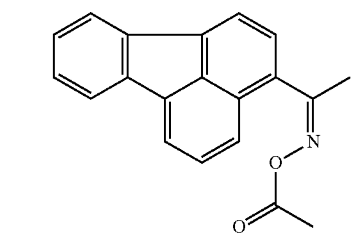
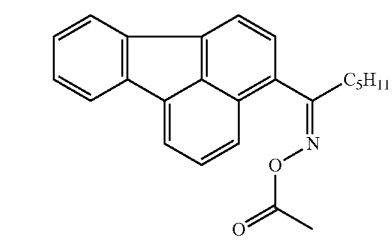
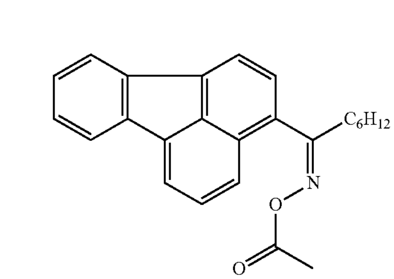

Preferred examples of the compound of Formula (c2) with $R^{c1}$ being the group of Formula (c5) include the compounds shown below.

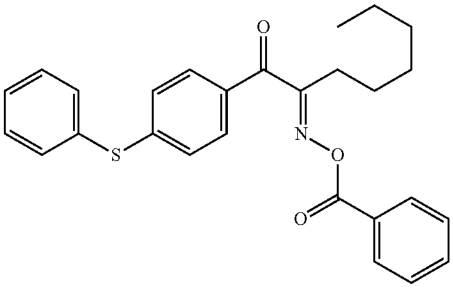

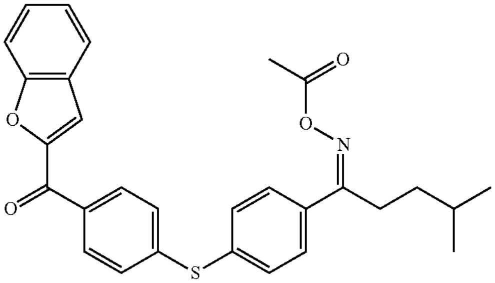

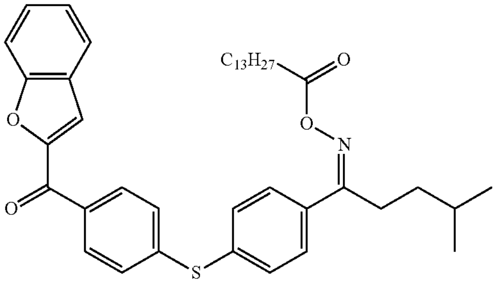

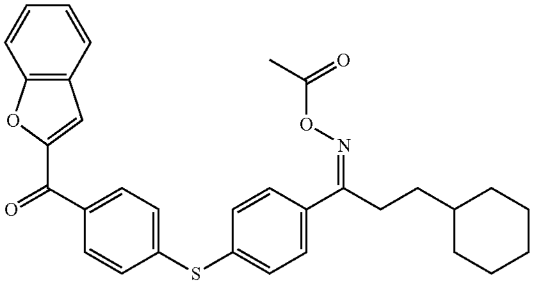

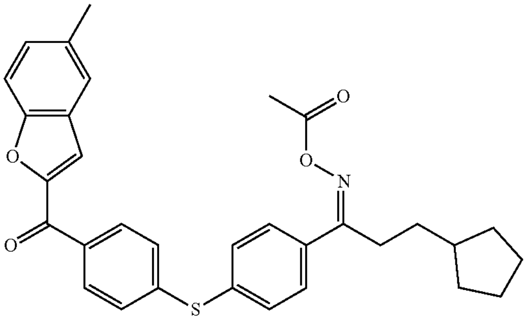

-continued

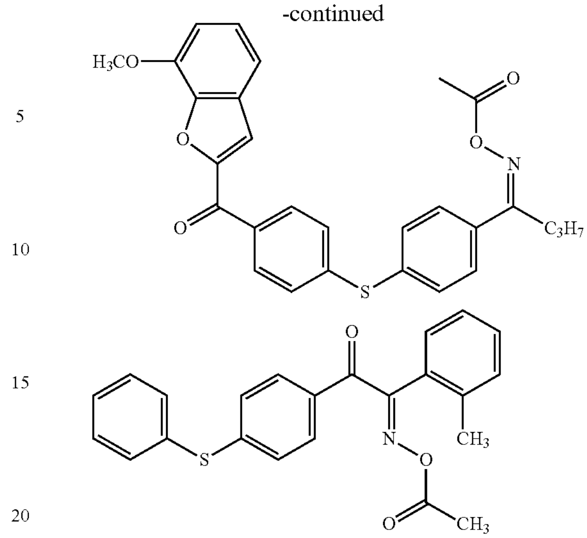

The radical polymerization initiating agent (C1) is also preferably a phosphine oxide compound, which can form a photosensitive composition having good curability even at depth. The phosphine oxide compound preferably has a partial substructure of Formula (c9) below.

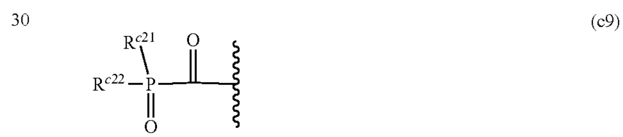

(c9)

In Formula (c9), $R^{c21}$ and $R^{c22}$ are each independently an alkyl group, a cycloalkyl group, an aryl group, an aliphatic acyl group having 2 or more and 20 or less carbon atoms, or an aromatic acyl group having 7 or more and 20 or less carbon atoms, provided that $R^{c21}$ and $R^{c22}$ are not simultaneously aliphatic acyl groups or aromatic acyl groups.

The alkyl group of $R^{c21}$ or $R^{c22}$ preferably has 1 or more and 12 or less carbon atoms, more preferably 1 or more and 8 or less carbon atoms, even more preferably 1 or more and 4 or less carbon atoms. The alkyl group of $R^{c21}$ or $R^{c22}$ may be linear or branched. Examples of the alkyl group include methyl, ethyl, n-propyl, isopropyl, n-butyl, isobutyl, sec-butyl, tert-butyl, n-pentyl, isopentyl, tert-pentyl, n-hexyl, n-heptyl, n-octyl, 2,4,4-trimethylpentyl, 2-ethylhexyl, n-nonyl, n-decyl, n-undecyl, and n-dodecyl.

The cycloalkyl group of $R^{c21}$ or $R^{c22}$ preferably has 5 or more and 12 or less carbon atoms. Examples of the cycloalkyl group include cyclopentyl, cyclohexyl, cycloheptyl, cyclooctyl, cyclononyl, cyclodecyl, cycloundecyl, and cyclododecyl.

The aryl group of $R^{c21}$ or $R^{c22}$ preferably has 6 or more and 12 or less carbon atoms. The aryl group may have a substituent. Examples of the substituent include a halogen atom, an alkyl group having 1 or more and 4 or less carbon atoms, and an alkoxy group having 1 or more and 4 or less carbon atoms. Examples of the aryl group include phenyl and naphthyl.

The aliphatic acyl group of $R^{c21}$ or $R^{c22}$ has 2 or more and 20 or less carbon atoms, preferably 2 or more and 12 or less carbon atoms, more preferably 2 or more and 8 or less carbon atoms, even more preferably 2 or more and 6 or less carbon atoms. The aliphatic acyl group may be linear or branched. Examples of the aliphatic acyl group include acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, and icosanoyl.

The aromatic acyl group of $R^{c21}$ or $R^{c22}$ has 7 or more and 20 or less carbon atoms. The aromatic acyl group may have a substituent. Examples of the substituent include a halogen atom, an alkyl group having 1 or more and 4 or less carbon atoms, and an alkoxy group having 1 or more and 4 or less carbon atoms. Examples of the aromatic acyl group include benzoyl, o-tolyl, m-tolyl, p-tolyl, 2,6-dimethylbenzoyl, 2,6-dimethoxybenzoyl, 2,4,6-trimethylbenzoyl, α-naphthoyl, and β-naphthoyl.

Preferred examples of the phosphine oxide compound having a partial structure of Formula (c9) include 2,4,6-trimethylbenzoyldiphenylphosphine oxide, bis(2,4,6-trimethylbenzoyl)-phenylphosphine oxide, and bis(2,6-dimethoxybenzoyl)-2,4,4-trimethyl-pentylphosphine oxide. In order for the photosensitive composition to have good curability even at depth, the phosphine oxide compound having a partial structure of Formula (c9) is also preferably used in combination with an a-hydroxyalkylphenone initiating agent, such as 2-hydroxy-2-methylpropiophenone. In a case where the phosphine oxide compound having a partial structure of Formula (c9) is used in combination with an α-hydroxyalkylphenone initiating agent, such as 2-hydroxy-2-methylpropiophenone, the ratio of the mass of the phosphine oxide compound having a partial structure of Formula (c9) to the total mass of them is preferably 20 mass % or more and 80 mass % or less, more preferably 30 mass % or more and 70 mass % or less, even more preferably 40 mass % or more and 60 mass % or less.

The cationic polymerization initiating agent (C2) may be any conventionally-known one. Typical examples of the cationic polymerization initiating agent (C2) include onium salts. The cationic polymerization initiating agent (C2) may be an oxonium salt, an ammonium salt, a phosphonium salt, a sulfonium salt, or an iodonium salt, and is preferably a sulfonium salt or an iodonium salt, more preferably a sulfonium salt.

The content of the initiating agent (C) in the photosensitive composition may be any level. The content of the initiating agent (C) may be appropriately selected depending on the type of the radically or cationically polymerizable group or the type of the initiating agent (C). The content of the initiating agent (C) in the photosensitive composition is preferably 0.01 parts by mass or more and 20 parts by mass or less, more preferably 0.1 parts by mass or more and 15 parts by mass or less, even more preferably 1 part by mass or more and 10 parts by mass or less, based on the mass calculated by subtracting the mass of the solvent (S) described from the mass of the photosensitive composition, which corresponds to 100 parts by mass.

Plasticizing Agent (D)

The photosensitive composition may contain a plasticizing agent (D). The plasticizing agent (D) should be a component that will provide the photosensitive composition with a reduced viscosity and will not significantly degrade the properties (e.g., high refractive index) of materials produced using the photosensitive composition.

The plasticizing agent (D) is preferably a compound of Formula (d-1) below.

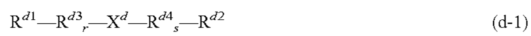

$R^{d1}—R^{d3}_{r}—X^{d}—R^{d4}_{s}—R^{d2}$ (d-1)

In Formula (d-1), $R^{d1}$ and $R^{d2}$ are each independently a phenyl group optionally having 1 or more and 5 or less substituents each selected from the group consisting of an alkyl group having 1 or more and 4 or less carbon atoms, an alkoxy group having 1 or more and 4 or less carbon atoms, and a halogen atom, $R^{d3}$ and $R^{d4}$ are each independently a methylene group or an ethane-1,2-diyl group, r and s are each independently 0 or 1, and $X^d$ is an oxygen atom or a sulfur atom.

The photosensitive composition containing such a plasticizing agent (D) will have a reduced viscosity and can form materials with high refractive index and other properties remaining not significantly degraded. To provide the photosensitive composition with a reduced viscosity, the plasticizing agent (D) preferably has a viscosity of 10 cP or less, more preferably 8 cP or less, even more preferably 6 cP or less, as measured with an E-type viscometer at 25° C. The plasticizing agent (D) also preferably has a boiling point of 250° C. or more, more preferably 260° C. or more, under atmospheric pressure, so that it can be less volatile and easily and constantly effective in providing the photosensitive composition with a reduced viscosity. The upper limit of the boiling point of the plasticizing agent (D) under atmospheric pressure is typically, but not limited to, 300° C. or less or 350° C. or less.

In Formula (d-1), $R^{d1}$ and $R^{d2}$ are each independently a phenyl group optionally having 1 or more and 5 or less substituents. The substituent that may be bonded to the phenyl group is a group selected from the group consisting of an alkyl group having 1 or more and 4 or less carbon atoms, an alkoxy group having 1 or more and 4 or less carbon atoms, and a halogen atom. The phenyl group may have any suitable number of substituents. The phenyl group may have one or more and five or less substituents and preferably has one or two substituents, more preferably one substituent. For the photosensitive composition to have a reduced viscosity, $R^{d1}$ and $R^{d2}$ are each preferably an unsubstituted phenyl group.

The substituent alkyl group having 1 or more and 4 or less carbon atoms may be methyl, ethyl, n-propyl, isopropyl, n-butyl, isobutyl, sec-butyl, or tert-butyl. The substituent alkoxy group having 1 or more and 4 or less carbon atoms may be methoxy, ethoxy, n-propyloxy, isopropyloxy, n-butyloxy, isobutyloxy, sec-butyloxy, or tert-butyloxy. The substituent halogen atom may be fluorine, chlorine, bromine, or iodine.

In Formula (d-1), $R^{d3}$ and $R^{d4}$ are each independently a methylene group or an ethane-1,2-diyl group, and r and s are each independently 0 or 1. In Formula (d-1), $X^d$ is an oxygen atom or a sulfur atom.

Preferred examples of the compound of Formula (d-1) described above include diphenyl ether, diphenyl sulfide, dibenzyl ether, dibenzyl sulfide, diphenethyl ether, and diphenethyl sulfide. Among them, diphenyl sulfide and/or dibenzyl ether is more preferred.

For both good viscosity control and good dispersibility of the inorganic fine particles (B), the content of the plasticizing agent (D) in the photosensitive composition is preferably more than 0 mass % and 35 mass % or less, more preferably 5 mass % or more and 15 mass % or less, based on the mass of the photosensitive composition.

Nitrogen-Containing Compound (E)

For ease of producing materials with less localized inorganic fine particles (B) from the photosensitive composition, the photosensitive composition may contain a nitrogen-containing compound (E), such as an amine compound (E1) of Formula (e1) below and/or an imine compound (E2) of Formula (e2) below.

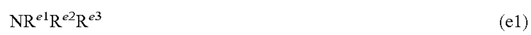

$NR^{e1}R^{e2}R^{e3}$ (e1)

In Formula (e1), $R^{e1}$, $R^{e2}$, and $R^{e3}$ are each independently a hydrogen atom or an organic group.

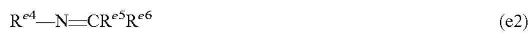

$R^{e4}—N═CR^{e5}R^{e6}$ (e2)

In Formula (e2), $R^{e4}$, $R^{e5}$, and $R^{e6}$ are each independently a hydrogen atom or an organic group.

In Formulae (e1) and (e2), the organic group of $R^{e1}$, $R^{e2}$, $R^{e3}$, $R^{e4}$, $R^{e5}$, or $R^{e6}$ may be selected from various organic groups that do not compromise the desired effect. The organic group is preferably a carbon atom-containing group and more preferably a group including one or more carbon atoms and at least one atom selected from the group consisting of H, O, S, Se, N, B, P, Si, and halogen. The number of carbon atoms in the carbon atom-containing group is preferably, but not not limited to, 1 or more and 50 or less, more preferably 1 or more and 20 or less. Preferred examples of the organic group include alkyl, cycloalkyl, optionally substituted phenyl, optionally substituted phenylalkyl, optionally substituted naphthyl, optionally substituted naphthylalkyl, and optionally substituted heterocyclyl.

The organic group is preferably an alkyl group having 1 or more and 20 or less carbon atoms, more preferably an alkyl group having 1 or more and 6 or less carbon atoms. The alkyl group may have a linear or branched structure. Examples of the alkyl group include methyl, ethyl, n-propyl, isopropyl, n-butyl, isobutyl, sec-butyl, tert-butyl, n-pentyl, isopentyl, sec-pentyl, tert-pentyl, n-hexyl, n-heptyl, n-octyl, isooctyl, sec-octyl, tert-octyl, n-nonyl, isononyl, n-decyl, and isodecyl. The alkyl group may have a carbon chain containing an ether bond (—O—). Examples of the alkyl group having an ether bond-containing carbon chain include methoxyethyl, ethoxyethyl, methoxyethoxyethyl, ethoxyethoxyethyl, propyloxyethoxyethyl, and methoxypropyl.

The organic group is preferably a cycloalkyl group having 3 or more and 10 or less carbon atoms, more preferably a cycloalkyl group having 3 or more and 6 or less carbon atoms. Examples of the cycloalkyl group include cyclopropyl, cyclobutyl, cyclopentyl, cyclohexyl, cycloheptyl, and cyclooctyl.

The organic group is preferably a phenylalkyl group having 7 or more and 20 or less carbon atoms, more preferably a phenylalkyl group having 7 or more and 10 or less carbon atoms. The organic group is also preferably a naphthylalkyl group having 11 or more and 20 or less carbon atoms, more preferably a naphthylalkyl group having 11 or more and 14 or less carbon atoms. Examples of the phenylalkyl group include benzyl, 2-phenylethyl, 3-phenylpropyl, and 4-phenylbutyl. Examples of the naphthylalkyl group include a-naphthylmethyl, β-naphthylmethyl, 2-(α-naphthyl)ethyl, and 2-(β-naphthyl)ethyl. The phenylalkyl or naphthylalkyl group may further have a substituent on the phenyl or naphthyl group.

When the organic group is a heterocyclyl group, examples of the heterocyclyl group are the same as those of the heterocyclyl group of $R^{c4}$ in Formula (c3), and the heterocyclyl group may further have a substituent.

When the organic group is a heterocyclyl group, it may be an aliphatic heterocyclic group or an aromatic heterocyclic group. The heterocyclyl group is preferably a five- or six-membered monocyclic ring containing one or more N, S, or O atoms or preferably a heterocyclyl group including such monocyclic rings fused together or including such a monocyclic ring and a benzene ring fused together. When the heterocyclyl group is a fused ring, it should have up to three rings. The heterocyclic ring constituting the heterocyclyl group described above may be furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, or tetrahydrofuran.

The phenyl, naphthyl, or heterocyclyl group in the organic group may have a substituent, such as an alkyl group having 1 or more and 6 or less carbon atoms, an alkoxy group having 1 or more and 6 or less carbon atoms, a halogenated alkyl group having 1 or more and 6 or less carbon atoms, a halogenated alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group having an alkyl group of 1 or more and 6 or less carbon atoms, a dialkylamino group having an alkyl group of 1 or more and 6 or less carbon atoms, a benzoyl group, a halogen atom, a nitro group, or a cyano group. The phenyl, naphthyl, or heterocyclyl group in the organic group may have any suitable number of substituents and preferably has 1 or more and 4 or less substituents. The phenyl, naphthyl, or heterocyclyl group in the organic group may have two or more substituents the same as or different from one another.

In Formula (e1), $R^{e1}$, $R^{e2}$, and $R^{e3}$ are each independently a hydrogen atom or an organic group, and at least one of $R^{e1}$, $R^{e2}$, or $R^{e3}$ is an aromatic group-containing group. In Formula (e2), $R^{e4}$, $R^{e5}$, and $R^{e6}$ are each independently a hydrogen atom or an organic group, and at least one of $R^{e4}$, $R^{e5}$, or $R^{e6}$ is an aromatic group-containing group. The aromatic ring in the aromatic group-containing group may be an aromatic hydrocarbon ring or an aromatic heterocyclic ring. The aromatic group-containing group is preferably a hydrocarbon group. The aromatic group-containing group is preferably an aromatic hydrocarbon group (aryl group) or an aralkyl group. The aromatic hydrocarbon group may be phenyl, naphthalen-1-yl, or naphthalen-2-yl. In particular, the aromatic hydrocarbon group is preferably phenyl. The aralkyl group may be benzyl, 2-phenylethyl, 3-phenylpropyl, or 4-phenylbutyl.

In Formula (e1), at least one of $R^{e1}$, $R^{e2}$, or $R^{e3}$ is preferably a group represented by $Ar^{e1}—CH_2—$. In Formula (e2), $R^{e4}$ is preferably a group represented by $Ar^{e1}—CH_2—$. $Ar^{e1}$ is an optionally substituted aromatic group. The aromatic group of $Ar^{e1}$ may be an aromatic hydrocarbon group or an aromatic heterocyclic group. The aromatic group of $Ar^{e1}$ is preferably an aromatic hydrocarbon group. The aromatic hydrocarbon group may be phenyl, naphthalen-1-yl, or naphthalen-2-yl. In particular, the aromatic hydrocarbon group is preferably phenyl. The aromatic group of $Ar^{e1}$ may have a substituent, examples of which are the same as those of the substituent that the organic group of $R^{e1}$, $R^{e2}$, $R^{e3}$, $R^{e4}$, $R^{e5}$, or $R^{e6}$ may have when it is phenyl, naphthyl, or heterocyclyl.

Preferred examples of the amine compound of Formula (e1) include triphenylamine, N,N-diphenylbenzylamine, N-phenyldibenzylamine, tribenzylamine, N,N-dimethylphenylamine, N-methyldiphenylamine, N,N-dimethylbenzylamine, N-methyldibenzylamine, N-methyl-N-benzylphenylamine, N,N-diethylphenylamine, N-ethyldiphenylamine, N,N-diethylbenzylamine, N-ethyldibenzylamine, and N-ethyl-N-benzylphenylamine.

Preferred examples of the imine compound of Formula (e2) include N-benzylphenylmethanimine, N-benzyldiphenylmethanimine, N-benzyl-1-phenylethanimine, and N-benzylpropan-2-imine.

The content of the nitrogen-containing compound (E) in the photosensitive composition may be any level as long as the desired effect will not be impaired. The content of the nitrogen-containing compound (E) is preferably 5 mass % or more and 25 mass % or less, more preferably 7 mass % or more and 20 mass % or less, based on the mass of the photopolymerizable compounds (A).

Triazine Compound (F)

For production of materials with higher refractive indices from the photosensitive composition, the photosensitive composition may contain a triazine compound (F), such as a compound of Formula (F1) below.

(F1)

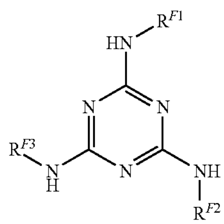

In Formula (F1), $R^{F1}$, $R^{F2}$, and $R^{F3}$ are each independently an optionally substituted monocyclic aromatic group or an optionally substituted fused aromatic group, provided that $R^{F1}$, $R^{F2}$, and $R^{F3}$ have no radically or cationically polymerizable group-containing group, the monocyclic aromatic group or the fused aromatic group may have a substituent containing no aromatic ring, and the three —NH— groups bonded to the triazine ring are bonded to the aromatic rings in $R^{F1}$, $R^{F2}$, and $R^{F3}$, respectively.

The monocyclic aromatic group of $R^{F1}$, $R^{F2}$, or $R^{F3}$ may be an aromatic hydrocarbon group or an aromatic heterocyclic group. The monocyclic aromatic group may be phenyl, pyridinyl, pyrimidinyl, pyrazinyl, pyridazinyl, furanyl, thienyl, oxazolyl, or thiazolyl.

The monocyclic aromatic group may have a substituent, examples of which include a halogen atom, a hydroxyl group, a mercapto group, a cyano group, a nitro group, and a monovalent organic group, provided that the monovalent organic group has no aromatic ring. The substituent halogen atom may be fluorine, chlorine, bromine, or iodine. The monovalent organic group may be alkyl, alkoxy, alkoxyalkyl, aliphatic acyl, aliphatic acyloxy, alkoxycarbonyl, alkylthio, or aliphatic acylthio.

The substituent monovalent organic group may have any number of carbon atoms as long as the desired effect will not be impaired. For example, the substituent monovalent organic group preferably has 1 or more and 20 or less carbon atoms, more preferably 1 or more and 12 or less carbon atoms, even more preferably 1 or more and 8 or less carbon atoms. The number of carbon atoms in the alkoxyalkyl, aliphatic acyl, aliphatic acyloxy, alkoxycarbonyl, alkoxyalkylthio, or aliphatic acylthio group should have a lower limit of 2.

Preferred examples of the substituent alkyl group include methyl, ethyl, n-propyl, isopropyl, n-butyl, isobutyl, sec-butyl, tert-butyl, n-pentyl, n-hexyl, n-heptyl, and n-octyl.

Preferred examples of the substituent alkoxy group include methoxy, ethoxy, n-propyloxy, isopropyloxy, n-butyloxy, isobutyloxy, sec-butyloxy, tert-butyloxy, n-pentyloxy, n-hexyloxy, n-heptyloxy, and n-octyloxy.

Preferred examples of the substituent alkoxyalkyl group include methoxymethyl, ethoxymethyl, n-propyloxymethyl, n-butyloxymethyl, 2-methoxyethyl, 2-ethoxyethyl, 2-n-propyloxyethyl, 2-n-butyloxyethyl, 3-methoxy-n-propyloxy, 3-ethoxy-n-propyloxy, 3-n-propyloxy-n-propyloxy, 3-n-butyloxy-n-propyloxy, 4-methoxy-n-butyloxy, 4-ethoxy-n-butyloxy, 4-n-propyloxy-n-butyloxy, and 4-n-butyloxy-n-butyloxy.

Preferred examples of the substituent aliphatic acyl group include acetyl, propionyl, butanoyl, pentanoyl, hexanoyl, heptanoyl, and octanoyl.

Preferred examples of the substituent aliphatic acyloxy group include acetoxy, propionyloxy, butanoyloxy, pentanoyloxy, hexanoyloxy, heptanoyloxy, and octanoyloxy.

Preferred examples of the substituent alkoxycarbonyl group include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, n-hexyloxycarbonyl, n-heptyloxycarbonyl, and n-octyloxycarbonyl.

Preferred examples of the substituent alkylthio group include methylthio, ethylthio, n-propylthio, isopropylthio, n-butylthio, isobutylthio, sec-butylthio, tert-butylthio, n-pentylthio, n-hexylthio, n-heptylthio, and n-octylthio.

Preferred examples of the substituent aliphatic acylthio group include acetylthio, propionylthio, butanoylthio, pentanoylthio, hexanoylthio, heptanoylthio, and octanoylthio.

The monocyclic aromatic group may have any number of substituents as long as the desired effect will not be impaired. The monocyclic aromatic group preferably has one or more and four or less substituents, more preferably one or two substituents, even more preferably one substituent. The monocyclic aromatic group may have two or more substituents different from one another.

The optionally substituted monocyclic aromatic group described above may be phenyl, 4-cyanophenyl, 3-cyanophenyl, 2-cyanophenyl, 2,3-dicyanophenyl, 2,4-dicyanophenyl, 2,5-dicyanophenyl, 2,6-dicyanophenyl, 3,4-dicyanophenyl, 3,5-dicyanophenyl, 4-nitrophenyl, 3-nitrophenyl, 2-nitrophenyl, 4-chlorophenyl, 3-chlorophenyl, 2-chlorophenyl, 4-bromophenyl, 3-bromophenyl, 2-bromophenyl, 4-iodophenyl, 3-iodophenyl, 2-iodophenyl, 4-methoxyphenyl, 3-methoxyphenyl, 2-methoxyphenyl, 4-methylphenyl, 3-methylphenyl, or 2-methylphenyl.

In particular, the optionally substituted monocyclic aromatic group is preferably phenyl, 4-cyanophenyl, 3-cyanophenyl, 2-cyanophenyl, 4-nitrophenyl, 3-nitrophenyl, or 2-nitrophenyl, more preferably phenyl or 4-cyanophenyl.

The fused aromatic group of $R^{F1}$, $R^{F2}$, or $R^{F3}$ is a fused polycyclic group including two or more monocyclic aromatic rings fused together and lacking one hydrogen atom. The fused aromatic group may include any number of monocyclic aromatic rings fused together. The fused aromatic group preferably has two or three monocyclic aromatic rings fused together, more preferably two monocyclic aromatic rings fused together. In other words, the fused aromatic group is preferably a bicyclic fused aromatic group or a tricyclic fused aromatic group, more preferably a bicyclic fused aromatic group. The fused aromatic group may be an aromatic hydrocarbon group or an aromatic heterocyclic group.

The bicyclic fused aromatic group may be, for example, naphthalen-1-yl, naphthalen-2-yl, quinolin-2-yl, quinolin-3- yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, benzoxazol-2-yl, benzoxazol-4-yl, benzoxazol-5-yl, benzoxazol-6-yl, benzoxazol-7-yl, benzothiazol-2-yl, benzothiazol-4-yl, benzothiazol-5-yl, benzothiazol-6-yl, or benzothiazol-7-yl.

The tricyclic fused aromatic group may be, for example, anthracen-1-yl, anthracen-2-yl, anthracen-9-yl, phenanthren-1-yl, phenanthren-2-yl, phenanthren-3-yl, phenanthren-4-yl, phenanthren-9-yl, acridin-1-yl, acridin-2-yl, acridin-3-yl, acridin-4-yl, or acridin-9-yl.

The polycyclic fused aromatic group, such as the bicyclic or tricyclic fused aromatic group, may have a substituent, examples of which are the same as those of the substituent that the monocyclic aromatic group may have.

The optionally substituted fused aromatic group described above is preferably naphthalen-1-yl, naphthalen-2-yl, quinolin-2-yl, quinolin-3-yl, quinolin-4-yl, quinolin-5-yl, quinolin-6-yl, quinolin-7-yl, quinolin-8-yl, benzothiazol-2-yl, or 2-mercaptobenzothiazol-6-yl.

In particular, the optionally substituted fused aromatic group is preferably naphthalen-1-yl, quinolin-3-yl, quinolin-4-yl, or 2-mercaptobenzothiazol-6-yl, more preferably naphthalen-1-yl.

In particular, for production of materials with a good balance between refractive index, surface appearance, and heat resistance from the photosensitive composition, the compound of Formula (F1) described above is preferably a compound with one or two of $R^{F1}$, $R^{F2}$, and $R^{F3}$ being optionally substituted naphthyl and with one or two of $R^{F1}$, $R^{F2}$, and $R^{F3}$ being 4-cyanophenyl or benzothiazolyl. The optionally substituted naphthyl group is preferably naphthalen-1-yl.

Preferred examples of the compound of Formula (F1) include compounds of the formulae below.

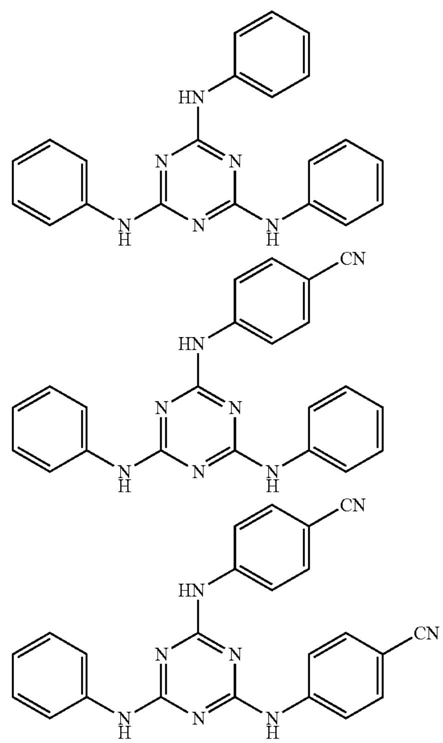

-continued

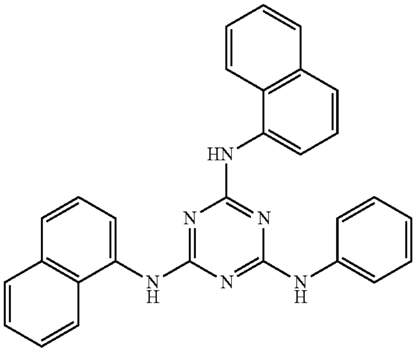

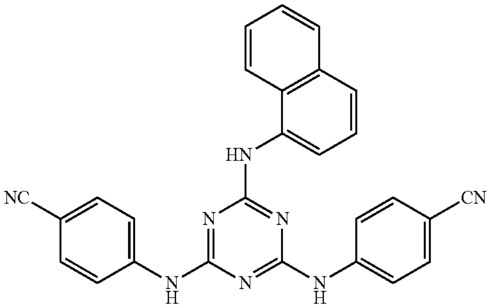

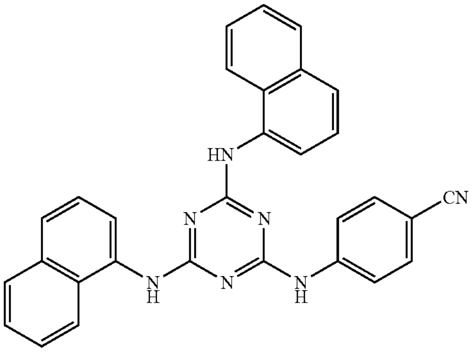

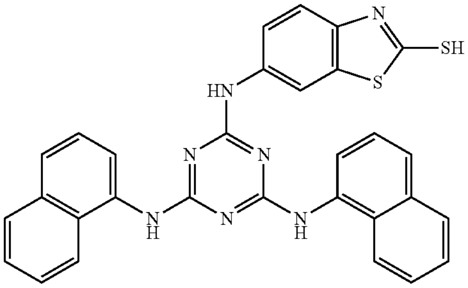

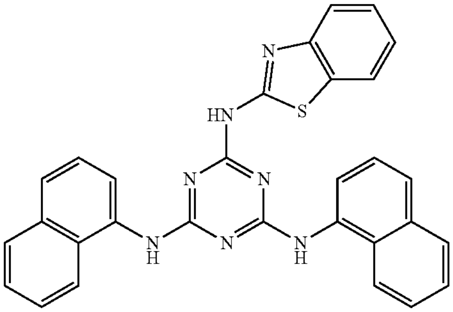

-continued

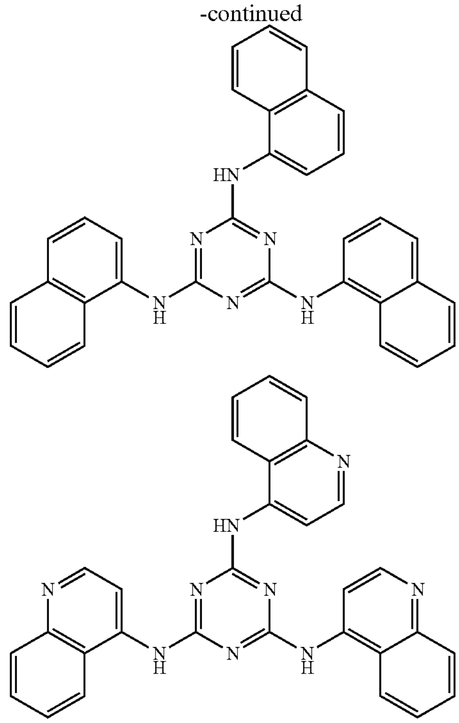

The compound of Formula (F1) may be produced by any suitable method. Typically, the compound of Formula (F1) may be produced by allowing a cyanuric halide, such as cyanuric chloride, to react with aromatic amines represented by $R^{F1}$—$NH_2$, $R^{F2}$—$NH_2$, and $R^{F3}$—$NH_2$. These amines may be allowed to react simultaneously or sequentially with the cyanuric halide. Preferably, these amines are allowed to react sequentially with the cyanuric halide.

The compound of Formula (F1) is usually synthesized in an organic solvent. Such an organic solvent may be any inert solvent that does not react with the cyanuric halide, the aromatic amines, the radically polymerizable group, or the cationically polymerizable group. Such a solvent may be any of organic solvent examples listed for the solvent (S) described later. For the production of the compound of Formula (F1), the cyanuric halide may be allowed to react at any suitable temperature with aromatic amines, such as the aromatic amines represented by $R^{F1}$—$NH_2$, $R^{F2}$—$NH_2$, and $R^{F3}$—$NH_2$. Typically, the reaction temperature is preferably 0° C. or more and 150° C. or less.

The content of the triazine compound (F) in the photosensitive composition may be any level as long as the desired effect will not be impaired. For example, the content of the triazine compound (F) in the photosensitive composition is preferably 0.1 parts by mass or more and 30 parts by mass or less, more preferably 0.3 parts by mass or more and 20 parts by mass or less, even more preferably 0.5 parts by mass or more and 15 parts by mass or less, based on the mass calculated by subtracting the mass of the solvent (S) described later from the mass of the photosensitive composition, which corresponds to 100 parts by mass.

Solvent (S)

The photosensitive composition may contain a solvent (S) for control of the ability to be applied and other purposes. The solvent (S) may be any type that does not compromise the desired effect.

Preferred examples of the solvent (S) include (poly) alkylene glycol monoalkyl ethers, such as ethylene glycol monomethyl ether, ethylene glycol monoethyl ether, ethylene glycol n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether (HO—$CH_2CH_2CH_2$—O—$CH_3$), propylene glycol monomethyl ether (HO—$C(CH_3)HCH_2$—O—$CH_3$ or $H_3C$—O—$C(CH_3)HCH_2$—OH), propylene glycol monoethyl ether (HO—$CH_2CH_2CH_2$—O—$CH_2CH_3$), propylene glycol monoethyl ether (HO—$C(CH_3)HCH_2$—O—$CH_2CH_3$ or $H_3CH_2C$—O—$C(CH_3)HCH_2$—OH), propylene glycol mono-n-propyl ether (HO—$CH_2CH_2CH_2$—O—$CH_2CH_2CH_3$), propylene glycol mono-n-propyl ether (HO—$C(CH_3)HCH_2$—O—$CH_2CH_2CH_3$ or $H_3CH_2CH_2C$—O—$C(CH_3)HCH_2$—OH), propylene glycol mono-n-butyl ether (HO—$CH_2CH_2CH_2$—O—$CH_2CH_2CH_2CH_3$), propylene glycol mono-n-butyl ether (HO—$C(CH_3)HCH_2$—O—$CH_2CH_2CH_2CH_3$ or $H_3CH_2CH_2CH_2C$—O—$C(CH_3)HCH_2$—OH), dipropylene glycol monoethyl ether (HO—$(CH_2CH_2CH_2$—$O)_2$—$CH_3$), dipropylene glycol monomethyl ether (HO—$(C(CH_3)HCH_2$—$O)_2$—$CH_3$ or $H_3C$—O—$(C(CH_3)HCH_2$—$O)_2$—H), dipropylene glycol monoethyl ether (HO—$(CH_2CH_2CH_2$—$O)_2$—$CH_2CH_3$), dipropylene glycol monoethyl ether (HO—$(C(CH_3)HCH_2$—$O)_2$—$CH_2CH_3$ or $H_3CH_2C$—O—$(C(CH_3)HCH_2$—$O)_2$—H), dipropylene glycol mono-n-propyl ether (HO—$(CH_2CH_2CH_2$—$O)_2$—$CH_2CH_2CH_3$ or $H_3CH_2CH_2C$—O—$(CH_2CH_2CH_2$—$O)_2$—H), dipropylene glycol mono-n-propyl ether (HO—$(C(CH_3)HCH_2$—$O)_2$—$CH_2CH_2CH_3$ or $H_3CH_2CH_2C$—O—$(C(CH_3)HCH_2$—$O)_2$—H), dipropylene glycol mono-n-butyl ether (HO—$(CH_2CH_2CH_2$—$O)_2$—$CH_2CH_2CH_2CH_3$ or $H_3CH_2CH_2CH_2C$—O—$(CH_2CH_2CH_2$—$O)_2$—H), dipropylene glycol mono-n-butyl ether (HO—$(C(CH_3)HCH_2$—$O)_2$—$CH_2CH_2CH_2CH_3$ or $H_3CH_2CH_2CH_2C$—O—$(C(CH_3)HCH_2$—$O)_2$—H), tripropylene glycol monomethyl ether (HO—$(CH_2CH_2CH_2$—$O)_3$—$CH_2CH_3$), tripropylene glycol monomethyl ether ($H_3C$—O—$(C(CH_3)HCH_2$—$O)_3$—H), tripropylene glycol monoethyl ether (HO—$(CH_2CH_2CH_2$—$O)_3$—$CH_2CH_3$), and tripropylene glycol monoethyl ether (HO—$(C(CH_3)HCH_2$—$O)_3$—$CH_2CH_3$ or $H_3CH_2C$—O—$(C(CH_3)HCH_2$—$O)_3$—H); (poly)alkylene glycol monoalkyl ether acetates, such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; ethers, such as ethylene glycol dimethyl ether, ethylene glycol diethyl ether, ethylene glycol methyl ethyl ether, diethylene glycol dimethyl ether, diethylene glycol methyl ethyl ether, diethylene glycol diethyl ether, propylene glycol dimethyl ether, propylene glycol diethyl ether, propylene glycol methyl ethyl ether, dipropylene glycol dimethyl ether, dipropylene glycol methyl ethyl ether, dipropylene glycol diethyl ether, and tetrahydrofuran; ketones, such as methyl ethyl ketone, cyclohexanone, 2-heptanone, and 3-heptanone; lactic acid alkyl esters, such as methyl 2-hydroxypropionate and ethyl 2-hydroxypropionate; esters, such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methoxybutyl acetate, 3-methyl-3-methoxybutyl acetate, 3-methyl-3-methoxybutyl propionate, ethyl acetate, n-propyl acetate, isopropyl acetate, n-butyl acetate, isobutyl acetate, n-pentyl formate, isopentyl acetate, n-butyl propionate, ethyl butyrate, n-propyl butyrate, isopropyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons, such as toluene and xylene; and amides, such as N-methylpyrrolidone, N,N-dimethylformamide, and N,N-dimethylacetamide, among which (poly)alkylene glycol monoalkyl ether acetates are preferred.

For successful application of the composition by inkjet printing, the solvent (S) preferably includes a solvent having a boiling point of 140° C. or more at atmospheric pressure and more preferably includes a high-boiling-point solvent (S1) having a boiling point of 170° C. or more at atmospheric pressure.

Examples of the solvent having a boiling point of 140° C. or more at atmospheric pressure include ethylene glycol mono-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether ($HO—CH_2CH_2CH_2—O—CH_3$), propylene glycol monoethyl ether ($HO—CH_2CH_2CH_2—O—CH_2CH_3$), propylene glycol mono-n-propyl ether ($HO—CH_2CH_2CH_2—O—CH_2CH_2CH_3$), propylene glycol mono-n-propyl ether ($HO—C(CH_3)HCH_2—O—CH_2CH_2CH_3$ or $H_3CH_2CH_2C—O—C(CH_3)HCH_2—OH$), propylene glycol mono-n-butyl ether ($HO—CH_2CH_2CH_2—O—CH_2CH_2CH_2CH_3$), propylene glycol mono-n-butyl ether ($HO—C(CH_3)HCH_2—O—CH_2CH_2CH_2CH_3$ or $H_3CH_2CH_2CH_2C—O—C(CH_3)HCH_2—OH$), dipropylene glycol monoethyl ether ($HO—(CH_2CH_2CH_2—O)_2—CH_3$), dipropylene glycol monomethyl ether ($HO—(C(CH_3)HCH_2—O)_2—CH_3$ or $H_3C—O—(C(CH_3)HCH_2—O)_2—H$), dipropylene glycol monoethyl ether ($HO—(CH_2CH_2CH_2—O)_2—CH_2CH_3$), dipropylene glycol monoethyl ether ($HO—(C(CH_3)HCH_2—O)_2—CH_2CH_3$ or $H_3CH_2C—O—(C(CH_3)HCH_2—O)_2—H$), dipropylene glycol mono-n-propyl ether ($HO—(CH_2CH_2CH_2—O)_2—CH_2CH_2CH_3$ or $H_3CH_2CH_2C—O—(CH_2CH_2CH_2—O)_2—H$), dipropylene glycol mono-n-propyl ether ($HO—(C(CH_3)HCH_2—O)_2—CH_2CH_2CH_3$ or $H_3CH_2CH_2C—O—(C(CH_3)HCH_2—O)_2—H$), dipropylene glycol mono-n-butyl ether ($HO—(CH_2CH_2CH_2—O)_2—CH_2CH_2CH_2CH_3$ or $H_3CH_2CH_2CH_2C—O—(CH_2CH_2CH_2—O)_2—H$), dipropylene glycol mono-n-butyl ether ($HO—C(CH_3)HCH_2—O)_2—CH_2CH_2CH_2CH_3$ or $H_3CH_2CH_2CH_2C—O—(C(CH_3)HCH_2—O)_2—H$), tripropylene glycol monomethyl ether ($HO—(CH_2CH_2CH_2—O)_3—CH_2CH_3$), tripropylene glycol monomethyl ether ($H_3C—O—(C(CH_3)HCH_2—O)_3—H$), tripropylene glycol monoethyl ether ($HO—(CH_2CH_2CH_2—O)_3—CH_2CH_3$), tripropylene glycol monoethyl ether ($HO—(C(CH_3)HCH_2—O)_3—CH_2CH_3$ or $H_3CH_2C—O—(C(CH_3)HCH_2—O)_3—H$), diethylene glycol monomethyl ether acetate, diethylene glycol monoethyl ether acetate, diethylene glycol dimethyl ether, cyclohexanone, 2-heptanone, ethyl 2-hydroxypropionate, ethyl 2-hydroxy-2-methylpropionate, ethyl 3-methoxypropionate, ethyl 3-ethoxypropionate, ethyl ethoxyacetate, ethyl hydroxyacetate, 3-methoxybutyl acetate, 3-methyl-3-methoxybutyl acetate, 3-methyl-3-methoxybutyl propionate, n-butyl butyrate, methyl acetoacetate, ethyl acetoacetate, ethyl 2-oxobutanoate, N-methylpyrrolidone, N,N-dimethylformamide, and N,N-dimethylacetamide.

Examples of the high-boiling-point solvent (S1) include ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol mono-n-butyl ether ($HO—CH_2CH_2CH_2—O—CH_2CH_2CH_2CH_3$), propylene glycol mono-n-butyl ether ($HO—C(CH_3)HCH_2—O—CH_2CH_2CH_2CH_3$ or $H_3CH_2CH_2CH_2C—O—C(CH_3)HCH_2—OH$), dipropylene glycol monoethyl ether ($HO—(CH_2CH_2CH_2—O)_2—CH_3$), dipropylene glycol monomethyl ether ($HO—(C(CH_3)HCH_2—O)_2—CH_3$ or $H_3C—O—(C(CH_3)HCH_2—O)_2—H$), dipropylene glycol monoethyl ether ($HO—(CH_2CH_2CH_2—O)_2—CH_2CH_3$), dipropylene glycol monoethyl ether ($HO—(C(CH_3)HCH_2—O)_2—CH_2CH_3$ or $H_3CH_2C—O—(C(CH_3)HCH_2—O)_2—H$), dipropylene glycol mono-n-propyl ether ($HO—(CH_2CH_2CH_2—O)_2—CH_2CH_2CH_3$ or $H_3CH_2CH_2C—O—(CH_2CH_2CH_2—O)_2—H$), dipropylene glycol mono-n-propyl ether ($HO—(C(CH_3)HCH_2—O)_2—CH_2CH_2CH_3$ or $H_3CH_2CH_2C—O—(C(CH_3)HCH_2—O)_2—H$), dipropylene glycol mono-n-butyl ether ($HO—(CH_2CH_2CH_2—O)_2—CH_2CH_2CH_2CH_3$ or $H_3CH_2CH_2CH_2C—O—(CH_2CH_2CH_2—O)_2—H$), dipropylene glycol mono-n-butyl ether ($HO—C(CH_3)HCH_2—O)_2—CH_2CH_2CH_2CH_3$ or $H_3CH_2CH_2CH_2C—O—(C(CH_3)HCH_2—O)_2—H$), tripropylene glycol monomethyl ether ($HO—(CH_2CH_2CH_2—O)_3—CH_2CH_3$), tripropylene glycol monomethyl ether ($H_3C—O—(C(CH_3)HCH_2—O)_3—H$), tripropylene glycol monoethyl ether ($HO—(CH_2CH_2CH_2—O)_3—CH_2CH_3$), tripropylene glycol monoethyl ether ($HO—(C(CH_3)HCH_2—O)_3—CH_2CH_3$ or $H_3CH_2C—O—(C(CH_3)HCH_2—O)_3—H$), diethylene glycol monomethyl ether acetate, diethylene glycol monoethyl ether acetate, diethylene glycol methyl ethyl ether, diethylene glycol diethyl ether, dipropylene glycol dimethyl ether, dipropylene glycol methyl ethyl ether, dipropylene glycol diethyl ether, ethyl hydroxyacetate, 3-methoxybutyl acetate, 3-methyl-3-methoxybutyl acetate, 3-methyl-3-methoxybutyl propionate, methyl acetoacetate, ethyl acetoacetate, ethyl 2-oxobutanoate, and N-methylpyrrolidone.

For ease of obtaining the desired effect, the ratio of the mass of the solvent having a boiling point of 140° C. or more or the high-boiling-point solvent (S1) having a boiling point of 170° C. or more to the mass of the solvent(s) (S) is preferably 20 mass % or more, more preferably 30 mass % or more, even more preferably 50 mass % or more, furthermore preferably 70 mass % or more, still more preferably 90 mass % or more, most preferably 100 mass %.

The content of the solvent(s) (S) in the photosensitive composition is preferably such that the content of the components other than the solvent(s) (S) in the composition is 1 mass % or more and 99 mass % or less, more preferably 5 mass % or more and 50 mass % or less, even more preferably 10 mass % or more and 30 mass % or less.

Additional Components

In addition to the components described above, if necessary, the photosensitive composition may contain, as an additional component, any of various additives. The additive may be a sensitizing agent, a curing accelerating agent, a filling agent, a dispersing agent, an adhesion promoting agent, such as a silane coupling agent, an antioxidizing agent, an aggregation preventing agent, a thermal polymerization inhibiting agent, a defoaming agent, a surface active agent, or the like. The content of the additive in the photosensitive composition may be appropriately selected taking into account the commonly used amount of the additive.

Method of Producing Cured Product

The photosensitive composition described above may be formed into a desired shape and then subjected to light exposure depending on the type of the initiating agent (C) to form a cured product.

The photosensitive composition may be shaped by any suitable method selected depending on the shape of the cured product to be formed. The shaping method may be, for example, coating or casting into a mold. Hereinafter, a method of producing a cured film will be described as a typical example of the method of producing a cured product.

First, the photosensitive composition is applied to a desired substrate to form a coating film, and then, if necessary, the solvent (S) is at least partially removed from the coating film.

The photosensitive composition may be applied to the substrate by any suitable method. For example, the photosensitive composition may be applied to the substrate using a contact transfer-type coating device, such as a roll coater, a reverse coater, a bar coater, or a slit coater, or a non-contact coating device, such as a spinner (rotary coating device) or a curtain flow coater, to form a coating film with a desired thickness. Alternatively, the coating film may be formed by a printing method, such as screen printing or inkjet printing. As mentioned above, the photosensitive composition is resistant to rapid drying and less likely to become thick or solidify in inkjet heads. Thus, the photosensitive composition can be successfully applied by inkjet printing.

After the photosensitive composition is applied to the substrate, if necessary, the coating film is preferably baked so that the solvent (S) is at least partially removed from the coating film. The baking temperature may be appropriately selected taking into account the boiling point and other properties of the solvent (S). The baking may also be performed at a low temperature under reduced pressure conditions.

The baking may be performed by any suitable method, such as a method of drying the coating film using a hot plate at a temperature of 80° C. or more and 150° C. or less, preferably 85° C. or more and 120° C. or less, for a time period of 60 seconds or more and 500 seconds or less.

The coating film formed as described above may have any suitable thickness. The thickness of the coating film may be appropriately selected depending on the intended use of the cured film. Typically, the thickness of the coating film may be appropriately controlled such that a cured film can be formed preferably with a thickness of 0.1 μm or more and 10 μm or less, more preferably with a thickness of 0.2 μm or more and 5 μm or less.

The coating film formed by the method described above is then subjected to light exposure to form a cured film.

The coating film may be subjected to light exposure under any conditions that allow curing to proceed successfully. For example, the light exposure may be performed by applying active energy rays, such as ultraviolet rays or excimer laser light. The dose of the applied energy rays is typically, but not limited to, 30 $mJ/cm^2$ or more and 5,000 $mJ/cm^2$ or less. After the light exposure, the exposed coating film may be baked by the same method as in the heating after the application.

EXAMPLES

Hereinafter, the present invention will be described in more detail with reference to examples, which are not intended to limit the scope of the present invention.

Synthesis Example 1

To a 500 mL volume reactor were added potassium carbonate (16.05 g, 0.12 mol), acrylic acid (8.37 g, 0.12 mol), and 200 mL of N-methylpyrrolidone (NMP). The resulting solution was stirred at room temperature for 10 minutes. To the solution was added 4-(bromomethyl)benzophenone (21.30 g, 0.08 mol). The solution containing 4-(bromomethyl)benzophenone was stirred at 40° C. for 2 hours, then cooled to room temperature, and then subjected to phase separation using water and toluene so that the reaction product was extracted into the organic phase. A crude composition was obtained by removing the solvent from the organic phase and purified by silica gel chromatography to give 20.1 g (97% yield) of Compound 1. The results of $^1$H-NMR analysis of Compound 1 are as follows.

$^1$H-NMR (DMSO): 5.12 (s, 2H), 5.83 (dd, 1H), 6.12 (dd, 1H), 6.41 (dd, 1H), 7.30-7.81 (m, 9H)

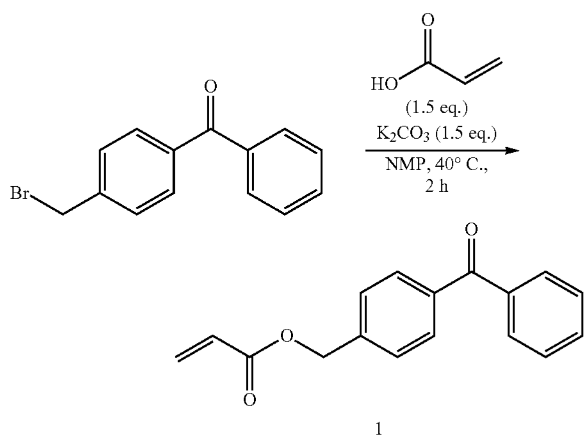

1

In the examples and comparative examples shown below, Compound 1 was used as the compound (A1). Compounds 2 and 3 shown below were used as the polyfunctional compound (A2-1). Compound 4 shown below was used as a comparative compound for the compound (A1). Compound 2: Dipentaerythritol hexaacrylate Compound 3: A mixture of dipentaerythritol EO adduct hexaacrylate and dipentaerythritol EO adduct pentaacrylate, which is composed mainly of dipentaerythritol EO adduct hexaacrylate and contains dipentaerythritol EO adduct pentaacrylate. Compound 4: 2-(2-Acryloyloxyethyl)oxybiphenyl Surface-treated titanium oxide ($TiO_2$) fine particles with an average particle size of 10 nm and surface-treated zirconium oxide ($ZrO_2$) fine particles with an average particle size of 10 nm were used as the inorganic fine particles (B). Solvents S1, S2, and S3 shown below were used as the solvent (S). S1: Propylene glycol monomethyl ether acetate S2: Dipropylene glycol monomethyl ether S3: Mixed solvent of equal amounts (masses) of tripropylene glycol monomethyl ether and dipropylene glycol monomethyl ether

Example 1 and Comparative Example 1

Photosensitive compositions of Example 1 and Comparative Example 1 were each obtained by dispersing and dissolving the photopolymerizable compounds (A) of the types shown in Table 1 in the amounts shown in Table 1 and 1 part by mass of bis(2,4,6-trimethylbenzoyl)-phenylphosphine oxide (the initiating agent (C)) in the solvent (S) of the type shown in Table 1 such that the total mass of the photopolymerizable compounds (A) and the initiating agent (C) made up 10 mass % of the mass of the resulting photosensitive composition.

Each of the resulting photosensitive compositions was used to form a cured film by the method shown below, and the curing rate and the film thickness decrease were evaluated by the methods shown below. The evaluation results are shown in Table 1.

Evaluation of Curing Rate

The photosensitive composition was applied to a silicon substrate. The film of the photosensitive composition was then heated at 100° C. for 2 minutes to form a 0.2 μm-thick coating film. The resulting coating film was exposed to light at a dose of 5 J/$cm^2$. Before and after the exposure to light, the coating film was subjected to FT-IR analysis to measure the peak corresponding to C═C (1408 $cm^{-1}$). The rate of reaction of the carbon-carbon unsaturated double bond was calculated based on the rate of decrease in the peak intensity. The FT-IR analysis was performed using an FT-IR spectrometer (manufactured by Thermo Fisher Scientific). The calculated rate of decrease in the peak intensity was used to evaluate the curing rate according to the criteria below. A (High curing rate): The rate of decrease in the peak intensity is 95% or more. B (Medium curing rate): The rate of decrease in the peak intensity is 90% or more and less than 95%. C (Low curing rate): The rate of decrease in the peak intensity is less than 90%.

Evaluation of Film Thickness Decrease

The photosensitive composition was applied to a silicon substrate. The film of the photosensitive composition was then heated at 100° C. for 2 minutes to form a 0.2 μm-thick coating film. The resulting coating film was exposed to light at a dose of 5 J/$cm^2$. The cured film resulting from the light exposure was heated at 100° C. for 10 minutes. The thicknesses of the cured film measured before and after the heating were used to calculate the rate of decrease in the cured film thickness. The cured film thickness was measured using a rotary compensating high-speed spectroscopic ellipsometer (manufactured by J. A. Woollam Japan). The calculated rate of decrease in the film thickness was used to evaluate the film thickness decrease according to the criteria below. A (Good retention): The rate of decrease in the film thickness is 5% or less. B (Fair retention): The rate of decrease in the film thickness is more than 5% and 10% or less. C (Poor retention): The rate of decrease in the film thickness is more than 10%.

TABLE 1

| | Photopolymerizable compounds (A) | | | | Solvent | | Film |
|---|---|---|---|---|---|---|---|
| | Compound (A1) or comparative compound | | Polyfunctional compound (A2-1) | | | | |
| | Type | Parts by mass | Type | Parts by mass | (S) Type | Curing rate | thickness decrease |
| Example 1 | Compound 1 | 49.5 | Compound 2 | 49.5 | S1 | A | A |
| Comparative Example 1 | Compound 4 | 49.5 | Compound 2 | 49.5 | S1 | C | C |

A comparison between the results of Example 1 and Comparative Example 1 shows that the photosensitive composition of the example, which contains a combination of the compound (A1) (the photopolymerizable compound (A) having the structure of Formula (A1) above) and the polyfunctional compound (A2-1), is highly curable and can form a cured film that is resistant to mass loss during heating. On the other hand, it is apparent that the photosensitive composition of the comparative example, which contains a photopolymerizable compound (A) other than the compound (A1) having the structure of Formula (A1) above, is not highly curable and will form a cured film that is prone to mass loss during heating.

Examples 2 to 37 and Comparative Examples 2 and 3

Photosensitive compositions of Examples 2 to 37 and Comparative Examples 2 and 3 were each obtained by dissolving the photopolymerizable compounds (A) of the types shown in Table 2 or 3 in the amounts shown in Table 2 or 3 and 1 part by mass of bis(2,4,6-trimethylbenzoyl)-phenylphosphine oxide (the initiating agent (C)) and dispersing the inorganic fine particles (B) of the type shown in Table 2 or 3 in the amount shown in Table 2 or 3 in the solvent (S) of the type shown in Table 2 or 3 such that the total mass of the photopolymerizable compounds (A), the inorganic fine particles (B), and the initiating agent (C) made up 10 mass % of the mass of the resulting photosensitive composition.

Each of the resulting photosensitive compositions was used to form a cured film by the method shown below, and the curing rate and the film thickness decrease were evaluated by the methods shown below. The evaluation results are shown in Tables 2 and 3.

Evaluation of Curing Rate

The photosensitive composition was applied to a silicon substrate. The film of the photosensitive composition was then heated at 100° C. for 2 minutes to form a 0.2 μm-thick coating film. The resulting coating film was exposed to light at a dose of 5 J/$cm^2$. Before and after the exposure to light, the coating film was subjected to FT-IR analysis to measure the peak corresponding to C═C (1408 $cm^{-1}$). The rate of reaction of the carbon-carbon unsaturated double bond was calculated based on the rate of decrease in the peak intensity. The FT-IR analysis was performed using an FT-IR spectrometer (manufactured by Thermo Fisher Scientific). The calculated rate of decrease in the peak intensity was used to evaluate the curing rate according to the criteria below. A (Excellent curing rate): The rate of decrease in the peak intensity is 90% or more. B (Good curing rate): The rate of decrease in the peak intensity is 85% or more and less than 90%. C (Fair curing rate): The rate of decrease in the peak intensity is 80% or more and less than 85%. D (Poor curing rate): The rate of decrease in the peak intensity is less than 80%.

Evaluation of Film Thickness Decrease

The photosensitive composition was applied to a silicon substrate. The film of the photosensitive composition was then heated at 100° C. for 2 minutes to form a 0.2 μm-thick coating film. The resulting coating film was exposed to light at a dose of 5 $J/cm^2$. The cured film resulting from the light exposure was heated at 100° C. for 10 minutes. The thicknesses of the cured film measured before and after the heating were used to calculate the rate of decrease in the cured film thickness. The cured film thickness was measured using a rotary compensating high-speed spectroscopic ellipsometer (manufactured by J. A. Woollam Japan). The calculated rate of decrease in the film thickness was used to evaluate the film thickness decrease according to the criteria below. A (Good retention): The rate of decrease in the film thickness is 1% or less. B (Fair retention): The rate of decrease in the film thickness is more than 1% and 5% or less. C (Poor retention): The rate of decrease in the film thickness is more than 5%.

TABLE 2

| | Photopolymerizable compounds (A) | | | | Inorganic fine particles (B) | | Solvent | | Film |
|---|---|---|---|---|---|---|---|---|---|
| | Compound (A1) or comparative compound | | Polyfunctional compound (A2-1) | | | | | | |
| | Type | Parts by mass | Type | Parts by mass | Type | Parts by mass | (S) Type | Curing rate | thickness decrease |
| Example 2 | Compound 1 | 9.5 | Compound 2 | 9.5 | $TiO_2$ | 80 | S1 | A | A |
| Example 3 | Compound 1 | 12 | Compound 2 | 12 | $TiO_2$ | 75 | S1 | A | A |
| Example 4 | Compound 1 | 14.5 | Compound 2 | 14.5 | $TiO_2$ | 70 | S1 | A | A |
| Example 5 | Compound 1 | 9.5 | Compound 2 | 9.5 | $TiO_2$ | 80 | S2 | A | A |
| Example 6 | Compound 1 | 12 | Compound 2 | 12 | $TiO_2$ | 75 | S2 | A | A |
| Example 7 | Compound 1 | 14.5 | Compound 2 | 14.5 | $TiO_2$ | 70 | S2 | A | A |
| Example 8 | Compound 1 | 9.5 | Compound 2 | 9.5 | $TiO_2$ | 80 | S3 | A | A |
| Example 9 | Compound 1 | 12 | Compound 2 | 12 | $TiO_2$ | 75 | S3 | A | A |
| Example 10 | Compound 1 | 14.5 | Compound 2 | 14.5 | $TiO_2$ | 70 | S3 | A | A |
| Example 11 | Compound 1 | 9.5 | Compound 3 | 9.5 | $TiO_2$ | 80 | S1 | A | A |
| Example 12 | Compound 1 | 12 | Compound 3 | 12 | $TiO_2$ | 75 | S1 | A | A |
| Example 13 | Compound 1 | 14.5 | Compound 3 | 14.5 | $TiO_2$ | 70 | S1 | A | A |
| Example 14 | Compound 1 | 9.5 | Compound 3 | 9.5 | $TiO_2$ | 80 | S2 | A | A |
| Example 15 | Compound 1 | 12 | Compound 3 | 12 | $TiO_2$ | 75 | S2 | A | A |
| Example 16 | Compound 1 | 14.5 | Compound 3 | 14.5 | $TiO_2$ | 70 | S2 | A | A |
| Example 17 | Compound 1 | 9.5 | Compound 3 | 9.5 | $TiO_2$ | 80 | S3 | A | A |
| Example 18 | Compound 1 | 12 | Compound 3 | 12 | $TiO_2$ | 75 | S3 | A | A |
| Example 19 | Compound 1 | 14.5 | Compound 3 | 14.5 | $TiO_2$ | 70 | S3 | A | A |

TABLE 3

| | Photopolymerizable compounds (A) | | | | Inorganic fine particles (B) | | Solvent | | Film |
|---|---|---|---|---|---|---|---|---|---|
| | Compound (A1) or comparative compound | | Polyfunctional compound (A2-1) | | | | | | |
| | Type | Parts by mass | Type | Parts by mass | Type | Parts by mass | (S) Type | Curing rate | thickness decrease |
| Example 20 | Compound 1 | 9.5 | Compound 2 | 9.5 | $ZrO_2$ | 80 | S1 | A | A |
| Example 21 | Compound 1 | 12 | Compound 2 | 12 | $ZrO_2$ | 75 | S1 | A | A |
| Example 22 | Compound 1 | 14.5 | Compound 2 | 14.5 | $ZrO_2$ | 70 | S1 | A | A |
| Example 23 | Compound 1 | 9.5 | Compound 2 | 9.5 | $ZrO_2$ | 80 | S2 | A | A |
| Example 24 | Compound 1 | 12 | Compound 2 | 12 | $ZrO_2$ | 75 | S2 | A | A |
| Example 25 | Compound 1 | 14.5 | Compound 2 | 14.5 | $ZrO_2$ | 70 | S2 | A | A |
| Example 26 | Compound 1 | 9.5 | Compound 2 | 9.5 | $ZrO_2$ | 80 | S3 | A | A |
| Example 27 | Compound 1 | 12 | Compound 2 | 12 | $ZrO_2$ | 75 | S3 | A | A |
| Example 28 | Compound 1 | 14.5 | Compound 2 | 14.5 | $ZrO_2$ | 70 | S3 | A | A |
| Example 29 | Compound 1 | 9.5 | Compound 3 | 9.5 | $ZrO_2$ | 80 | S1 | A | A |
| Example 30 | Compound 1 | 12 | Compound 3 | 12 | $ZrO_2$ | 75 | S1 | A | A |
| Example 31 | Compound 1 | 14.5 | Compound 3 | 14.5 | $ZrO_2$ | 70 | S1 | A | A |
| Example 32 | Compound 1 | 9.5 | Compound 3 | 9.5 | $ZrO_2$ | 80 | S2 | A | A |
| Example 33 | Compound 1 | 12 | Compound 3 | 12 | $ZrO_2$ | 75 | S2 | A | A |
| Example 34 | Compound 1 | 14.5 | Compound 3 | 14.5 | $ZrO_2$ | 70 | S2 | A | A |
| Example 35 | Compound 1 | 9.5 | Compound 3 | 9.5 | $ZrO_2$ | 80 | S3 | A | A |
| Example 36 | Compound 1 | 12 | Compound 3 | 12 | $ZrO_2$ | 75 | S3 | A | A |
| Example 37 | Compound 1 | 14.5 | Compound 3 | 14.5 | $ZrO_2$ | 70 | S3 | A | A |
| Comparative Example 2 | comparative compound 1 | 9.5 | Compound 2 | 9.5 | $TiO_2$ | 80 | S1 | D | C |
| Comparative Example 3 | comparative compound 1 | 9.5 | Compound 2 | 9.5 | $ZrO_2$ | 80 | S1 | D | C |

A comparison between the results of Examples 2 to 37 and Comparative Examples 2 and 3 shows that the photosensitive composition of each of the examples, which contains a combination of the compound (A1) (the photopolymerizable compound (A) having the structure of Formula (A1) above) and the polyfunctional compound (A2-1), is highly curable and can form a cured film that is resistant to mass loss during heating. On the other hand, it is apparent that the photosensitive composition of each of the comparative examples, which contains a photopolymerizable compound (A) other than the compound (A1) having the structure of Formula (A1) above, is not highly curable and will form a cured film that is prone to mass loss during heating.

What is claimed is:

1. A photosensitive composition comprising: photopolymerizable compounds (A); and an initiating agent (C), the photopolymerizable compounds (A) including: a compound (A1) of Formula (A1):

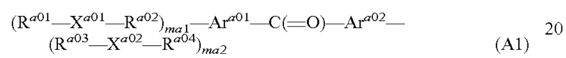

$$(R^{a01}—X^{a01}—R^{a02})_{ma1}—Ar^{a01}—C(=O)—Ar^{a02}—(R^{a03}—X^{a02}—R^{a04})_{ma2} \quad (A1)$$

wherein $Ar^{a01}$ is an aromatic group having 6 or more and 12 or less carbon atoms, having a valence of ma1+1, and optionally substituted with one or more selected from the group consisting of an alkyl group having 1 or more and 5 or less carbon atoms, a cyano group, and a halogen atom, $Ar^{a02}$ is an aromatic group having 6 or more and 12 or less carbon atoms, having a valence of ma2+1, and optionally substituted with one or more selected from the group consisting of an alkyl group having 1 or more and 5 or less carbon atoms, a cyano group, and a halogen atom, $R^{a01}$ and $R^{a04}$ are each independently a radically polymerizable group-containing group or a cationically polymerizable group-containing group, $X^{a01}$ and $X^{a02}$ are each independently O or S, $R^{a02}$ and $R^{a03}$ are each independently an alkylene group, ma1 is an integer of 1 or more and 3 or less, and ma2 is an integer of 0 or more and 3 or less; and at least one additional photopolymerizable compound (A2) different from the compound (A1), the at least one additional photopolymerizable compound (A2) including a polyfunctional compound (A2-1) having two or more polymerizable groups, the initiating agent (C) being different from the compound (A1).

2. The photosensitive composition according to claim 1, further comprising inorganic fine particles (B).

3. The photosensitive composition according to claim 2, wherein the inorganic fine particles (B) comprise metal oxide fine particles (B1), and wherein the metal oxide fine particles (B1) comprise at least one type of particles selected from the group consisting of titanium oxide fine particles, zirconium oxide fine particles, and niobium oxide fine particles.

4. The photosensitive composition according to claim 1, wherein the polyfunctional compound (A2-1) has four or more polymerizable groups.

5. The photosensitive composition according to claim 1, wherein the ratio of the mass of the compound (A1) to the mass of the photopolymerizable compounds (A) is 40 mass % or more and 60 mass % or less.

6. The photosensitive composition according to claim 1, wherein the radically polymerizable group-containing group is a (meth)acryloyl group-containing group, and the cationically polymerizable group-containing group is an epoxy group-containing group.

7. The photosensitive composition according to claim 1, wherein $Ar^{a01}$ is a group derived from benzene or naphthalene by removal of ma1+1 hydrogen atoms, and $Ar^{a02}$ is a group derived from benzene or naphthalene by removal of ma2+1 hydrogen atoms.

8. The photosensitive composition according to claim 1, wherein $R^{a02}$ and $R^{a03}$ are each independently an alkylene group having 1 or more and 5 or less carbon atoms.

9. A cured product comprising a product of curing of the photosensitive composition according to claim 1.

* * * * *